US012693297B2

(12) United States Patent
Hong et al.

(10) Patent No.: US 12,693,297 B2

(45) Date of Patent: Jul. 28, 2026

(54) COUMARIN-BASED CROSSLINKING REAGENTS

(71) Applicant: Ventana Medical Systems, Inc., Tucson, AZ (US)

(72) Inventors: Rui Hong, Oro Valley, AZ (US); Mark Lefever, Oro Valley, AZ (US); Eric May, Oro Valley, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 972 days.

(21) Appl. No.: 17/203,802

(22) Filed: Mar. 17, 2021

(65) Prior Publication Data

US 2021/0349101 A1 Nov. 11, 2021

Related U.S. Application Data

(63) Continuation of application No. PCT/EP2019/075013, filed on Sep. 18, 2019.

(60) Provisional application No. 62/733,814, filed on Sep. 20, 2018.

(51) Int. Cl.
*G01N 33/58* (2006.01)
*C09B 57/02* (2006.01)
*C09B 69/10* (2006.01)

(52) U.S. Cl.
CPC ........... *G01N 33/583* (2013.01); *C09B 57/02* (2013.01); *C09B 69/109* (2013.01)

(58) Field of Classification Search
CPC .................................................... G01N 33/583
See application file for complete search history.

(56) References Cited

U.S. PATENT DOCUMENTS

| | | | | |
|---|---|---|---|---|
| 4,469,797 | A * | 9/1984 | Albarella | G01N 33/531 530/389.8 |
| 10,883,999 | B2 | 1/2021 | Hong et al. | |
| 11,143,648 | B2 * | 10/2021 | Ashworth-Sharpe | G01N 33/583 |
| 12,130,284 | B2 * | 10/2024 | Ashworth-Sharpe | C09B 11/24 |
| 2010/0029017 | A1 | 2/2010 | Diwu et al. | |
| 2013/0109019 | A1 | 5/2013 | Murillo et al. | |
| 2013/0260379 | A1 * | 10/2013 | Alexander | C12Q 1/682 435/7.9 |
| 2014/0179877 | A1 | 6/2014 | Nilsson et al. | |
| 2014/0256626 | A1 | 9/2014 | Santi et al. | |
| 2017/0089911 | A1 * | 3/2017 | Bieniarz | C07D 209/14 |
| 2018/0120306 | A1 | 5/2018 | Kosmeder, II et al. | |

FOREIGN PATENT DOCUMENTS

| | | | | |
|---|---|---|---|---|
| EP | 0313274 A1 | | 4/1989 | |
| JP | S5983056 A | | 5/1984 | |
| JP | H01295165 A | | 11/1989 | |
| JP | 2015514214 A | | 5/2015 | |
| WO | WO 2004031405 | * | 4/2004 | |
| WO | 2007080114 | * | 7/2007 | A61K 47/60 |
| WO | 2007080114 A2 | | 7/2007 | |
| WO | 2008063378 A2 | | 5/2008 | |
| WO | 2012003476 A2 | | 1/2012 | |
| WO | 2012003478 A2 | | 1/2012 | |
| WO | 2013059323 | * | 4/2013 | A61K 47/60 |
| WO | 2013059323 A1 | | 4/2013 | |
| WO | 2014006124 | * | 1/2014 | A61K 47/48 |

OTHER PUBLICATIONS

Feng, Bioorganic & Medicinal Chemistry Letters, 8(7), 1998, 881-884.*
Kindermann, Bioorg. Med. Chem. Lett. 14 (2004) 2725-2728.*
Cao, Coumarin-Based Small-Molecule Fluorescent Chemosensors, Chemical Reviews, Sep. 2019, vol. 119 (18), p. 10403-10519.*
Kricka, Stains, labels and detection strategies for nucleic acids assays Ann Clin Biochem 2002, vol. 39, pp. 114-129.*
Kindermann Synthesis and characterization of bifunctional probes for the specific labeling of fusion proteins, Bioorganic & Medicinal Chemistry Letters 14 (2004) 2725-2728.*
Bartlett "Exploiting Chemical Diversity for Drug Discovery" Edited by Paul A Bartlett and Michael Entzeroth, The Royal Society of Chemistry, 2006, pp. 113-118.*
"Find ETDs Home » Thesis Resources » Find ETDs" Online: "https://ndltd.org/thesis-resources/find-etds/" Accessed Jan. 31, 2023.*
Irwin "ZINC—A Free Database of Commercially Available Compounds for Virtual Screening" J. Chem. Inf. Model. 2005, 45, 177-182.*
Kim "PubChem in 2021: new data content and improved web interfaces" Nucleic Acids Research, 2021, vol. 49, Database issue Published online Nov. 5, 2020.*
STN Registry/Zregistry (CAS Registrysm) Sep. 2016 2 pages.*
Xin Jin, ChemBioChem 2011, 12, 65-70, Synthesis of 7-Aminocoumarin by Buchwald-Hartwig Cross Coupling for Specific Protein Labeling in Living Cells, DOI: 10.1002/cbic.201000414.
Yangbo Feng, A Labeled Guanidine Ligand for Studying Sweet Taste, Bioorganic and Medical Chemistry Letters 8 (1998) 881-884.
International Search Report and Written Opinion for PCT/EP2019/075013, dated Jan. 3, 2020.
Juvonen RO et al., "Selective induction of coumarin 7-hydroxylase by pyrazole in D2 mice.", European journal of biochemistry, Oct. 1, 1985, vol. 152, No. 1, p. 3-8.

* cited by examiner

*Primary Examiner* — Nizal S Chandrakumar
(74) *Attorney, Agent, or Firm* — Charney IP Law LLC; Thomas M. Finetti

(57) ABSTRACT

Disclosed herein are novel coumarin-based reagents, e.g. linkers, and conjugates including one or more of the disclosed coumarin-based reagents. In some embodiments, the presence of a coumarin moiety within the coumarin-based reagents enables detection of labels which are typically difficult to detect, e.g. certain haptens.

3 Claims, 18 Drawing Sheets

RNA Probe Labeling asK07DIG asK07-CL-DIG

TS-dPEG8-maleimide:

TS-dPEG8-hydrazide:

TS-dPEG8-NHS Ester:

TS-dPEG7-NHS Alkyl Iodides:

TS-dPEG7-carbodiamide:

DNP-PEG4-N4-amino-dCTP as an Example for Probe Labels:

GAR-CL-DIG $A_{346}$ = 0.409
$A_{280}$ = 0.646

[CL] = 0.409/22,000 = 18.6 µM
$A_{280,IgG}$ = 0.646-0.409x0.1 = 0.605 (Assuming No Absorbance of DIG at 280nm)
[IgG] = 0.605/1.4 =0.432 mg/mL =2.88 µM
Therefore [CL]/[IgG] = 6.45

UV-Vis and Extinction Cofficient

Chemical Formula: C24H31F3N2011
Molecular Weight: 580.51

Absorbance (50 µM)

$\lambda_{max}$ = 346 nm
$\varepsilon_{346}$ = 22,000 $M^{-1}cm^{-1}$
$CF_{280}$ = 0.1

GAR-AP Conjugate

AP was Modified with NHS-PEG4-CL-PEG4-MAL (15 eq to Ap)
GAR was Reduced Using DTT (25 mM)
Feed Ratio of AP/GAR =3:1

| | A280 | A346 | Ratio |
|---|---|---|---|
| **AP-CL-MAL** | 0.417 | 0.399 | MAL/AP = 5.3 |
| **GAR-CL-AP A3** | 0.584 | 0.316 | AP/GAR = 2.25 |
| **GAR-CL-AP A5** | 0.72 | 0.376 | AP/GAR = 2 |
| **GAR-CL-AP A10** | 0.834 | 0.534 | Mostly Free AP |

AP Mw = 110,000 g/moL 1 mg/mL AP: $A_{280} = 1$ $[AP] = (A_{346}/22{,}000)/5.3$ $A_{280,\ Ap\ Conjugate} = A_{346} \times (A_{280,AP\text{-}CL\text{-}MAL}/A_{346,\ AP\text{-}CL\text{-}MAL})$ $A_{280,\ IgG} = A_{280} - A_{280,AP\ Conjugate}$

FIG. 23

SEC of GAR-CL-AP Conjugation

Fraction A3, A5 and A10 Were Further Analyzed and Tested

COUMARIN-BASED CROSSLINKING REAGENTS

CROSS REFERENCE TO RELATED APPLICATIONS

This application is a continuation of International Application No. PCT/EP2019/075013, filed on Sep. 18, 2019, which application claims the benefit of the filing date of U.S. Patent Application No. 62/733,814, which application was filed on Sep. 20, 2018, the disclosures of which are hereby incorporated by reference herein in their entireties.

BACKGROUND OF THE DISCLOSURE

Immunohistochemistry (IHC) refers to the processes of detecting, localizing, and/or quantifying antigens, such as a protein, in a biological sample using antibodies specific to the particular antigens. IHC provides the substantial advantage of identifying exactly where a particular protein is located within the tissue sample. It is also an effective way to examine the tissues themselves. In situ hybridization (ISH) refers to the process of detecting, localizing, and quantifying nucleic acids. Both IHC and ISH can be performed on various biological samples, such as tissue (e.g. fresh frozen, formalin fixed, paraffin embedded) and cytological samples. Recognition of the targets can be detected using various labels (e.g., chromogenic, fluorescent, luminescent, radiometric), irrespective of whether the target is a nucleic acid or an antigen. To robustly detect, locate, and quantify targets in a clinical setting, amplification of the recognition event is desirable as the ability to confidently detect cellular markers of low abundance becomes increasingly important for diagnostic purposes. For example, depositing at the marker's site hundreds or thousands of label molecules in response to a single antigen detection event enhances, through amplification, the ability to detect that recognition event.

The use of small molecules such as haptens, to detect tissue antigens and nucleic acids has become a prominent method in IHC. Haptens, in combination with anti-hapten antibodies are useful for detecting particular molecular targets. For example, specific binding moieties such as primary antibodies and nucleic acid probes can be labeled with one or more hapten molecules, and once these specific binding moieties are bound to their molecular targets they can be detected using an anti-hapten antibody conjugate that includes an enzyme as part of a chromogenic based detection system or a detectable label such as a fluorescent label. Binding of the detectable anti-hapten antibody conjugate to a sample indicates the presence of the target in a sample.

Some haptens are difficult to detect and, as a result, are commonly over estimated in hapten loading which, it is believed, leads to underestimation of conjugate concentration.

BRIEF SUMMARY OF THE DISCLOSURE

In one aspect of the present disclosure are compounds defined by the structure of any of Formulas (IA) or (IB):

(IA)

$$A-[L^1]_m-W-[L^2]_n-B,$$

-continued (IB)

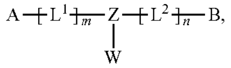

wherein

A and B are independently a reactive functional group, a detectable label, or an enzyme reactive moiety;

$L^1$ and $L^2$ are linkers;

W includes a substituted or unsubstituted coumarin moiety or a moiety which is a substituted or an unsubstituted derivative or analog of coumarin;

Z is a bond, a —CH— group, a —CH—$CH_2$— group or a —$CH_2$—CH— group; and m and n are independently an integer ranging from 1 to 4.

In some embodiments, both A and B are reactive functional groups (e.g. a carboxylic acid group). In some embodiments, A is a reactive functional group and B is a detectable label. In some embodiments, the detectable label is a hapten, a chromogen, or a fluorophore. In some embodiments, B is a hapten. In some embodiments, the hapten is selected from the group consisting of an oxazole, a pyrazole, a thiazole, a benzofurazan, a triterpene, a urea, a thiourea other than a rhodamine thiourea, a nitroaryl other than dinitrophenyl or trinitrophenyl, a rotenoid, a cyclolignan, a heterobiaryl, an azoaryl, and a benzodiazepine. In some embodiments, the hapten is selected from the group consisting of benzofuran haptens and thiazolesulfonamide haptens. In some embodiments, the hapten is selected from the group consisting of 5-nitro-3-pyrazolecarbamide (NP), 2-acetamido-4-methyl-5-thiazolesulfonamide (TS), 7-(diethylamino)-2-oxo-2H-chromene-3-carboxylic acid (DCC), and 2,1,3-benzoxadiazole-5-carbamide (BF). In some embodiments, A is an enzyme reactive moiety selected from the group consisting of tyramide moieties, moieties which are derivatives of tyramide moieties, and quinone methide precursor moieties.

In some embodiments, the compounds of any of Formulas (IA) or (IB) have an extinction coefficient of at least 10,000 M−1 cm−1. In other embodiments, the compounds of any of Formulas (IA) or (IB) have an extinction coefficient of at least 15,000 M−1 cm−1. In yet other embodiments, the compounds of any of Formulas (IA) or (IB) have an extinction coefficient of at least 20,000 M−1 cm−1. In further embodiments, the compounds of any of Formulas (IA) or (IB) have an extinction coefficient of at least 25,000 M−1 cm−1.

In some embodiments, the enzyme reactive moiety has the structure of Formula (VIIA):

(VIIA)

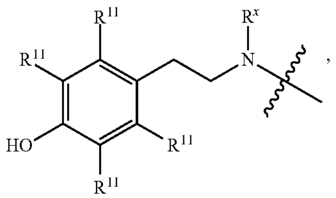

wherein each $R^{11}$ group is independently selected from hydrogen or a lower alkyl group having between 1 and 4 carbon atoms, and wherein $R^x$ is H or a $C_1$-$C_4$ alkyl group.

In some embodiments, the enzyme reactive moiety has the structure provided by Formula (VIIIA):

(VIIIA)

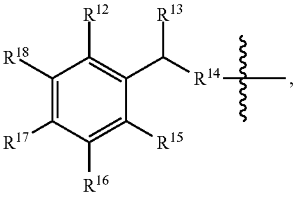

wherein $R^2$ is a group selected from phosphate, amide, nitro, urea, sulfate, methyl, ester, beta-lactam, or a sugar;

$R^{13}$ is a halide;

$R^1$, $R^{16}$, $R^{17}$, and $R^{18}$ are independently selected from hydrogen or an aliphatic group having between 1 and 4 carbon atoms; and $R^{14}$ is $-(CH_2)_wNH-$, $-O(CH_2)_wNH-$, $-N(H)C(O)(CH_2)_wNH-$, $-C(O)N(H)(CH_2)_wNH-$, $-(CH_2)_wO-$, $-O(CH_2)_wO-$, $-O(CH_2CH_2O)_w-$, $-N(H)C(O)(CH_2)_wO-$, $-C(O)N(H)(CH_2)_wO-$, $-C(o)N(H)(CH_2CH_2O)_w-$, $-(CH_2)_wS-$, $-O(CH_2)_wS-$, $-N(H)C(O)(CH_2)_wS-$, $-C(O)N(H)(CH_2)_wS-$, $-(CH_2)_wNH-$, $-C(O)N(H)(CH_2CH_2O)_wCH_2CH_2NH$, $-C(O)(CH_2CH_2O)_wCH_2CH_2NH-$, $-C(O)N(H)(CH_2)NHC(O)CH(CH_3)(CH_2)_wNH-$, or $-N(H)(CH_2)_wNH-$, where w is an integer ranging from 1 to 12.

In some embodiments, B is a reactive group capable of participating in a click-chemistry reaction (e.g. an azide group). In some embodiments, the group capable of participating in the click-chemistry reaction is a DBCO group, an azide, a TCO group, a alkene group, or a tetrazine group.

In some embodiments, W has the structure of either Formula (IVA) or (IVB):

(IVA)

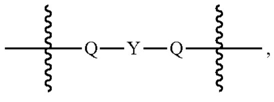

(IVB)

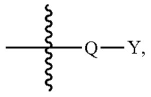

wherein Q is a bond or a substituted or unsubstituted, straight chain or branched $C_1$-$C_{16}$ alkyl group, $-[(CH_2CH_2)_j-O]_k-CH_2-$, $-[(CH_2)_j-O]_k-CH_2-$, where j is an integer ranging from 1 to 4 and k is an integer ranging from 1 to 16; $-N-R^x-$; $-C(O)-N-R^x-$; or $-N-R^x-C(O)-$, $R^x$ is H or a $C_1$-$C_4$ alkyl group; and Y is a substituted or unsubstituted coumarin moiety or a moiety which is a substituted or an unsubstituted derivative or analog of coumarin. In some embodiments, the substituted or unsubstituted coumarin moiety, or the moiety which is a substituted or an unsubstituted derivative or analog of coumarin includes one or more moieties selected from the group consisting of a substituted or unsubstituted, straight chain or branched $C_1$-$C_6$ alkyl group; a substituted or unsubstituted, straight chain or branched $C_1$-$C_6$ alkoxy group; a substituted or unsubstituted, straight chain or branched $C_1$-$C_6$ heteroalkyl group; a trifluoromethyl group; a hydroxyl group; a sulfate group; a cyano group; a halogen; a phosphate group; a saccharide; a carboxylic acid group; a nitro group; $-C(O)NR^xR^y$; $-S-R^x$; $-SO_2$; $-SO_2Cl$; $-SO_3H$; $-SO_4H$; $-SO_2NR^xR^y$; $-N(H)-NR^xR^y$; and $-NR^xR^y$; and wherein $R^x$ and $R^y$ are independently H or a $C_1$-$C_4$ alkyl group.

In some embodiments, W has the structure of either of Formula (VA) or (VB):

(VA)

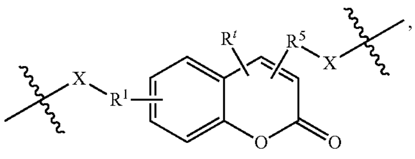

(VB)

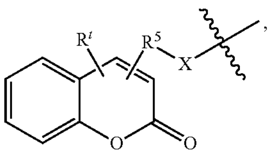

wherein the moiety of Formula (VA) may be substituted with 0, 1, 2, 3, or 4 $R^t$ groups; and wherein the compound of Formula (VB) may be substituted with 0, 1, 2, 3, 4, or 5 $R^t$ groups; and wherein each $R^t$ is independently selected from a substituted or unsubstituted, straight chain or branched $C_1$-$C_{12}$ alkyl group; a substituted or unsubstituted, straight chain or branched $C_1$-$C_{12}$ alkoxy group; a substituted or unsubstituted, straight chain or branched $C_1$-$C_{12}$ heteroalkyl group; a trifluoromethyl group; a hydroxyl group; a sulfate group; a cyano group; a halogen; a phosphate group; a saccharide; a carboxylic acid group; a nitro group; $-C(O)NR^xR^y$; $-S-R^x$; $-SO_2$; $-SO_2Cl$; $-SO_3H$; $-SO_4H$; $-SO_2NR^xR^y$; $-N(H)-NR^xR^y$; $-NR^xR^y$; and wherein $R^x$ and $R^y$ are independently H or a $C_1$-$C_4$ alkyl group;

$R^1$ is a $C_1$-$C_{10}$ substituted or unsubstituted, branched or unbranched alkyl group, $-O-$, $-O-CH_2-$, $-N(R^x)-$; or $-S-$.

$R^5$ is a $C_1$-$C_{10}$ substituted or unsubstituted, branched or unbranched alkyl group, $-C(O)-O-$; $-C(O)-N(H)-$; and each X is independently a bond or a substituted or unsubstituted, straight chain or branched $C_1$-$C_{16}$ alkyl group; $-[(CH_2)_j-O]-CH_2-$, where j is an integer ranging from 1 to 4 and k is an integer ranging from 1 to 16; $-N-R^x-$; $-C(O)-N-R^x-$; or $-N-R^x-C(O)-$, where $R^x$ is H or a $C_1$-$C_4$ alkyl group.

In some embodiments, W has the structure of either Formula (VC) or (VD):

(VC)

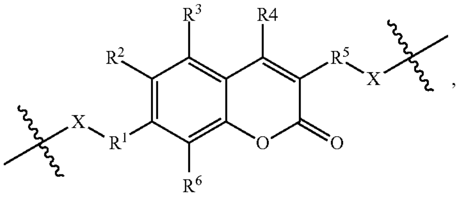

(VD)

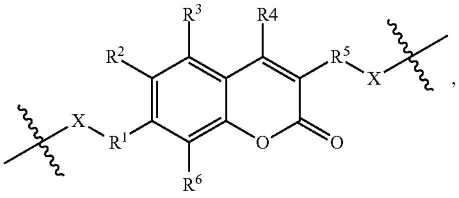

wherein $R^2$, $R^3$, $R^4$, $R^6$, and $R^7$ are independently selected from a substituted or unsubstituted, straight chain or branched $C_1$-$C_6$ alkyl group; a substituted or unsubstituted, straight chain or branched $C_1$-$C_6$ alkoxy group; a substituted or unsubstituted, straight chain or branched $C_1$-$C_6$ heteroalkyl group; a trifluoromethyl group; a hydroxyl group; a sulfate group; a cyano group; a halogen; a phosphate group; a saccharide; a carboxylic acid group; a nitro group; —C(O)$NR^xR^y$; —S—$R^x$; —$SO_2$; —$SO_2Cl$; —$SO_3H$; —$SO_4H$; —$SO_2NR^xR^y$; —N(H)—$NR^xR^y$; —$NR^xR^y$;

$R^5$ is a $C_1$-$C_{10}$ substituted or unsubstituted, branched or unbranched alkyl group, —C(O)—O—; —C(O)—N(H)—;

$R^1$ is a $C_1$-$C_{10}$ substituted or unsubstituted, branched or unbranched alkyl group, —O—, —O—$CH_2$—, —N($R^x$)—; or —S—; and each X is independently a bond or a substituted or unsubstituted, straight chain or branched $C_1$-$C_{16}$ alkyl group; —[$(CH_2)_j$—O]—$CH_2$—, where j is an integer ranging from 1 to 4 and k is an integer ranging from 1 to 16; —N—$R^x$—; —C(O)—N—$R^x$—; or —N—$R^x$—C(O)—; and wherein each $R^x$ and $R^y$ are independently H or a $C_1$-$C_4$ alkyl group.

In some embodiments, each $L^1$ and/or $L^2$ group independently has the Formula (VIA):

(VIA)

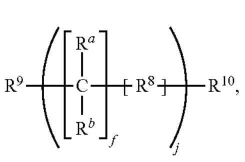

wherein f is 0 or an integer ranging from 1 to 24;

j is an integer ranging from 1 to 24;

$R^8$ is a bond or O, S, —N($R^c$)($R^d$), or —$N^+$($R^c$)($R^d$)($R^e$);

$R^a$ and $R^b$ are independently H, a $C_1$-$C_4$ alkyl group, F, Cl, or —N($R^c$)($R^d$);

$R^c$, $R^d$, and $R^e$ are independently selected from H or a $C_1$-$C_4$ alkyl group; and $R^9$ and $R^{10}$ are independently a bond or a group having up to 6 carbon atoms and including a carbonyl, an amide, an imide, an ester, an ether, an amine, an thione, or a thiol.

In another aspect of the present disclosure is a compound defined by the structure of any of Formulas (IXA) or (IXB):

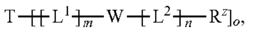

(IXA)

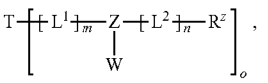

(IXB)

wherein

T is a substituent selected from a specific binding entity, an amino acid, a peptide, a protein, a saccharide, a nucleoside, a nucleotide, an oligonucleotide, a drug, a lipid, or a nanoparticle;

$R^z$ is a detectable label;

is an integer ranging from 1 to 10;

$L^1$ and $L^2$ are linkers;

W includes a substituted or unsubstituted coumarin moiety or a moiety which is a substituted or an unsubstituted derivative or analog of coumarin;

Z is a bond, a —CH— group, a —CH—$CH_2$— group or a —$CH_2$—CH— group; and m and n are independently an integer ranging from 1 to 4.

In some embodiments, T is an antibody. In some embodiments, the antibody is a primary antibody. In some embodiments, the antibody is a secondary antibody. In some embodiments, T is a nucleic acid. In some embodiments, $R^z$ is a hapten. In some embodiments, $R^z$ is an enzyme. In some embodiments, the enzyme is selected from the group consisting of a peroxidase and a phosphatase.

In some embodiments, W has the structure of either Formula (VC) or (VD):

(VC)

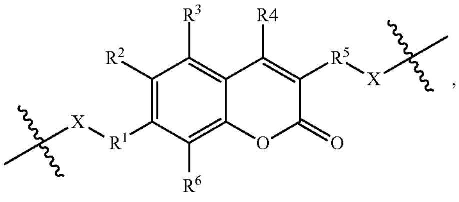

(VD)

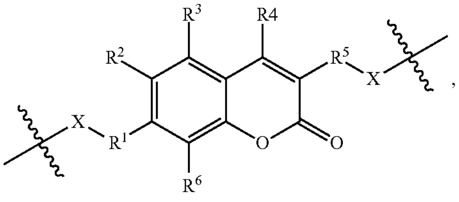

wherein $R^2$, $R^3$, $R^4$, $R^6$, and $R^7$ are independently selected from a substituted or unsubstituted, straight chain or branched $C_1$-$C_6$ alkyl group; a substituted or unsubstituted, straight chain or branched $C_1$-$C_6$ alkoxy group; a substituted or unsubstituted, straight chain or branched $C_1$-$C_6$ heteroalkyl group; a trifluoromethyl group; a hydroxyl group; a sulfate group; a cyano group; a halogen; a phosphate group; a saccharide; a carboxylic acid group; a nitro group; —C(O)$NR^xR^y$; —S—$R^x$; —$SO_2$; —$SO_2Cl$; —$SO_3H$; —$SO_4H$; —$SO_2NR^xR^y$; —N(H)—$NR^xR^y$; —$NR^xR^y$;

$R^5$ is a $C_1$-$C_{10}$ substituted or unsubstituted, branched or unbranched alkyl group, —C(O)—O—; —C(O)—N(H)—;

$R^1$ is a $C_1$-$C_{10}$ substituted or unsubstituted, branched or unbranched alkyl group, —O—, —O—$CH_2$—, —N($R^x$)—; or —S—; and each X is independently a bond or a substituted or unsubstituted, straight chain or branched $C_1$-$C_{16}$ alkyl group; —[$(CH_2)_j$—O]—$CH_2$—, where j is an integer ranging from 1 to 4 and k is an integer ranging from 1 to 16; —N—$R^x$—; —C(O)—N—$R^x$—; or —N—$R^x$—C(O)—; and wherein each $R^x$ and $R^y$ are independently H or a $C_1$-$C_4$ alkyl group.

In some embodiments, each $L^1$ and/or $L^2$ group independently has the Formula (VIA):

(VIA)

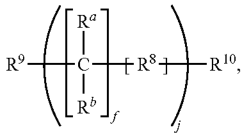

wherein f is 0 or an integer ranging from 1 to 24;

j is an integer ranging from 1 to 24;

$R^8$ is a bond or O, S, —N($R^c$)($R^d$), or —$N^+$($R^c$)($R^d$)($R^e$);

$R^a$ and $R^b$ are independently H, a $C_1$-$C_4$ alkyl group, F, Cl, or —N($R^c$)($R^d$);

$R^c$, $R^d$, and $R^e$ are independently selected from H or a $C_1$-$C_4$ alkyl group; and $R^9$ and $R^{10}$ are independently a bond or a group having up to 6 carbon atoms and including a carbonyl, an amide, an imide, an ester, an ether, an amine, an thione, or a thiol.

In another aspect of the present disclosure is a method of detecting one or more targets within a biological sample comprising: (a) labeling the sample with a primary antibody specific for one of the targets within the biological sample; (b) contacting the sample with a compound of any of Formulas (IXC) or (IXD):

(IXC)

$$Ab-[[L^1]_m-W-[L^2]_n-R^z]_o,$$

(IXD)

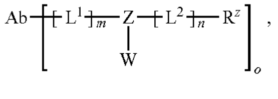

wherein

Ab is a secondary antibody;

$R^z$ is a detectable label;

is an integer ranging from 1 to 10;

$L^1$ and $L^2$ are linkers;

W includes a substituted or unsubstituted coumarin moiety or a moiety which is a substituted or an unsubstituted derivative or analog of coumarin;

Z is a bond, a —CH— group, a —CH—$CH_2$— group or a —$CH_2$—CH— group; and m and n are independently an integer ranging from 1 to 4; and (c) contacting the sample with one or more reagents to detect the detectable label $R^z$.

In some embodiments, Ab is an anti-primary antibody antibody. In some embodiments, the primary antibody is conjugated to a hapten, and wherein Ab is an anti-hapten antibody.

In another aspect of the present disclosure is a method of detecting one or more targets within a biological sample comprising: (a) labeling the sample an enzyme by contacting the sample with a conjugate comprising an enzyme and a primary antibody specific for one of the targets within the biological sample; (b) contacting the sample with a compound of any of Formulas (IA) or (IB):

(IA)

$$A-[L^1]_m-W-[L^2]_n-B,$$

(IB)

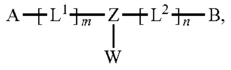

wherein

A is an enzyme reactive moiety;

B is a detectable label;

$L^1$ and $L^2$ are linkers;

W includes a substituted or unsubstituted coumarin moiety or a moiety which is a substituted or an unsubstituted derivative or analog of coumarin;

Z is a bond, a —CH— group, a —CH—$CH_2$— group or a —$CH_2$—CH— group; and m and n are independently an integer ranging from 1 to 4; and (c) contacting the sample with one or more reagents to detect the detectable label B.

In some embodiments, the compounds of any of Formulas (IA) or (IB) have an extinction coefficient of at least 10,000 M−1 cm−1. In other embodiments, the compounds of any of Formulas (IA) or (IB) have an extinction coefficient of at least 15,000 M−1 cm−1. In yet other embodiments, the compounds of any of Formulas (IA) or (IB) have an extinction coefficient of at least 20,000 M−1 cm−1. In further embodiments, the compounds of any of Formulas (IA) or (IB) have an extinction coefficient of at least 25,000 M−1 cm−1.

In some embodiments, W has the structure of either Formula (VC) or (VD):

(VC)

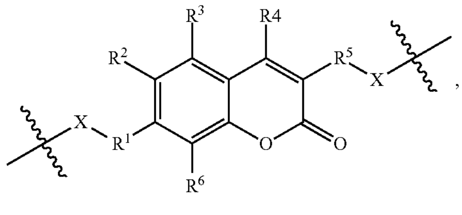

(VD)

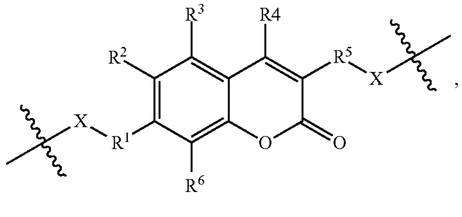

wherein $R^2$, $R^3$, $R^4$, $R^6$, and $R^7$ are independently selected from a substituted or unsubstituted, straight chain or branched $C_1$-$C_6$ alkyl group; a substituted or unsubstituted, straight chain or branched $C_1$-$C_6$ alkoxy group; a substituted or unsubstituted, straight chain or branched $C_1$-$C_6$ heteroalkyl group; a trifluoromethyl group; a hydroxyl group; a sulfate group; a cyano group; a halogen; a phosphate group; a saccharide; a carboxylic acid group; a nitro group; —C(O)N$R^xR^y$; —S—$R^x$; —$SO_2$; —$SO_2$Cl; —$SO_3$H; —$SO_4$H; —$SO_2$N$R^xR^y$; —N(H)—N$R^xR^y$; —N$R^xR^y$;

$R^5$ is a $C_1$-$C_{10}$ substituted or unsubstituted, branched or unbranched alkyl group, —C(O)—O—; —C(O)—N(H)—;

$R^1$ is a $C_1$-$C_{10}$ substituted or unsubstituted, branched or unbranched alkyl group, —O—, —O—$CH_2$—, —N($R^x$)—; or —S—; and each X is independently a bond or a substituted or unsubstituted, straight chain or branched $C_1$-$C_{16}$ alkyl group; —[$(CH_2)_j$—O]—$CH_2$—, where j is an integer ranging from 1 to 4 and k is an integer ranging from 1 to 16; —N—$R^x$—; —C(O)—N—$R^x$—; or —N—$R^x$—C(O)—; and wherein each $R^x$ and $R^y$ are independently H or a $C_1$-$C_4$ alkyl group.

BRIEF DESCRIPTION OF THE FIGURES

For a general understanding of the features of the disclosure, reference is made to the drawings. In the drawings, like reference numerals have been used throughout to identify identical elements.

FIG. 23 sets forth a table providing a ratio of absorbance spectra at wavelengths of 280 nm and 346 nm.

DETAILED DESCRIPTION

Figure 1:
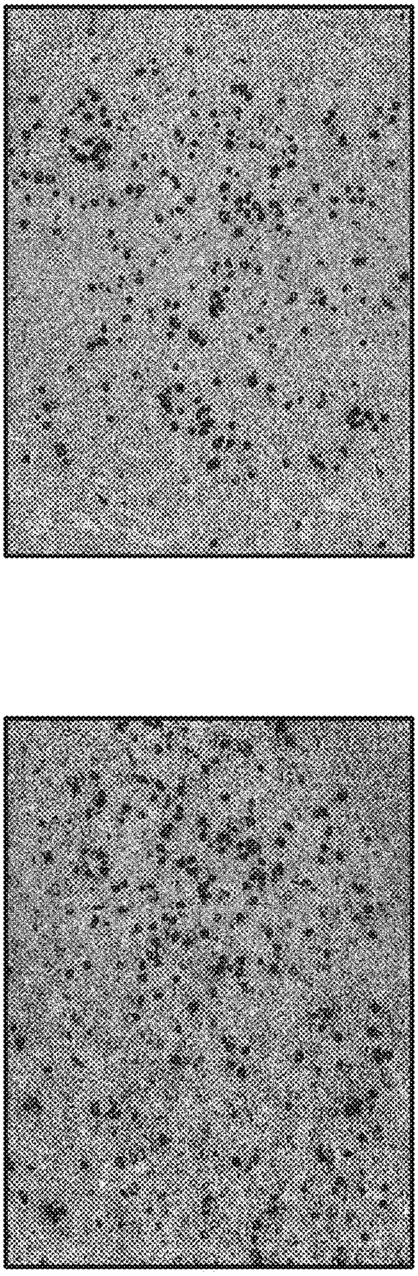
FIG. 1 illustrates staining of a sample with a coumarin-based compound conjugated to a nucleic acid probe, where the coumarin-based compound is coupled to digoxigenin ("DIG"), and where the DIG may be detected by through the application of suitable detection reagents as known in the art.

It should also be understood that, unless clearly indicated to the contrary, in any methods claimed herein that include more than one step or act, the order of the steps or acts of the method is not necessarily limited to the order in which the steps or acts of the method are recited.

As used herein, the singular terms "a," "an," and "the" include plural referents unless context clearly indicates otherwise. Similarly, the word "or" is intended to include "and" unless the context clearly indicates otherwise. The term "includes" is defined inclusively, such that "includes A or B" means including A, B, or A and B.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of" or "exactly one of." "Consisting essentially of," when used in the claims, shall have its ordinary meaning as used in the field of patent law.

The terms "comprising," "including," "having," and the like are used interchangeably and have the same meaning. Similarly, "comprises," "includes," "has," and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a device having components a, b, and c" means that the device includes at least components a, b and c. Similarly, the phrase: "a method involving steps a, b, and c" means that the method includes at least steps a, b, and c. Moreover, while the steps and processes may be outlined herein in a particular order, the skilled artisan will recognize that the ordering steps and processes may vary.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

"Analog" or "derivative" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The term "alkyl," by itself or as part of another substituent, means, unless otherwise stated, a straight (i.e., unbranched) or branched chain, or combination thereof, which may be fully saturated, mono- or polyunsaturated and can include di- and multivalent radicals, having the number of carbon atoms designated (i.e., $C_1$-$C_{10}$ means one to ten carbons). An "alkyl" is not cyclized. Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, $—CH_2CH_2CH_2CH_2—$. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or combinations thereof, consisting of at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. A heteroalkyl is not cyclized. Examples include, but are not limited to: $—CH_2—CH_2—O—CH_3$, $CH_2—CH_2—NH—CH_3$, $CH_2—CH_2—N(CH_3)—CH_3$, $CH_2—S—CH_2—CH_3$, $CH_2—CH_2$, $S(O)—CH_3$, $CH_2—CH_2—S(O)_2—CH_3$, $CH{=}CH—CH_3$, $Si(CH_3)_3$, $CH_2—CH{=}N—OCH_3$, $CH{=}CH—N(CH_3)—CH_3$, $—O—CH_3$, $—O—CH_2—CH_3$, and CN. Up to two heteroatoms may be consecutive, such as, for example, $CH_2—NH—OCH_3$.

The terms “cycloalkyl” and “heterocycloalkyl,” by themselves or in combination with other terms, mean, unless otherwise stated, cyclic versions of “alkyl” and “heteroalkyl,” respectively. Cycloalkyl and heterocycloalkyl are not aromatic.

Each of the above terms (e.g., “alkyl,” “heteroalkyl,” “cycloalkyl,” etc.) includes both substituted and unsubstituted forms of the indicated radical.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R—SR', -halogen, —SiR'R"R'", —OC(O)R', —C(O)R', $—CO_2R'$, —CONR'R", —OC(O)NR'R", —NR"C(O)R', —NR'—C(O)NR"R'", $—NR"C(O)_2R'$, —NR—C(NR'R"R')=NR"", —NR—C(NR'R")=NR', —S(O)R', $—S(O)_2R'$, $—S(O)_2NR'R"$, $—NRSO_2R'$, —CN, and $—NO_2$ in a number ranging from zero to (2m'+1), where m' is the total number of carbon atoms in such radical. R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy, or thioalkoxy groups, or arylalkyl groups. When a compound of the invention includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term “alkyl” is meant to include groups including carbon atoms bound to groups other than hydrogen groups, such as haloalkyl (e.g., $—CF_3$ and $—CH_2CF_3$) and acyl (e.g., $—C(O)CH_3$, $—C(O)CF_3$, $—C(O)CH_2OCH_3$, and the like).

As used herein, the term “antibody” refers to immunoglobulins or immunoglobulin-like molecules, including by way of example and without limitation, IgA, IgD, IgE, IgG and IgM, combinations thereof, and similar molecules produced during an immune response in any vertebrate, (e.g., in mammals such as humans, goats, rabbits and mice) and antibody fragments that specifically bind to a molecule of interest (or a group of highly similar molecules of interest) to the substantial exclusion of binding to other molecules. Antibody further refers to a polypeptide ligand comprising at least a light chain or heavy chain immunoglobulin variable region which specifically recognizes and binds an epitope of an antigen. Antibodies may be composed of a heavy and a light chain, each of which has a variable region, termed the variable heavy (VH) region and the variable light (VL) region. Together, the VH region and the VL region are responsible for binding the antigen recognized by the antibody. The term antibody also includes intact immunoglobulins and the variants and portions of them well known in the art.

As used herein, the term “biological sample,” “tissue sample,” “specimen” or the like refers to any sample including a biomolecule (such as a protein, a peptide, a nucleic acid, a lipid, a carbohydrate, or a combination thereof) that is obtained from any organism including viruses. Other examples of organisms include mammals (such as humans; veterinary animals like cats, dogs, horses, cattle, and swine; and laboratory animals like mice, rats and primates), insects, annelids, arachnids, marsupials, reptiles, amphibians, bacteria, and fungi. Biological samples include tissue samples (such as tissue sections and needle biopsies of tissue), cell samples (such as cytological smears such as Pap smears or blood smears or samples of cells obtained by microdissection), or cell fractions, fragments or organelles (such as obtained by lysing cells and separating their components by centrifugation or otherwise). Other examples of biological samples include blood, serum, urine, semen, fecal matter, cerebrospinal fluid, interstitial fluid, mucous, tears, sweat, pus, biopsied tissue (for example, obtained by a surgical biopsy or a needle biopsy), nipple aspirates, cerumen, milk, vaginal fluid, saliva, swabs (such as buccal swabs), or any material containing biomolecules that is derived from a first biological sample. In certain embodiments, the term “biological sample” as used herein refers to a sample (such as a homogenized or liquefied sample) prepared from a tumor or a portion thereof obtained from a subject.

As used herein, the term “conjugate” refers to two or more molecules or moieties (including macromolecules or supramolecular molecules) that are covalently linked into a larger construct. In some embodiments, a conjugate includes one or more biomolecules (such as peptides, proteins, enzymes, sugars, polysaccharides, lipids, glycoproteins, and lipoproteins) covalently linked to one or more other molecules moieties.

The term “coumarin” as used herein refers to fluorescent derivatization agents. As used herein, coumarin includes its derivatives such as, for example, halo-substituted coumarins (e.g. Chlorocoumarin, fluorocoumarin, bromocoumarin and its derivatives), hydroxycoumarin and its derivatives including umbelliferone and its derivatives, cyanocoumarin and its derivatives, methylcoumarin and its derivatives, ethoxycoumarin and its derivatives, benzocoumarin and its derivatives, phenylcoumarin and its derivatives, acetylcoumarin and its derivatives, and carboxylated derivatives and succinimidyl esters thereof. The aforementioned derivatives are non-limiting and are merely provided as examples.

As used herein, the terms “couple” or “coupling” refers to the joining, bonding (e.g. covalent bonding), or linking of one molecule or atom to another molecule or atom.

The terms “halo” or “halogen,” by themselves or as part of another substituent, mean, unless otherwise stated, a fluorine, chlorine, bromine, or iodine atom. Additionally, terms such as “haloalkyl” are meant to include monohaloalkyl and polyhaloalkyl. For example, the term “halo($C_1$-$C_4$) alkyl” includes, but is not limited to, fluoromethyl, difluoromethyl, trifluoromethyl, 2,2,2-trifluoroethyl, 4-chlorobutyl, 3-bromopropyl, and the like.

As used herein, “haptens” are small molecules that can combine specifically with an antibody, but typically are substantially incapable of being immunogenic except in combination with a carrier molecule.

As used herein, the terms "heteroatom" or "ring heteroatom" are meant to include boron (B), oxygen (O), nitrogen (N), sulfur (S), phosphorus (P), and silicon (Si).

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

As used herein, the term "primary antibody" refers to an antibody which binds specifically to the target protein antigen in a tissue sample. A primary antibody is generally the first antibody used in an immunohistochemical procedure.

The term "reactive group" or "reactive functional group" as used herein means a functional group that is capable of chemically reacting with a functional group of a different moiety to form a covalent linkage.

As used herein, the term "secondary antibody" herein refers to an antibody which binds specifically to a primary antibody, thereby forming a bridge between the primary antibody and a subsequent reagent (e.g. a label, an enzyme, etc.), if any. The secondary antibody is generally the second antibody used in an immunohistochemical procedure.

As used herein, the term "specific binding entity" refers to a member of a specific-binding pair. Specific binding pairs are pairs of molecules that are characterized in that they bind each other to the substantial exclusion of binding to other molecules (for example, specific binding pairs can have a binding constant that is at least 10^3 M−1 greater, 10^4 M−1 greater or 10^5 M−1 greater than a binding constant for either of the two members of the binding pair with other molecules in a biological sample). Particular examples of specific binding moieties include specific binding proteins (for example, antibodies, lectins, avidins such as streptavidins, and protein A). Specific binding moieties can also include the molecules (or portions thereof) that are specifically bound by such specific binding proteins.

As used herein, the terms "stain," "staining," or the like as used herein generally refer to any treatment of a biological specimen that detects and/or differentiates the presence, location, and/or amount (such as concentration) of a particular molecule (such as a lipid, protein or nucleic acid) or particular structure (such as a normal or malignant cell, cytosol, nucleus, Golgi apparatus, or cytoskeleton) in the biological specimen. For example, staining can provide contrast between a particular molecule or a particular cellular structure and surrounding portions of a biological specimen, and the intensity of the staining can provide a measure of the amount of a particular molecule in the specimen. Staining can be used to aid in the viewing of molecules, cellular structures and organisms not only with bright-field microscopes, but also with other viewing tools, such as phase contrast microscopes, electron microscopes, and fluorescence microscopes. Some staining performed by the system can be used to visualize an outline of a cell. Other staining performed by the system may rely on certain cell components (such as molecules or structures) being stained without or with relatively little staining other cell components. Examples of types of staining methods performed by the system include, without limitation, histochemical methods, immunohistochemical methods, and other methods based on reactions between molecules (including non-covalent binding interactions), such as hybridization reactions between nucleic acid molecules. Particular staining methods include, but are not limited to, primary staining methods (e.g., H&E staining, Pap staining, etc.), enzyme-linked immunohistochemical methods, and in situ RNA and DNA hybridization methods, such as fluorescence in situ hybridization (FISH).

As used herein, the term "target" refers to any molecule for which the presence, location and/or concentration is or can be determined. Examples of target molecules include proteins, nucleic acid sequences, and haptens, such as haptens covalently bonded to proteins. Target molecules are typically detected using one or more conjugates of a specific binding molecule and a detectable label.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The headings provide herein are for convenience only and do not interpret the scope or meaning of the disclosed embodiments.

Coumarin-Based Reagents

As described in further detail herein, the present disclosure provides novel coumarin-based reagents, e.g. linkers, and conjugates including one or more of the disclosed coumarin-based reagents. In some embodiments, the presence of a coumarin moiety within the coumarin-based reagents enables detection of labels which are typically difficult to detect, e.g. certain haptens. In some embodiments, difficult to detect haptens include benzofuran haptens and thiazolesulfonamide haptens. In some embodiments, difficult to detect haptens include 5-nitro-3-pyrazolecarbamide (NP), 2-acetamido-4-methyl-5-thiazolesulfonamide (TS), 7-(diethylamino)-2-oxo-2H-chromene-3-carboxylic acid (DCC), and 2,1,3-benzoxadiazole-5-carbamide (BF). It is believed that antibody denaturing and/or aggregation generally causes background UV/VIS absorptions in the range analyzed for these difficult to detect labels. As a result, conjugates with difficult to detect hapten labels are commonly over estimated in hapten loading which leads to underestimation of conjugate concentration. Use of the coumarin-based reagents disclosed herein is believed to alleviate this issue.

In some embodiments, the coumarin-based reagents of the present disclosure have an extinction coefficient of at least 10,000 M−1 cm−1. In other embodiments, the coumarin-based reagents of the present disclosure have an extinction coefficient of at least 15,000 M−1 cm−1. In yet other embodiments, the coumarin-based reagents of the present disclosure have an extinction coefficient of at least 20,000 M−1 cm−1. In further embodiments, the coumarin-based reagents of the present disclosure have an extinction coefficient of at least 25,000 M−1 cm−1. In some embodiments, the coumarin based compounds of the present disclosure have an absorbance wavelength of between about 340 nm to about 500 nm.

In some embodiments, the coumarin-based reagents of the present disclosure have the structure of Formulas (IA) or (IB):

$$A-[L^1]_m-W-[L^2]_n-B, \quad \text{(IA)}$$

$$A-[L^1]_m-\underset{\substack{|\\ W}}{Z}-[L^2]_n-B, \quad \text{(IB)}$$

wherein

A and B are independently a reactive functional group, a detectable label, or an enzyme reactive moiety;

$L^1$ and $L^2$ are linkers;

W includes a substituted or unsubstituted coumarin moiety or a moiety which is a substituted or an unsubstituted derivative or analog of coumarin;

Z is a bond, a —CH— group, a —CH—$CH_2$— group or a —$CH_2$—CH— group; and m and n are independently an integer ranging from 1 to 4.

In some embodiments, m and n are independently 1 or 2. In some embodiments, at least one of m or n is 1. In some embodiments, both m and n are 1. In some embodiments, one of m or n is 1 and the other of m or n is 2.

In some embodiments, both A and B are reactive functional groups. An example of such a compound is presented herein as Compound (42). Such compounds may be useful, for example, as cross-linkers, e.g. crosslinking two antibodies or proteins to each other.

Each of the groups A, B, $L^1$, $L^2$, W, m, and n are defined in further detail herein.

In some embodiments, the coumarin-based reagents of the present disclosure the structure of Formulas (IIA) or (IIB):

$$A^1-[L^1]_m-W-[L^2]_n-B^1, \quad \text{(IIA)}$$

$$A^1-[L^1]_m-\underset{\substack{|\\ W}}{Z}-[L^2]_n-B^1, \quad \text{(IIB)}$$

wherein $A^1$ is a reactive functional group;

$B^1$ is a detectable label;

$L^1$ and $L^2$ are linkers;

W includes a substituted or unsubstituted coumarin moiety or a moiety which is a substituted or an unsubstituted derivative or analog of coumarin;

Z is a bond, a —CH— group, a —CH—$CH_2$— group or a —$CH_2$—CH— group; and m and n are independently an integer ranging from 1 to 4.

In some embodiments, the detectable label is a hapten. In other embodiments, the detectable label is an enzyme. In yet other embodiments, the detectable label is a chromogen. In further embodiments, the detectable label is a fluorophore. Specific examples of each of these types of detectable labels are disclosed herein.

In some embodiments, the compounds of Formulas (IIA) and (IIB) are able to be coupled to another macromolecule, drug, or biomolecule. For example, a reactive functional group may be able to react with an amine group on a protein or an antibody to form a conjugate of the protein or antibody and the coumarin-based reagent. Other coupling methods are envisioned and disclosed herein. In some embodiments, such conjugates may be utilized as tissue labeling or staining reagents.

In some embodiments, the coumarin-based reagents of the present disclosure have the structure of Formulas (IIC) or (IID):

$$A^1-[L^1]_m-W-[L^2]_n-B^2, \quad \text{(IIC)}$$

$$A^1-[L^1]_m-W-[L^2]_n-B^2, \quad \text{(IID)}$$

wherein $A^1$ is a reactive functional group;

$B^2$ is a hapten;

$L^1$ and $L^2$ are linkers;

W includes a substituted or unsubstituted coumarin moiety or a moiety which is a substituted or an unsubstituted derivative or analog of coumarin;

Z is a bond, a —CH— group, a —CH—$CH_2$— group or a —$CH_2$—CH— group; and m and n are independently an integer ranging from 1 to 4.

In some embodiments, the hapten is an oxazole, a pyrazole, a thiazole, a benzofurazan, a triterpene, a urea, a thiourea other than a rhodamine thiourea, a nitroaryl other than dinitrophenyl or trinitrophenyl, a rotenoid, a cyclolignan, a heterobiaryl, an azoaryl, a benzodiazepine. In other embodiments, the hapten is a benzofurazan or a thiazolesulfonamide. In some embodiments, the hapten is 5-nitro-3-pyrazolecarbamide, 2-acetamido-4-methyl-5-thiazolesulfonamide, 7-(diethylamino)-2-oxo-2H-chromene-3-carboxylic acid, and 2,1,3-benzoxadiazole-5-carbamide. Other suitable haptens are disclosed herein. In some embodiments, $A^1$ includes a maleimide moiety, or an NHS-ester group. In some embodiments, at least one of $L^1$ or $L^2$ includes a lysine moiety. In some embodiments, at least one of $L^1$ or $L^2$ includes at least one dPEG group.

Non-limiting examples of compounds having Formulas (IIC) or (IID) are presented herein as Compounds (16), (24), (34), (54), and (66).

In some embodiments, the compounds of Formulas (IIC) and (IID) are able to be coupled to another macromolecule, drug, or biomolecule. For example, a reactive functional group may be able to react with an amine group on a protein or an antibody to form a conjugate of the protein or antibody and the coumarin-based reagent. Such conjugates may be utilized as tissue labeling or staining reagents.

In some embodiments, the coumarin-based reagents of the present disclosure have the structure of Formulas (IIIA) or (IIIB):

$$A^2-[L^1]_m-W-[L^2]_n-B^1, \quad \text{(IIIA)}$$

$$A^2-[L^1]_m-\underset{\substack{|\\ W}}{Z}-[L^2]_n-B^1, \quad \text{(IIIB)}$$

wherein $A^2$ is an enzyme reactive moiety;

$B^1$ is a detectable label;

$L^1$ and $L^2$ are linkers;

W includes a substituted or unsubstituted coumarin moiety or a moiety which is a substituted or an unsubstituted derivative or analog of coumarin;

Z is a bond, a —CH— group, a —CH—$CH_2$— group or a —$CH_2$—CH— group; and m and n are independently an integer ranging from 1 to 4.

Each of the enzyme reactive moieties (including tyramide moieties, moieties which are derivatives of tyramide moieties, and quinone methide precursor moieties), detectable labels, $L^1$, $L^2$, W, Z, m, and n are described in further detail herein.

In some embodiments, $A^2$ is a tyramide moiety or a moiety including a tyramide derivative as described herein. In other embodiments, $A^2$ is a quinone methide precursor moiety as described herein. In some embodiments, B1 is a hapten. In some embodiments, the hapten is an oxazole, a pyrazole, a thiazole, a benzofurazan, a triterpene, a urea, a thiourea other than a rhodamine thiourea, a nitroaryl other than dinitrophenyl or trinitrophenyl, a rotenoid, a cyclolignan, a heterobiaryl, an azoaryl, a benzodiazepine. In other embodiments, B1 is a chromogen. In yet other embodiments, B1 is a fluorophore. In some embodiments, at least one of $L^1$ or $L^2$ includes a lysine moiety. In some embodiments, at least one of $L^1$ or L2 includes at least one dPEG group.

In some embodiments, the compounds of Formulas (IIIA) and (IIIB) are suitable for use in detecting targets in a biological sample that have been labeled with an enzyme, e.g. a phosphatase or a peroxidase. Such detection processes, which may be adapted for use with the presently disclosed reagents, are described in US Patent Publication No. 2017/0089911, the disclosure of which is hereby incorporated by reference herein in its entirety.

In some embodiments, the coumarin-based reagents of the present disclosure have the structure of Formulas (IIIC) or (IIID):

(IIIC)

$$A^2-[L^1]_m-W-[L^2]_n-B^2,$$

(IIID)

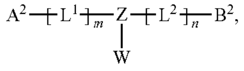

wherein $A^2$ is an enzyme reactive moiety;

$B^2$ is a hapten;

$L^1$ and $L^2$ are linkers;

W includes a substituted or unsubstituted coumarin moiety or a moiety which is a substituted or an unsubstituted derivative or analog of coumarin;

Z is a bond, a —CH— group, a —CH—$CH_2$— group or a —$CH_2$—CH— group; and m and n are independently an integer ranging from 1 to 4.

As noted above, each of the enzyme reactive moieties (including tyramide moieties, moieties which are derivatives of tyramide moieties, and quinone methide precursor moieties), detectable labels, $L^1$, $L^2$, W, Z, m, and n are described in further detail herein. In some embodiments, the hapten is an oxazole, a pyrazole, a thiazole, a benzofurazan, a triterpene, a urea, a thiourea other than a rhodamine thiourea, a nitroaryl other than dinitrophenyl or trinitrophenyl, a rotenoid, a cyclolignan, a heterobiaryl, an azoaryl, a benzodiazepine. In other embodiments, the hapten is a benzofurazan or a thiazolesulfonamide. In some embodiments, the hapten is 5-nitro-3-pyrazolecarbamide, 2-acetamido-4-methyl-5-thiazolesulfonamide, 7-(diethylamino)-2-oxo-2H-chromene-3-carboxylic acid, and 2,1,3-benzoxadiazole-5-carbamide. In some embodiments, at least one of $L^1$ or $L^2$ includes a lysine moiety. In some embodiments, at least one of $L^1$ or $L^2$ includes at least one dPEG group.

Non-limiting examples of compounds having Formulas (IIIC) or (IIID) are presented herein as Compounds (17), (25), and (35).

In some embodiments, the compounds of Formulas (IIIC) and (IIID) are suitable for use in detecting targets in a biological sample that have been labeled with an enzyme, e.g. a phosphatase or a peroxidase, as described herein.

In some embodiments, the coumarin-based reagents of the present disclosure have the structure of Formulas (IIIE) or (IIIF):

(IIIE)

$$A^1-[L^1]_m-W-[L^2]_n-B^3,$$

(IIIF)

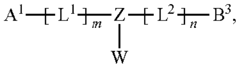

wherein $A^2$ is an enzyme reactive moiety;

$B^3$ is a reactive group capable of participating in a click-chemistry reaction;

$L^1$ and $L^2$ are linkers;

W includes a substituted or unsubstituted coumarin moiety or a moiety which is a substituted or an unsubstituted derivative or analog of coumarin;

Z is a bond, a —CH— group, a —CH—$CH_2$— group or a —$CH_2$—CH— group; and m and n are independently an integer ranging from 1 to 4.

In some embodiments, $B^3$ is a DBCO group. In other embodiments, $B^3$ is an azide group. Yet other suitable functional groups capable of participating in a click chemistry reaction are disclosed herein. In some embodiments, at least one of $L^1$ or $L^2$ includes a lysine moiety. In some embodiments, at least one of $L^1$ or $L^2$ includes at least one dPEG group.

In some embodiments, the compounds of Formulas (IIIE) and (IIIF) are suitable for use in detecting targets in a biological sample that have been labeled with an enzyme, e.g. a phosphatase or a peroxidase, including those embodiments utilizing click conjugates coupled to a reporter moiety, such as described in PCT Publication No. WO/2018/002016, the disclosure of which is hereby incorporated by reference herein in its entirety.

Substituted or Unsubstituted Coumarin Moieties, or Moieties which are a Substituted or an Unsubstituted Derivative or Analog of Coumarin In some embodiments, W has the structure of either Formula (IVA) or (IVB):

(IVA)

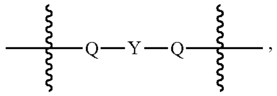

(IVB)

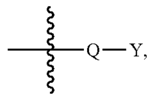

wherein Q is a bond or a substituted or unsubstituted, straight chain or branched $C_1$-$C_{16}$ alkyl group, —$[(CH_2CH_2)_j$—$O]_k$—$CH_2$—, —$[(CH_2)_j$—$O]_k$—$CH_2$—, where j is an integer ranging from 1 to 4 and k is an integer ranging from 1 to 16; —N—$R^x$—; —C(O)—N—$R^x$—; or —N—$R^x$—C(O)—, $R^x$ is H or a $C_1$-$C_4$ alkyl group; and Y is a substituted or unsubstituted coumarin moiety or a moiety which is a substituted or an unsubstituted derivative or analog of coumarin.

In some embodiments, (i) the substituted or unsubstituted coumarin moiety, or (ii) the moiety which is a substituted or an unsubstituted derivative or analog of coumarin, includes at least one group selected from a substituted or unsubstituted, straight chain or branched $C_1$-$C_6$ alkyl group; a substituted or unsubstituted, straight chain or branched $C_1$-$C_6$ alkoxy group; a substituted or unsubstituted, straight chain or branched $C_1$-$C_6$ heteroalkyl group; a trifluoromethyl group; a hydroxyl group; a sulfate group; a cyano group; a halogen; a phosphate group; a saccharide; a carboxylic acid group; a nitro group; —C(O)$NR^xR^y$; —S—$R^x$; —$SO_2$; —$SO_2Cl$; —$SO_3H$; —$SO_4H$; —$SO_2NR^xR^y$; —N(H)—$NR^xR^y$; —$NR^xR^y$; and wherein $R^x$ and $R^y$ are independently H or a $C_1$-$C_4$ alkyl group.

In some embodiments, W has the structure of either of Formula (VA) or (VB):

(VA)

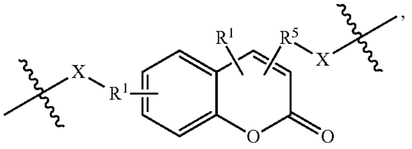

(VB)

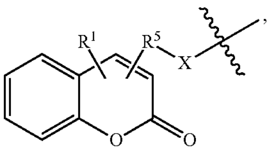

wherein the moiety of Formula (VA) may be substituted with 0, 1, 2, 3, or 4 $R^t$ groups; and wherein the compound of Formula (VB) may be substituted with 0, 1, 2, 3, 4, or 5 $R^t$ groups; and wherein each $R^t$ is independently selected from a substituted or unsubstituted, straight chain or branched $C_1$-$C_{12}$ alkyl group; a substituted or unsubstituted, straight chain or branched $C_1$-$C_{12}$ alkoxy group; a substituted or unsubstituted, straight chain or branched $C_1$-$C_{12}$ heteroalkyl group; a trifluoromethyl group; a hydroxyl group; a sulfate group; a cyano group; a halogen; a phosphate group; a saccharide; a carboxylic acid group; a nitro group; —C(O)$NR^xR^y$; —S—$R^x$; —$SO_2$; —$SO_2Cl$; —$SO_3H$; —$SO_4H$; —$SO_2NR^xR^y$; —N(H)—$NR^xR^y$; —$NR^xR^y$; and wherein $R^x$ and $R^y$ are independently H or a $C_1$-$C_6$ alkyl group;

wherein the moiety of Formula (VA) is substituted with one —$R^1$—X— group and one —$R^5$—X— group; and wherein the moiety of Formula (VB) is substituted with one —$R^5$—X— group;

$R^1$ is a $C_1$-$C_{10}$ substituted or unsubstituted, branched or unbranched alkyl group, —O—, —O—$CH_2$—, —N($R^x$)—; or —S—.

$R^5$ is a $C_1$-$C_{10}$ substituted or unsubstituted, branched or unbranched alkyl group, —C(O)—O—; —C(O)—N(H)—; and each X is independently a bond or a substituted or unsubstituted, straight chain or branched $C_1$-$C_{16}$ alkyl group; —[$(CH_2)_j$—O]$_k$—$CH_2$—, where j is an integer ranging from 1 to 4 and k is an integer ranging from 1 to 16; —N—$R^x$—; —C(O)—N—$R^x$—; or —N—$R^x$—C(O)—, where $R^x$ is H or a $C_1$-$C_4$ alkyl group.

In some embodiments, the compounds of Formula (VA) and (VB) include one $R^t$ group, which may be on either ring of the coumarin moiety. In some embodiments, the compounds of Formula (VA) and (VB) include two $R^t$ groups.

In some embodiments, $R^1$ is a $C_1$-$C_6$ branched or unbranched alkyl group. In some embodiments, $R^5$ is a $C_1$-$C_6$ branched or unbranched alkyl group.

In some embodiments, W has the structure of either Formula (VC) or (VD):

(VC)

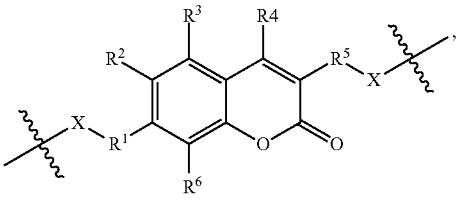

(VD)

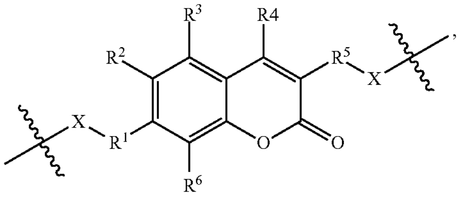

wherein $R^2$, $R^3$, $R^4$, $R^6$, and $R^7$ are independently selected from a substituted or unsubstituted, straight chain or branched $C_1$-$C_6$ alkyl group; a substituted or unsubstituted, straight chain or branched $C_1$-$C_6$ alkoxy group; a substituted or unsubstituted, straight chain or branched $C_1$-$C_6$ heteroalkyl group; a trifluoromethyl group; a hydroxyl group; a sulfate group; a cyano group; a halogen; a phosphate group; a saccharide; a carboxylic acid group; a nitro group; —C(O)$NR^xR^y$; —S—$R^x$; —$SO_2$; —$SO_2Cl$; —$SO_3H$; —$SO_4H$; —$SO_2NR^xR^y$; —N(H)—$NR^xR^y$; —$NR^xR^y$; and wherein $R^x$ and $R^y$ are independently H or a $C_1$-$C_4$ alkyl group;

$R^5$ is a $C_1$-$C_{10}$ substituted or unsubstituted, branched or unbranched alkyl group, —C(O)—O—; —C(O)—N(H)—;

$R^1$ is a $C_1$-$C_{10}$ substituted or unsubstituted, branched or unbranched alkyl group, —O—, —O—$CH_2$—, —N($R^x$)—; or —S—; and each X is independently a bond or a substituted or unsubstituted, straight chain or branched $C_1$-$C_{16}$ alkyl group; —[$(CH_2)_j$—O]—$CH_2$—, where j is an integer ranging from 1 to 4 and k is an integer ranging from 1 to 16; —N—$R^x$—; —C(O)—N—$R^x$—; or —N—$R^x$—C(O)—, where $R^x$ is H or a $C_1$-$C_4$ alkyl group.

In some embodiments, $R^1$ is a $C_1$-$C_6$ branched or unbranched alkyl group. In some embodiments, $R^5$ is a $C_1$-$C_6$ branched or unbranched alkyl group.

Linkers

In some embodiments, the groups $L^1$ and $L^2$ each independently have a molecular weight ranging from about 20 g/mol to about 3000 g/mol. In other embodiments, the groups $L^1$ and $L^2$ each independently have a molecular weight ranging from about 40 g/mol to about 2000 g/mol. In other embodiments, the groups $L^1$ and $L^2$ each independently have a molecular weight ranging from about 50 g/mol to about 1500 g/mol. In other embodiments, the groups $L^1$ and $L^2$ each independently have a molecular weight ranging from about 50 g/mol to about 1250 g/mol. In other embodiments, the groups $L^1$ and $L^2$ each independently have a molecular weight ranging from about 75 g/mol to about 1000 g/mol. In other embodiments, the groups $L^1$ and $L^2$ each independently have a molecular weight ranging from about 100 g/mol to about 800 g/mol. In other embodiments, the groups $L^1$ and $L^2$ each independently have a molecular weight ranging from about 100 g/mol to about 600 g/mol. In other embodiments, the groups $L^1$ and $L^2$ each independently have a molecular weight ranging from about 100 g/mol to about 400 g/mol. In other embodiments, the groups $L^1$ and $L^2$ each independently have a molecular weight ranging from about 100 g/mol to about 200 g/mol. In other embodiments, the groups $L^1$ and $L^2$ each independently have a molecular weight ranging from about 250 g/mol to about 500 g/mol. In other embodiments, the groups $L^1$ and $L^2$ each independently have a molecular weight ranging from about 20 g/mol to about 150 g/mol.

In some embodiments, the groups $L^1$ and $L^2$ each independently have a length ranging from between about 0.5 nm to about 150 nm. In some embodiments, the groups $L^1$ and $L^2$ each independently have a length ranging from between about 0.5 nm to about 100 nm. In some embodiments, the groups $L^1$ and $L^2$ each independently have a length ranging from between about 0.5 nm to about 50 nm. In some embodiments, the groups $L^1$ and $L^2$ each independently have a length ranging from between about 0.5 nm to about 30 nm. In other embodiments, the groups $L^1$ and $L^2$ each independently have a length which is less than about 20 nm. In yet other embodiments, the groups $L^1$ and $L^2$ each independently have a length which is less than about 15 nm.

In some embodiments, each of $L^1$ and $L^2$ may independently be charged or uncharged. In some embodiments, the groups $L^1$ and $L^2$ include one or more charged groups. For example, in some embodiments, the groups $L^1$ and $L^2$ may include one or more of quaternary amine groups, pyridinium groups, cyclic ureas, or sulphate groups.

In other embodiments, $L^1$ and $L^2$ may include a single amino acid residue (e.g. lysine), a peptide or a polymer, which may be charged or uncharged. In some embodiments, $L^1$ and $L^2$ may independently include a peptide having between 2 and 20 amino acids, a peptide having between 2 and 10 amino acids, a peptide having between 2 and 8 amino acids, or a peptide having between 1 and 4 amino acids. By way of example, the peptide may be lysine-$[U]_q$-lysine, where U represents an amino acid and where q is 0 or an integer ranging from 1 to 18. In instances where q is 1 or more, U may represent a homogeneous or heterogeneous peptide sequence, i.e. one including the same or different amino acids. In some embodiments, U is selected from lysine, alanine, arginine, guanine, glutamic acid or any combination thereof. Suitable charged polymers are described in United States Patent Publication Nos. 2002/0052335, 2004/0058446, 2004/0197318, and 2004/0162235, the disclosures of which are each hereby incorporated by reference herein in their entireties.

In some embodiments, the $L^1$ and L2 groups independently include one or more solubilizing groups. In some embodiments, the solubilizing groups include polyethylene glycol (PEG) groups (or discrete PEGS (dPEGs) available from Quanta Biodesign). In some embodiments, the $L^1$ and L2 groups independently include between about 2 and about 24 PEG groups. In some embodiments, the $L^1$ and L2 groups independently include between about 2 and about 18 PEG groups. In other embodiments, the $L^1$ and L2 groups independently include between about 2 and about 12 PEG groups. In yet other embodiments the $L^1$ and L2 groups independently include between about 2 and about 6 PEG groups. In yet other embodiments, the $L^1$ and L2 groups independently include 4 PEG groups. In yet other embodiments, the $L^1$ and L2 groups independently include 8 PEG groups. In yet other embodiments, the $L^1$ and L2 groups independently include 12 PEG groups. In yet other embodiments, the $L^1$ and L2 groups independently include 16 PEG groups. In yet other embodiments, the $L^1$ and L2 groups independently include 24 PEG groups. It is believed that the incorporation of such alkylene oxide linkers is believed to increase the hydrophilicity of the coumarin-based reagent.

In some embodiments, each $L^1$ and $L^2$ is independently a branched or unbranched, linear or cyclic, substituted or unsubstituted, saturated or unsaturated, group having between 2 and 200 carbon atoms, and optionally having one or more heteroatoms selected from O, N, or S. In other embodiments, each $L^1$ and $L^2$ is independently a branched or unbranched, linear or cyclic, substituted or unsubstituted, saturated or unsaturated, group having between 2 and 120 carbon atoms, and optionally having one or more heteroatoms selected from O, N, or S. In yet other embodiments, each $L^1$ and $L^2$ is independently a branched or unbranched, linear or cyclic, substituted or unsubstituted, saturated or unsaturated, group having between 2 and 80 carbon atoms, and optionally having one or more heteroatoms selected from O, N, or S. In some embodiments, each $L^1$ and $L^2$ is independently a branched or unbranched, linear or cyclic, substituted or unsubstituted, saturated or unsaturated, group having between 4 and 40 carbon atoms, and optionally having one or more heteroatoms selected from O, N, or S. In some embodiments, each $L^1$ and $L^2$ is independently a branched or unbranched, linear or cyclic, substituted or unsubstituted, saturated or unsaturated, group having between 6 and 20 carbon atoms, and optionally having one or more heteroatoms selected from O, N, or S.

In some embodiments, each $L^1$ and/or $L^2$ group independently has the Formula (VIA):

(VIA)

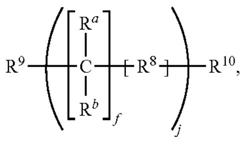

wherein f is 0 or an integer ranging from 1 to 24;

j is an integer ranging from 1 to 24;

$R^1$ is a bond or O, S, —$N(R^c)(R^d)$, or —$N^+(R^c)(R^d)(R^e)$;

$R^a$ and $R^b$ are independently H, a $C_1$-$C_4$ alkyl group, F, Cl, or —$N(R^c)(R^d)$;

$R^c$, $R^d$, and $R^e$ are independently selected from H or a $C_1$-$C_4$ alkyl group;

$R^9$ and $R^{10}$ are independently a bond or a group having up to 6 carbon atoms and including a carbonyl, an amide, an imide, an ester, an ether, an amine, an thione, or a thiol.

In some embodiments, at least one of $R^a$ or $R^b$ is H. In some embodiments, at least one of $R^a$ or $R^b$ is H and f is 1 or 2. In some embodiments, at least one of $R^a$ or $R^b$ is H, f is 1 and s is at least 2. In some embodiments, $R^a$ and $R^b$ are H and $R^8$ is a bond. In some embodiments, the linkers of Formula (VIA) include between 2 and 40 carbon atoms. In some embodiments, the linkers of Formula (VIA) include between 4 and 20 carbon atoms. In some embodiments, the groups $L^1$ and $L^2$ each independently have a molecular weight ranging from about 100 g/mol to about 600 g/mol. In some embodiments, the groups $L^1$ and $L^2$ each independently have a molecular weight ranging from about 100 g/mol to about 400 g/mol. In some embodiments, the groups $L^1$ and $L^2$ each independently have a molecular weight ranging from about 100 g/mol to about 200 g/mol.

In some embodiments, each $L^1$ and $L^2$ group independently has Formula (VIB):

$$R^9—((CH_2)_f(R^8))_j—R^{10}, \quad \text{(VIB)}$$

wherein f is or an integer ranging from 1 to 12;

$R^8$ is a bond or O, S, —$N(R^c)(R^d)$, or —$N^+(R^c)(R^d)(R^e)$;

$R^c$, $R^d$, and $R^e$ are independently $CH_3$ or H;

$R^9$ and $R^{10}$ are independently a bond or a group selected from carbonyl, amide, imide, ester, ether, amine, or thiol; and j is an integer ranging from 1 to 24.

In some embodiments, f is 1 and s is at least 2. In some embodiments, $R^8$ is a bond; f is 1; and j is 2 to 16. In other embodiments, $R^8$ is a bond; f is 1; and j is 2 to 12. In other embodiments, $R^8$ is a bond; f is 1; and j is 2 to 8.

In some embodiments, the linkers of Formula (VIB) include between 2 and 40 carbon atoms. In some embodiments, the linkers of Formula (VIB) include between 4 and 20 carbon atoms. In some embodiments, the groups $L^1$ and $L^2$ each independently have a molecular weight ranging from about 100 g/mol to about 600 g/mol. In some embodiments, the groups $L^1$ and $L^2$ each independently have a molecular weight ranging from about 100 g/mol to about 400 g/mol. In some embodiments, the groups $L^1$ and $L^2$ each independently have a molecular weight ranging from about 100 g/mol to about 200 g/mol.

In some embodiments, each $L^1$ and $L^2$ group independently has Formula (VIC):

$$R^9—((CH_2)_f(O))_j—R^{10}, \quad \text{(VIC)}$$

wherein f is 0 or an integer ranging from 1 to 12;

j is an integer ranging from 1 to 24; and $R^9$ and $R^{10}$ are independently a bond or a group selected from carbonyl, amide, imide, ester, ether, amine, or thiol.

In some embodiments, f is 1; and j is at least 2. In some embodiments, f is 1 and j is 2. In some embodiments, f is 1 and j is 3. In some embodiments, f is 1 and j is 4. In some embodiments, f is 2 and j is an integer ranging from 2 to 16. In some embodiments, f is 2 and j is an integer ranging from 2 to 12. In some embodiments, f is 2 and j is an integer ranging from 2 to 8. In some embodiments, f is 2 and j is at least 2. In some embodiments, f is 2 and j is at least 3. In some embodiments, f is 2 and j is at least 4.

The skilled artisan will appreciate that when m and n of Formulas (IA) and/or (IIB) are greater than 1, multiple $L^1$ or $L^2$ groups accordingly may be joined, and that each $L^1$ or $L^2$ group may be the same different. By way of example, where m is 2, each $L^1$ of the group -[$L^1$]-[$L^1$]-may be the same or different. For example, one $L^1$ of the group -[$L^1$]-[$L^1$]-may include a repeating alkylene oxide group, while the other $L^1$ of the group may include an unsubstituted $C_1$-$C_{10}$ alkyl group. By way of another example, one $L^1$ of the group -[$L^1$]-[$L^1$]-may include at least one PEG or dPEG group, while the other $L^1$ of the group -[$L^1$]-[$L^1$]-may include a lysine residue. By way of yet another example, one $L^1$ of the group may include at least one PEG or dPEG group, while the other $L^1$ of the group -[$L^1$]-[$L^1$]-may include a lysine residue, and an L2 group may include at least one PEG or dPEG group.

Reactive Functional Groups

In general, a reactive functional group may be any group that facilitates the coupling of two molecule together to form an adduct. In some embodiments, the reactive functional group is one that is capable of participating in nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

In some embodiments, the reactive functional group is a carboxylic acid, an activated ester of a carboxylic acid, a carbodiimide, a sulfonyl halide, an acyl halide, a silyl halide, an acyl azide, an acyl nitrile, an acrylamide, an amine, an aldehyde, an alkyl halide (wherein the halide can be later displaced with a nucleophilic group such as, for example, an amine, a carboxylate anion, thiol anion, carbanion, or an alkoxide ion, thereby resulting in the covalent attachment of a new group at the site of the halogen atom), an aryl halide, an alkyl sulfonate, a sulfonate ester, an anhydride, an azide, an aziridine, a diazoalkane, an haloacetamide, an halotriazine, an hydrazine, an hydroxylamine, an isocyanate, an isothiocyanate, a maleimide, a phosphoramidate, a thiol (which, in some embodiments, can be converted to disulfides, reacted with acyl halides, or bonded to metals), an hydroxyl (which can be converted to esters, ethers, aldehydes, etc.), an hydrazine and an alkyne (which can undergo, for example, cycloadditions, acylation, Michael addition). In some embodiments, the reactive functional group is a carboxyl group or the various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters. In some embodiments, the reactive functional groups are dienophile groups which are capable of participating in Diels-Alder reactions such as, for example, maleimide groups. In some embodiments, the reactive functional groups are aldehyde or ketone groups such that subsequent derivatization is possible via formation of carbonyl derivatives such as, for example, imines, hydrazones, semicarbazones or oximes, or via such mechanisms as Grignard addition or alkyl lithium addition.

In other embodiments, the reactive functional group is selected from carboxylic acid, an activated ester of a carboxylic acid, sulfonyl halide, acyl halide, amine, alkyl or aryl halide, anhydride, azide, haloacetamide, halotriazine, hydrazine, isocyanate, isothiocyanate, maleimide, phosphoramidate, thiol, hydroxyl and alkyne. In yet other embodiments, the reactive functional group is selected from carboxylic acid, an activated ester of a carboxylic acid, amine, azide, haloacetamide, hydrazine, isocyanate, maleimide and alkyne.

In some embodiments, the reactive functional groups can be chosen such that they do not participate in, or interfere with, the chemical stability of the conjugate described herein. Alternatively, a reactive functional group can be protected from participating in the crosslinking reaction by the presence of a protecting group.

In some embodiments, the reactive functional group is a moiety capable of undergoing a "click chemistry" reaction. "Click chemistry" is a chemical philosophy, independently defined by the groups of Sharpless and Meldal, that describes chemistry tailored to generate substances quickly and reliably by joining small units together. "Click chemistry" has been applied to a collection of reliable and self-directed organic reactions (Kolb, H. C.; Finn, M. G.; Sharpless, K. B. Angew). Chem. Int. Ed. 2001, 40, 2004-2021). For example, the identification of the copper catalyzed azide-alkyne [3+2] cycloaddition as a highly reliable molecular connection in water (Rostovtsev, V. V.; et al. Angew. Chem. Int. Ed. 2002, 41, 2596-2599) has been used to augment several types of investigations of biomolecular interactions (Wang, Q.; et al. J. Am. Chem. Soc. 2003, 125, 3192-3193; Speers, A. E.; et al. J. Am. Chem. Soc. 2003, 125, 4686-4687; Link, A. J.; Tirrell, D. A. J. Am. Chem. Soc. 2003, 125, 11164-11165; Deiters, A.; et al. J. Am. Chem. Soc. 2003, 125, 11782-11783). In addition, applications to organic synthesis (Lee, L. V.; et al. J. Am. Chem. Soc. 2003, 125, 9588-9589), drug discovery (Kolb, H. C.; Sharpless, K. B. Drug Disc. Today 2003, 8, 1128-1137; Lewis, W. G.; et al. Angew. Chem. Int. Ed. 2002, 41, 1053-1057), and the functionalization of surfaces (Meng, J.-C.; et al. Angew. Chem. Int. Ed. 2004, 43, 1255-1260; Fazio, F.; et al. J. Am. Chem. Soc. 2002, 124, 14397-14402; Collman, J. P.; et al. Langmuir 2004, ASAP, in press; Lummerstorfer, T.; Hoffmann, H. J. Phys. Chem. B 2004, in press) have also appeared. Generally, click chemistry encourages reactions that have modular applications that are wide in scope, that have a high chemical yield, that generate inoffensive byproducts, that are chemospecific, that require simple reaction conditions, that use readily available starting materials and reagents, that are solvent free or use benign solvents (such as water), that lead to easy product isolation, that have a large thermodynamic driving force to favor a reaction with a single reaction product, and/or that have a high atom economy. While certain of the general criteria can be subjective in nature, and not all criteria need to be met.

The skilled artisan will appreciate that any of the compounds of Formulas (IA), (IB), (IIIE), (IIIF) may terminate in an appropriate reactive group (e.g. a DBCO group) that may form a click adduct with another appropriately functionalized compound (e.g. a compound having an azide group) (including those described in PCT Publication WO/2018/002015, the disclosure of which is hereby incorporated by reference herein in its entirety). Pairs of reactive groups capable of reacting in a click chemistry reaction are set forth in the table which follows:

| Reactive Functional Group on a First Member of a Pair of Click Conjugates | Reactive Functional Group on a Second Member of a Pair of Click Conjugates |
|---|---|
| DBCO | Azide |
| Alkene | Tetrazine |
| TCO | Tetrazine |
| Maleimide | Thiol |
| DBCO | 1,3-Nitrone |
| Aldehyde or ketone | Hydrazine |
| Aldehyde or ketone | Hydroxylamine |
| Azide | DBCO |
| Tetrazine | TCO |
| Thiol | Maleimide |
| 1,3-Nitrone | DBCO |
| Hydrazine | Aldehyde or ketone |
| Hydroxylamine | Aldehyde or ketone |
| Tetrazine | Alkene |

Detectable Labels

In general, detectable labels include chromogenic, fluorescent, phosphorescent and luminescent molecules and materials, catalysts (such as enzymes) that convert one substance into another substance to provide a detectable difference (such as by converting a colorless substance into a colored substance or vice versa, or by producing a precipitate or increasing sample turbidity), haptens that can be detected through antibody-hapten binding interactions using additional detectably labeled antibody conjugates, and paramagnetic and magnetic molecules or materials. Of course, the reporter moieties can themselves also be detected indirectly, e.g. if the detectable label is a hapten, then yet another antibody specific to that detectable label may be utilized in the detection of the detectable label, as known to those of ordinary skill in the art.

In some embodiments, suitable haptens include, but are not limited to, pyrazoles (e.g. nitropyrazoles); nitrophenyl compounds; benzofurazans; triterpenes; ureas (e.g. phenyl ureas); thioureas (e.g. phenyl thioureas); rotenone and rotenone derivatives; oxazole (e.g. oxazole sulfonamides); thiazoles (e.g. thiazole sulfonamides); coumarin and coumarin derivatives; and cyclolignans. Additional non-limiting examples of haptens include thiazoles; nitroaryls; benzofurans; triperpenes; and cyclolignans. Specific examples of haptens include di-nitrophenyl, biotin, digoxigenin, and fluorescein, and any derivatives or analogs thereof. Other suitable haptens are described in U.S. Pat. Nos. 8,846,320; 8,618,265; 7,695,929; 8,481,270; and 9,017,954, the disclosures of which are incorporated herein by reference in their entirety. Other suitable haptens are described in United States Publication Nos. 2013/0109019 and 2010/0184087, the disclosures of which are incorporated herein by reference in their entireties.

In some embodiments, suitable fluorophores belong to several common chemical classes including coumarins, fluoresceins (or fluorescein derivatives and analogs), rhodamines, resorufins, luminophores and cyanines. Additional examples of fluorescent molecules can be found in Molecular Probes Handbook—A Guide to Fluorescent Probes and Labeling Technologies, Molecular Probes, Eugene, OR, TheroFisher Scientific, 11th Edition. In other embodiments, the fluorophore is selected from xanthene derivatives, cyanine derivatives, squaraine derivatives, naphthalene derivatives, coumarin derivatives, oxadiazole derivatives, anthracene derivatives, pyrene derivatives, oxazine derivatives, acridine derivatives, arylmethine derivatives, and tetrapyrrole derivatives. In other embodiments, the fluorescent moiety is selected from a CF dye (available from Biotium), DRAQ and CyTRAK probes (available from BioStatus), BODIPY (available from Invitrogen), Alexa Fluor (available from Invitrogen), DyLight Fluor (e.g. DyLight 649) (available from Thermo Scientific, Pierce), Atto and Tracy (available from Sigma Aldrich), FluoProbes (available from Interchim), Abberior Dyes (available from Abberior), DY and MegaStokes Dyes (available from Dyomics), Sulfo Cy dyes (available from Cyandye), HiLyte Fluor (available from AnaSpec), Seta, SeTau and Square Dyes (available from SETA BioMedicals), Quasar and Cal Fluor dyes (available from Biosearch Technologies), SureLight Dyes (available from APC, RPEPerCP, Phycobilisomes)(Columbia Biosciences), and APC, APCXL, RPE, BPE (available from Phyco-Biotech, Greensea, Prozyme, Flogen).

In some embodiments, suitable enzymes include, but are not limited to, horseradish peroxidase, alkaline phosphatase, acid phosphatase, glucose oxidase, β-galactosidase, β-glucuronidase or β-lactamase. In other embodiments, enzymes include oxidoreductases or peroxidases (e.g. HRP, AP). In these embodiments, the enzyme conjugated to the anti-label antibody catalyzes conversion of a chromogenic substrate to a reactive moiety which covalently binds to a sample proximal to or directly on the target.

Particular non-limiting examples of chromogenic compounds/substrates include diaminobenzidine (DAB), 4-nitrophenylphospate (pNPP), fast red, bromochloroindolyl phosphate (BCIP), nitro blue tetrazolium (NBT), BCIP/NBT, fast red, AP Orange, AP blue, tetramethylbenzidine (TMB), 2,2'-azino-di-[3-ethylbenzothiazoline sulphonate] (ABTS), o-dianisidine, 4-chloronaphthol (4-CN), nitrophenyl-β-D-galactopyranoside (ONPG), o-phenylenediamine (OPD), 5-bromo-4-chloro-3-indolyl-β-galactopyranoside (X-Gal), methylumbelliferyl-β-D-galactopyranoside (MU-Gal), p-nitrophenyl-α-D-galactopyranoside (PNP), 5-bromo-4-chloro-3-indolyl-β-D-glucuronide (X-Gluc), 3-amino-9-ethyl carbazol (AEC), fuchsin, iodonitrotetrazolium (INT), tetrazolium blue, tetrazolium violet, N,N'-bis-carboxypentyl-5,5'-disulfonato-indo-dicarbocyanine (Cy5), 4-(dimethylamino) azobenzene-4'-sulfonamide (DABSYL), tetramethylrhodamine (DISCO Purple), and Rhodamine 110 (Rhodamine). DAB, which is oxidized in the presence of peroxidase and hydrogen peroxide, results in the deposition of a brown, alcohol-insoluble precipitate at the site of enzymatic activity. In some embodiments, the chromogenic substrates are signaling conjugates which comprise a latent reactive moiety and a chromogenic moiety.

In some embodiments, the latent reactive moiety of the signaling conjugate is configured to undergo catalytic activation to form a reactive species that can covalently bond with the sample or to other detection components. The catalytic activation is driven by one or more enzymes (e.g., oxidoreductase enzymes and peroxidase enzymes, like horseradish peroxidase) and results in the formation of a reactive species. These reactive species are capable of reacting with the chromogenic moiety proximal to their generation, i.e. near the enzyme. Specific examples of signaling conjugates are disclosed in US Patent Publication No. 2013/0260379, the disclosure of which is hereby incorporated by reference herein in its entirety.

Other suitable detectable labels are described in PCT Publication WO/2018/002015, the disclosure of which is hereby incorporated by reference herein in its entirety. For example, suitable labels include multi-dye conjugate having at least two chromophores coupled directly or indirectly to each other.

Yet other examples of detectable labels include, but are not limited to, DAB; AEC; CN; BCIP/NBT; fast red; fast blue; fuchsin; NBT; ALK GOLD; Cascade Blue acetyl azide; Dapoxylsulfonic acid/carboxylic acid succinimidyl ester; DY-405; Alexa Fluor 405 succinimidyl ester; Cascade Yellow succinimidyl ester; pyridyloxazole succinimidyl ester (PyMPO); Pacific Blue succinimidyl ester; DY-415; 7-hydroxycoumarin-3-carboxylic acid succinimidyl ester; DYQ-425; 6-FAM phosphoramidite; *Lucifer* Yellow; iodoacetamide; Alexa Fluor 430 succinimidyl ester; Dabcyl succinimidyl ester; NBD chloride/fluoride; QSY 35 succinimidyl ester; DY-485XL; Cy2 succinimidyl ester; DY-490; Oregon Green 488 carboxylic acid succinimidyl ester; Alexa Fluor 488 succinimidyl ester; BODIPY 493/503 C3 succinimidyl ester; DY-480XL; BODIPY FL C3 succinimidyl ester; BODIPY FL C5 succinimidyl ester; BODIPY FL-X succinimidyl ester; DYQ-505; Oregon Green 514 carboxylic acid succinimidyl ester; DY-510XL; DY-481XL; 6-carboxy-4',5'-dichloro-2',7'-dimethoxyfluorescein succinimidyl ester (JOE); DY-520XL; DY-521XL; BODIPY R6G C3 succinimidyl ester; erythrosin isothiocyanate; 5-carboxy-2',4',5',7'-tetrabromosulfonefluorescein succinimidyl ester; Alexa Fluor 532 succinimidyl ester; 6-carboxy-2',4,4',5'7,7'-hexachlorofluorescein succinimidyl ester (HEX); BODIPY 530/550 C3 succinimidyl ester; DY-530; BODIPY TMR-X succinimidyl ester; DY-555; DYQ-1; DY-556; Cy3 succinimidyl ester; DY-547; DY-549; DY-550; Alexa Fluor 555 succinimidyl ester; Alexa Fluor 546 succinimidyl ester; DY-548; BODIPY 558/568 C3 succinimidyl ester; Rhodamine red-X succinimidyl ester; QSY 7 succinimidyl ester; BODIPY 564/570 C3 succinimidyl ester; BODIPY 576/589 C3 succinimidyl ester; carboxy-X-rhodamine (ROX); succinimidyl ester; Alexa Fluor 568 succinimidyl ester; DY-590; BODIPY 581/591 C3 succinimidyl ester; DY-591; BODIPY TR-X succinimidyl ester; Alexa Fluor 594 succinimidyl ester; DY-594; carboxynaphthofluorescein succinimidyl ester; DY-605; DY-610; Alexa Fluor 610 succinimidyl ester; DY-615; BODIPY 630/650-X succinimidyl ester; erioglaucine; Alexa Fluor 633 succinimidyl ester; Alexa Fluor 635 succinimidyl ester,; DY-634; DY-630; DY-631; DY-632; DY-633; DYQ-2; DY-636; BODIPY 650/665-X succinimidyl ester; DY-635; Cy5 succinimidyl ester; Alexa Fluor 647 succinimidyl ester; DY-647; DY-648; DY-650; DY-654; DY-652; DY-649; DY-651; DYQ-660; DYQ-661; Alexa Fluor 660 succinimidyl ester; Cy5.5 succinimidyl ester; DY-677; DY-675; DY-676; DY-678; Alexa Fluor 680 succinimidyl ester; DY-679; DY-680; DY-682; DY-681; DYQ-3; DYQ-700; Alexa Fluor 700 succinimidyl ester; DY-703; DY-701; DY-704; DY-700; DY-730; DY-731; DY-732; DY-734; DY-750; Cy7 succinimidyl ester; DY-749; DYQ-4; and Cy7.5 succinimidyl ester.

Reporter moieties, such as those coupled to a secondary antibody, may be selected from any of the detectable labels described above.

Enzyme Reactive Moieties

In some embodiments, enzyme reactive moieties include tyramide, tyramide derivatives, and quinone methide precursors and derivatives thereof.

In some embodiments, the enzyme reactive moiety is a tyramide or a derivative or analog thereof. Suitable tyramide moieties and tyramide derivatives include those described in U.S. application publication No. 2012/0171668, the disclosure of which is hereby incorporated by reference herein in its entirety. In some embodiments, the tyramide moiety or tyramide derivative is a substrate for an enzyme, e.g. peroxidase enzyme, a horse radish peroxidase enzyme.

In some embodiments, the enzyme reactive moiety has the structure provided by Formula (VIIA):

(VIIA)

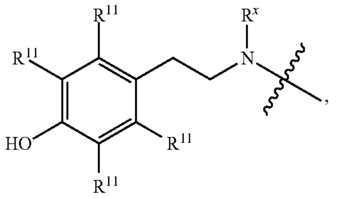

wherein each $R^{11}$ group is independently selected from hydrogen or a lower alkyl group having between 1 and 4 carbon atoms, and wherein $R^x$ is H or a $C_1$-$C_4$ alkyl group;

In other embodiments, the enzyme reactive moiety has the structure provided by Formula (VIIB):

(VIIB)

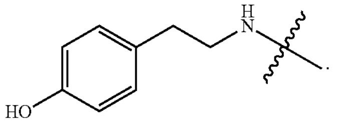

In some embodiments, the enzyme reactive moiety is a quinone methide precursor or a derivative thereof. Suitable quinone methide precursors or derivatives are described in U.S. application publication No. 2017/0089911, the disclosure of which is hereby incorporated by reference herein in its entirety. In some embodiments, the quinone methide precursor or its derivative is a substrate for an enzyme, e.g. a phosphatase, an alkaline phosphatase.

In some embodiments, the enzyme reactive moiety has the structure provided by Formula (VIIIA):

(VIIA)

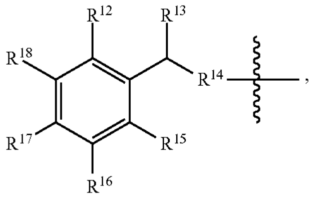

wherein $R^2$ is a group selected from phosphate, amide, nitro, urea, sulfate, methyl, ester, beta-lactam, or a sugar;

$R^{13}$ is a halide;

$R^{15}$, $R^{16}$, $R^{17}$, and $R^{18}$ are independently selected from hydrogen or an aliphatic group having between 1 and 4 carbon atoms; and $R^{14}$ is $-(CH_2)_wNH-$, $-O(CH_2)_wNH-$, $-N(H)C(O)(CH_2)_wNH-$, $-C(O)N(H)(CH_2)_wNH-$, $-(CH_2)_wO-$, $-O(CH_2)_wO-$, $-O(CH_2CH_2O)_w-$, $-N(H)C(O)(CH_2)_wO-$, $-C(O)N(H)(CH_2)_wO-$, $-C(o)N(H)(CH_2CH_2O)_w-$, $-(CH_2)_wS-$, $-O(CH_2)_wS-$, $-N(H)C(O)(CH_2)_wS-$, $-C(O)N(H)(CH_2)_wS-$, $-(CH_2)_wNH-$, $-C(O)N(H)(CH_2CH_2O)_wCH_2CH_2NH$, $-C(O)(CH_2CH_2O)_wCH_2CH_2NH-$, $-C(O)N(H)(CH_2)NHC(O)CH(CH_3)(CH_2)_wNH-$, or $-N(H)(CH_2)_wNH-$, where w is an integer ranging from 1 to 12.

In other embodiments, the enzyme reactive moiety has the structure provided by Formula (VIIIB):

(VIIIB)

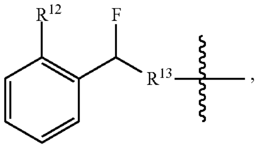

In other embodiments, the enzyme reactive moiety has the structure provided by Formula (VIIIC):

(VIIIC)

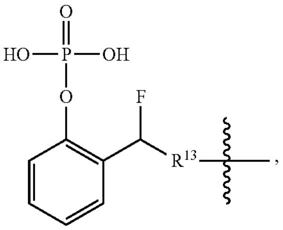

where $R^{13}$ $-(CH_2)_wNH-$, $-O(CH_2)_wNH-$, $-N(H)C(O)(CH_2)_wNH-$, $C(O)N(H)(CH_2)_wNH-$, $-(CH_2)_wO-$, $-O(CH_2)_wO-$, $-O(CH_2CH_2O)_w-$, $-N(H)C(O)(CH_2)_wO-$, $-C(O)N(H)(CH_2)_wO-$, $-C(o)N(H)(CH_2CH_2O)_w-$, $-(CH_2)_wS-$, $-O(CH_2)_wS-$, $-N(H)C(O)(CH_2)_wS-$, $-C(O)N(H)(CH_2)_wS-$, $-(CH_2)_wNH-$, $-C(O)N(H)(CH_2CH_2O)_wCH_2CH_2NH$, $-C(O)(CH_2CH_2O)_wCH_2CH_2NH-$, $-C(O)N(H)(CH_2)NHC(O)CH(CH_3)(CH_2)_wNH-$, or $-N(H)(CH_2)_wNH-$, where w is independently an integer ranging from 1 to 12. In some embodiments, $R^7$ is $C(O)N(H)(CH_2)_wNH$ and w is as defined above. In other embodiments, $R^7$ is $C(O)N(H)(CH_2)_wNH$ and w ranges from 2 to 6.

In other embodiments, the enzyme reactive moiety has the structure provided by Formula (VIIID):

(VIIID)

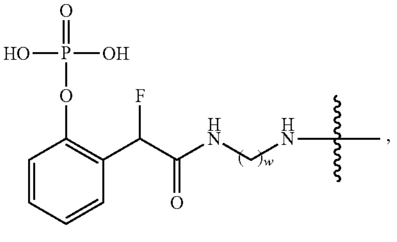

where w ranges from 1 to 12. In some embodiments w ranges from 1 to 8. In other embodiments, w ranges from 2 to 8. In yet other embodiments, w ranges from 2 to 6. In further embodiments, w is 6.

Further Coumarin-Based Reagents

In some embodiments, the coumarin-based reagent has the structure below:

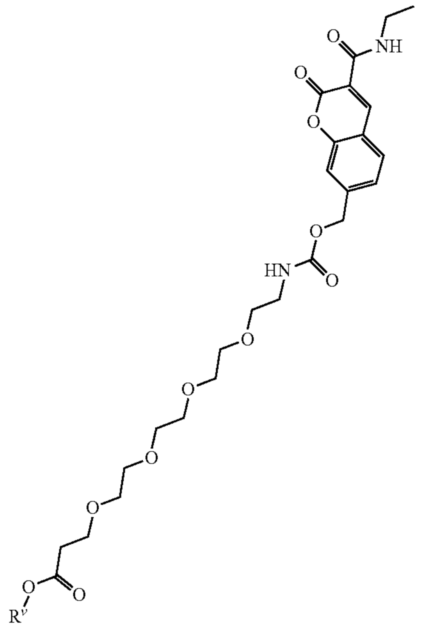
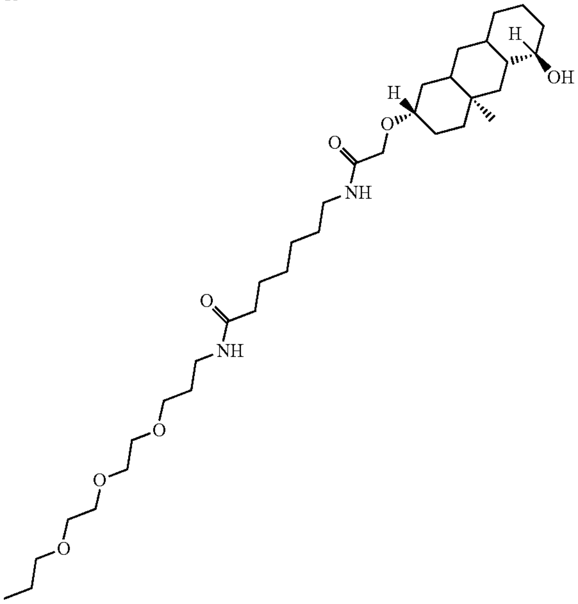
lp;2.4p
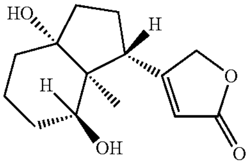
where $R^v$ is an enzyme reactive moiety or a reactive functional group.
In some embodiments, the coumarin-based reagent has the structure below:
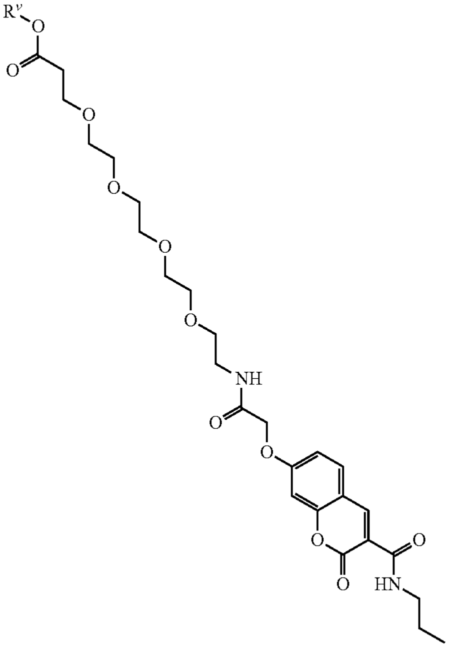
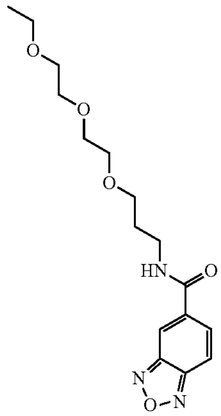
where $R^v$ is an enzyme reactive moiety or a reactive functional group.
In some embodiments, the coumarin-based reagent has the structure below:

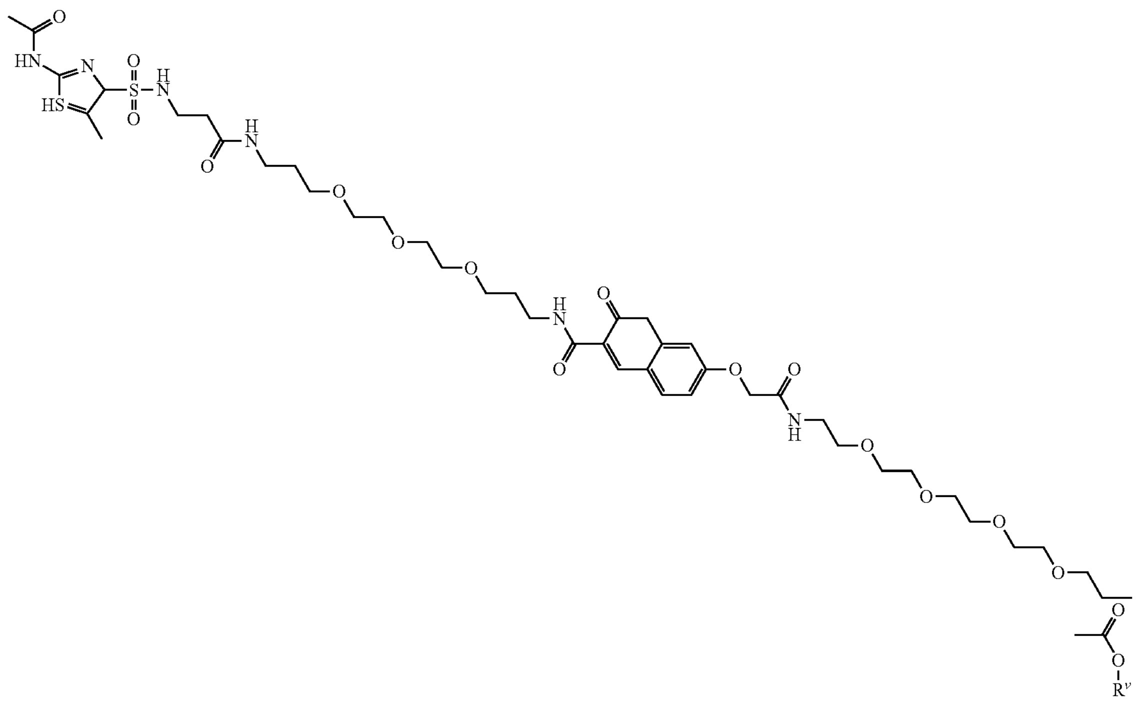
where $R^v$ is an enzyme reactive moiety or a reactive functional group.
In some embodiments, the coumarin-based reagent has the structure below:
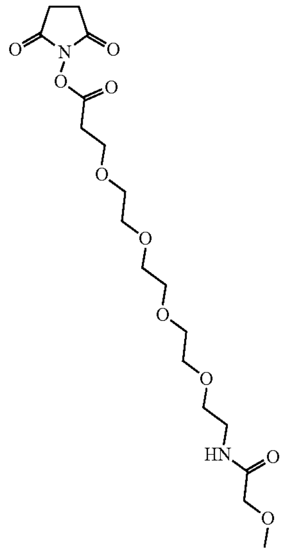
-continued
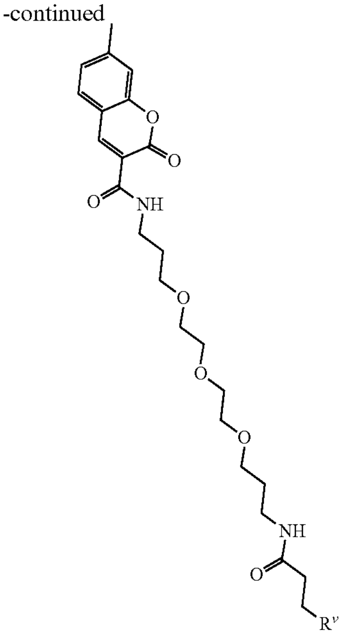
where $R^v$ is an enzyme reactive moiety or a reactive functional group.
In some embodiments, the coumarin-based reagent has the structure below:

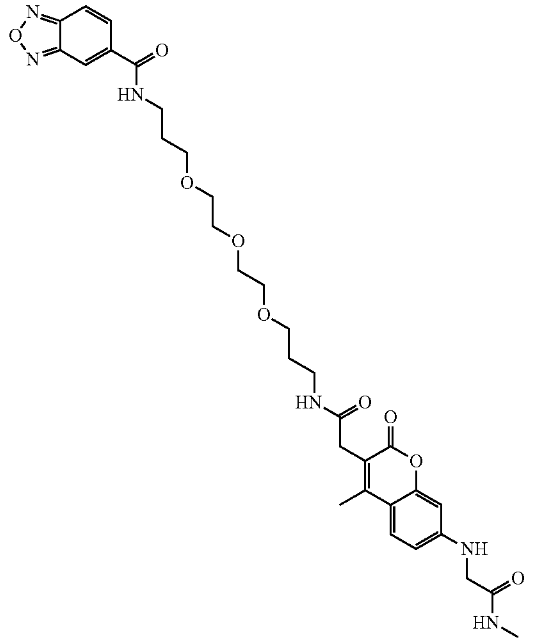

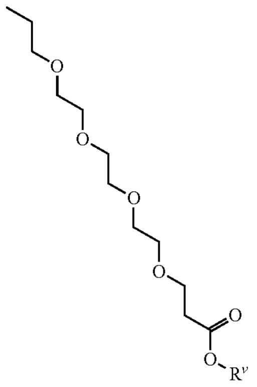

where $R^v$ is an enzyme reactive moiety or a reactive functional group.

In some embodiments, the coumarin-based reagent has the structure below:

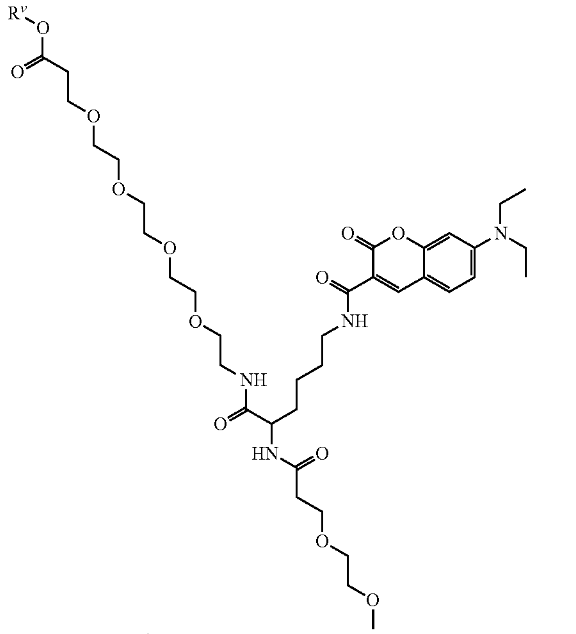

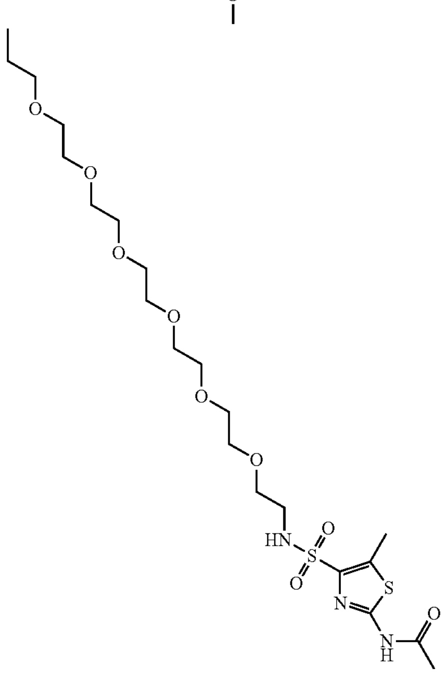

where $R^v$ is an enzyme reactive moiety or a reactive functional group.

Conjugates Including a Coumarin-Based Reagent

The present disclosure also provides for conjugates of a coumarin-based reagent and another substituent, e.g. a macromolecule, a drug, or a biomolecule. In some embodiments, the coumarin-based reagents of Formulas (IA), (IB), (IIA), (IIB), (IIC), or (IID) may be reacted with a macromolecule, a drug, or a biomolecule. In some embodiments, the conjugates have the general structure of T-[Coumarin-based reagent]$_{O}$, wherein T is selected from a specific binding entity, an amino acid, a peptide, a protein, a saccharide, a nucleoside, a nucleotide, an oligonucleotide, a drug, a lipid, or a nanoparticle, and o is an integer ranging from 1 to 10.

Various methods exist which may be employed to couple the coumarin-based reagent to the macromolecule, drug, or biomolecule. For example, to facilitate this binding the coumarin-based reagent may be attached to biomolecule-reactive groups, such as active ester groups, amino groups, sulfhydryl groups, carbohydrate groups, azido groups or carboxy groups. A variety of methodologies exist for reacting biomolecule-reactive groups with macromolecules or macromolecule fragments. Examples of such methodologies are photo-crosslinking and glutaraldehyde crosslinking. Still other methods for effecting such coupling will occur to those skilled in the art. See, for examples of such methods: Hermanson, G. T., Bioconjugate Techniques, Elsevier Science, London, 2008.

Active ester groups of the present invention should be selected such that they will not impair linkage of the extended linking group to a protein or macromolecule. Those skilled in the art will appreciate that active esters such as, for example, N-hydroxysuccinimide or N-hydroxysulfosuccinimide may be employed in the present invention. Alternatively, primary amino groups on the extended linking group may be coupled to primary amino groups on a protein by glutaraldehyde. Amino groups on proteins may be coupled to carboxy groups on the extended linking group. In addition, the extended linking group may be modified with a nitrophenyl azide such that coupling to a protein will occur when irradiated with visible light. Still other methods for effecting such coupling will occur to those skilled in the art.

In some embodiments, the conjugates of the present disclosure have the structure of either Formula (IXA) or (IXB):

$$T-[-[L^1]_m-W-[L^2]_n-R^z]_o, \qquad \text{(IXA)}$$

$$T-[-[L^1]_m-\underset{\substack{|\\ W}}{W}-[L^2]_n-R^z]_o, \qquad \text{(IXB)}$$

where T a substituent selected from a specific binding entity, an amino acid, a peptide, a protein, a saccharide, a nucleoside, a nucleotide, an oligonucleotide, a drug, a lipid, or a nanoparticle;

$R^z$ is a detectable label such as defined above;

is an integer ranging from 1 to 10;

$L^1$ and $L^2$ are linkers;

W includes a substituted or unsubstituted coumarin moiety or a moiety which is a substituted or an unsubstituted derivative or analog of coumarin;

Z is a bond, a —CH— group, a —CH—$CH_2$— group or a —$CH_2$—CH— group; and m and n are independently an integer ranging from 1 to 4.

In some embodiments, the specific binding entity is an antibody, an antibody fragment, a drug/antibody complex, or a nucleic acid. In some embodiments, the antibody is a primary antibody. In other embodiments, the antibody is a secondary antibody.

In some embodiments, $R^z$ is a hapten. In some embodiments, $R^z$ is an oxazole, a pyrazole, a thiazole, a benzofurazan, a triterpene, a urea, a thiourea other than a rhodamine thiourea, a nitroaryl other than dinitrophenyl or trinitrophenyl, a rotenoid, a cyclolignan, a heterobiaryl, an azoaryl, a benzodiazepine. In other embodiments, $R^z$ is a benzofurazan or a thiazolesulfonamide.

In other embodiments, $R^z$ is an enzyme, e.g. a peroxidase or a phosphatase. In yet other embodiments, $R^z$ is a fluorophore.

In some embodiments, the conjugates of the present disclosure have the structure of either Formula (IXC) or (IXD):

$$Ab-[-[L^1]_m-W-[L^2]_n-R^z]_o. \qquad \text{(IXC)}$$

$$Ab-[-[L^1]_m-\underset{\substack{|\\ W}}{Z}-[L^2]_n-R^z]_o. \qquad \text{(IXD)}$$

wherein Ab is an antibody;

$R^z$ is a detectable label such as defined above;

is an integer ranging from 1 to 10;

$L^1$ and $L^2$ are linkers;

W includes a substituted or unsubstituted coumarin moiety or a moiety which is a substituted or an unsubstituted derivative or analog of coumarin;

Z is a bond, a —CH— group, a —CH—$CH_2$— group or a —$CH_2$—CH— group; and m and n are independently an integer ranging from 1 to 4.

In some embodiments, the conjugates of the present disclosure have the structure of either Formula (IXE) or (IXF):

$$NA-[-[L^1]_m-W-[L^2]_n-R^z]_o. \qquad \text{(IXE)}$$

$$NA-[-[L^1]_m-\underset{\substack{|\\ W}}{Z}-[L^2]_n-R^z]_o. \qquad \text{(IXF)}$$

wherein NA is a nucleic acid;

$R^z$ is a detectable label such as defined above;

is an integer ranging from 1 to 10;

$L^1$ and $L^2$ are linkers;

W includes a substituted or unsubstituted coumarin moiety or a moiety which is a substituted or an unsubstituted derivative or analog of coumarin;

Z is a bond, a —CH— group, a —CH—$CH_2$— group or a —$CH_2$—CH— group; and m and n are independently an integer ranging from 1 to 4.

In some embodiments, $R^z$ is a hapten. In some embodiments, $R^z$ is an oxazole, a pyrazole, a thiazole, a benzofurazan, a triterpene, a urea, a thiourea other than a rhodamine thiourea, a nitroaryl other than dinitrophenyl or trinitrophenyl, a rotenoid, a cyclolignan, a heterobiaryl, an azoaryl, a benzodiazepine. In other embodiments, $R^z$ is a benzofurazan or a thiazolesulfonamide.

In some embodiments, a coumarin-based reagent (e.g. those having Formulas (IIA) or (IIB)) may be coupled to any portion of the antibody. Three functional groups in antibodies are the sites for covalent modifications: amines (—NH2), thiol groups (—SH) and carbohydrate residues (Shrestha D, et al, 2012). As such, any of the coumarin-based reagents having at least one reactive functional group disclosed herein may be coupled to amine residues, thiol residues, and carbohydrate residues or any combination thereof. In some embodiments, a coumarin-based reagent is coupled to Fc portions of the antibody. In other embodiments, a coumarin-based reagent is coupled to the hinge regions of the antibody. In some embodiments, a coumarin-based reagent is coupled to one or more of the Fc regions of the antibody and one or more of the hinge regions of the antibody. Indeed, any combination is contemplated by the present disclosure.

Amino group are generally favored primarily because of the abundance of these moieties in the antibody. However, the randomness of amino groups poses a risk that the antibody may become deactivated. (Adamczyk M, et al, 1999, Bioconjug Chem; Jeanson A, et al, 1988, J Immunol Methods; Vira S, et al, 2010, Anal Biochem; Pearson J E et al, 1998, J Immunol Methods). In some embodiments, one or more coumarin-based reagents are coupled to amino groups of an antibody.

On the other hand, and under appropriate reaction conditions, sulfhydryl labeling offers high specificity targeting of the disulfide bonds between the two heavy chains of the antibody in the hinge region. Since the hinge region is distant from the antigen binding site, this modification is believed to better preserve antibody's binding affinity. In some embodiments, one or more coumarin-based reagents are coupled to thiol groups of an antibody.

Conjugations at the carbohydrate moieties present in the Fc part of the antibody are similar to that of thiol group, such that modification occurs at a —CHO group distant from the antigen binding site. Again, it is believed that conjugation at the carbohydrate offers less of a negative impact on an antibody's binding affinity. The degree of labeling varies depending on the glycosylation status of a specific antibody. However, loss in antibody affinity was still reported by Jeanson A, et al, 1988, J Immunol Methods. In some embodiments, one or more coumarin-based reagents are coupled to carbohydrate groups of an antibody.

Detection of Coumarin-Based Conjugates

In some embodiments, the conjugates of any of Formulas (IXA), (IXB), (IXC), and (IXD) include a detectable label that facilitates the direct detection of the conjugate. For example, if the label of the coumarin-based conjugate comprises a fluorophore or a chromophore, the fluorophore or chromophore may be directly detected according to methods known to those of ordinary skill in the art.

In other embodiments, specific reagents are utilized to enable detection of any the conjugates of Formulas (IXA), (IXB), (IXC), (IXD), (IXE), and (IXF), and hence the targets in a tissue sample. In some embodiments, detection reagents are utilized which are specific to the particular detectable label of the conjugate. In some embodiments, the detection reagents comprise a secondary antibody which is specific for the label of the conjugate, e.g. the hapten moiety of the conjugate. For example, the secondary antibody may be an anti-label antibody or an anti-hapten antibody which itself is conjugated to a reporter moiety.

In some embodiments, the secondary antibody or anti-hapten antibody may be conjugated to a "reporter moiety" to effectuate detection of the conjugate of Formulas (IXA), (IXB), (IXC), (IXE), and (IXF). Any of the detectable labels described above are suitable for this purpose, i.e. may serve as a reporter moiety. In some embodiments, the reporter moiety of the secondary antibody includes chromogenic, fluorescent, phosphorescent and luminescent molecules and materials, catalysts (such as enzymes) that convert one substance into another substance to provide a detectable difference (such as by converting a colorless substance into a colored substance or vice versa, or by producing a precipitate or increasing sample turbidity), haptens that can be detected through antibody-hapten binding interactions using additional detectably labeled antibody conjugates, and paramagnetic and magnetic molecules or materials. Of course, the detectable labels can themselves also be detected indirectly, e.g. if the detectable label is a hapten, then yet another antibody specific to that hapten (e.g. an anti-hapten antibody) may be utilized in the detection of the detectable label, as known to those of ordinary skill in the art and described herein.

Methods of Detecting Targets with the Coumarin-Based Conjugates of any of Formulas (IXA), (IXB), (IXC), and (IXD) and Detection Reagents The present disclosure also provides methods of detecting one or more targets within a biological sample using any of the conjugates of Formulas (IXA), (IXB), (IXC), (IXD), (IXE), and (IXF), described herein. In some embodiments, a conjugate of any of Formulas (IXA), (IXB), (IXC), (IXD), (IXE), and (IXF) may be used in a simplex assay to directly or indirectly detect a particular target (e.g. a biomarker) within the biological sample (e.g. PD-L1, ER, PR, HER2 CD68, Ki67, CD20, etc.). In some embodiments, the biomarker is a nucleic acid (e.g. a DNA, RNA, mRNA, etc.). For example, FIG. 1 illustrates staining with a coumarin-based reagent conjugated to a nucleic acid probe (such as using those conjugates of Formulas (IXE) and (IXF) (where the coumarin-based reagent is coupled to DIG, where the DIG may be detected by through the application of suitable detection reagents as known in the art).

In some embodiments, the conjugates of any of Formulas (IXA), (IXB), (IXC), and (IXD) comprise a primary antibody (e.g. an antibody specific to PD-L1, ER, PR, HER2 CD68, Ki67, CD20, etc.). In these embodiments, the conjugates comprising a primary antibody may be used to directly "label" a target with the conjugate. In other embodiments, the conjugates of any of Formulas (IXA), (IXB), (IXC), and (IXD) comprise a secondary antibody. In these embodiments, and as discussed in more detail herein, a target (e.g. a protein target or a nucleic acid target) may be labeled with a primary antibody (for IHC) or a nucleic acid conjugate (e.g. a nucleic acid sequence coupled to a hapten, for ISH), and then the primary antibody or the nucleic acid conjugate may subsequently be "labeled" with the conjugate of any of Formulas (IXA), (IXB), (IXC), and (IXD) comprising a secondary antibody (which may be subsequently detected). These and other embodiments are described further herein.

Figure 2:
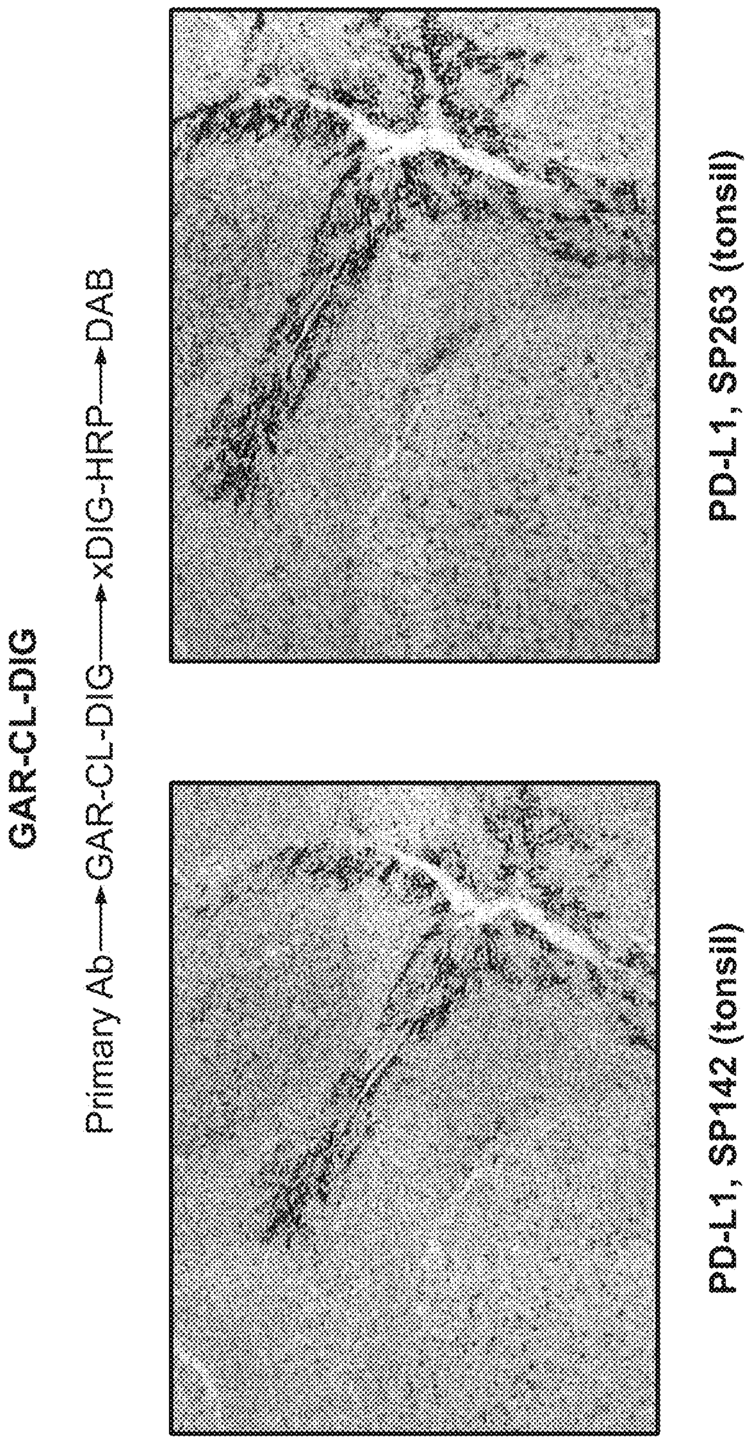
FIG. 2 illustrates staining of a sample with a coumarin-based conjugate including a goat-anti-rabbit antibody and a DIG hapten. Here, two tonsil tissue samples were labeled with a primary antibody specific to PD-L1, followed by the introduction of the coumarin-based conjugate to label the target within the sample with DIG. DIG is then detected through the introduction of an anti-DIG antibody coupled to a peroxidase, the peroxidase acting upon introduced 3,3'-Diaminobenzidine ("DAB").
Figure 3:
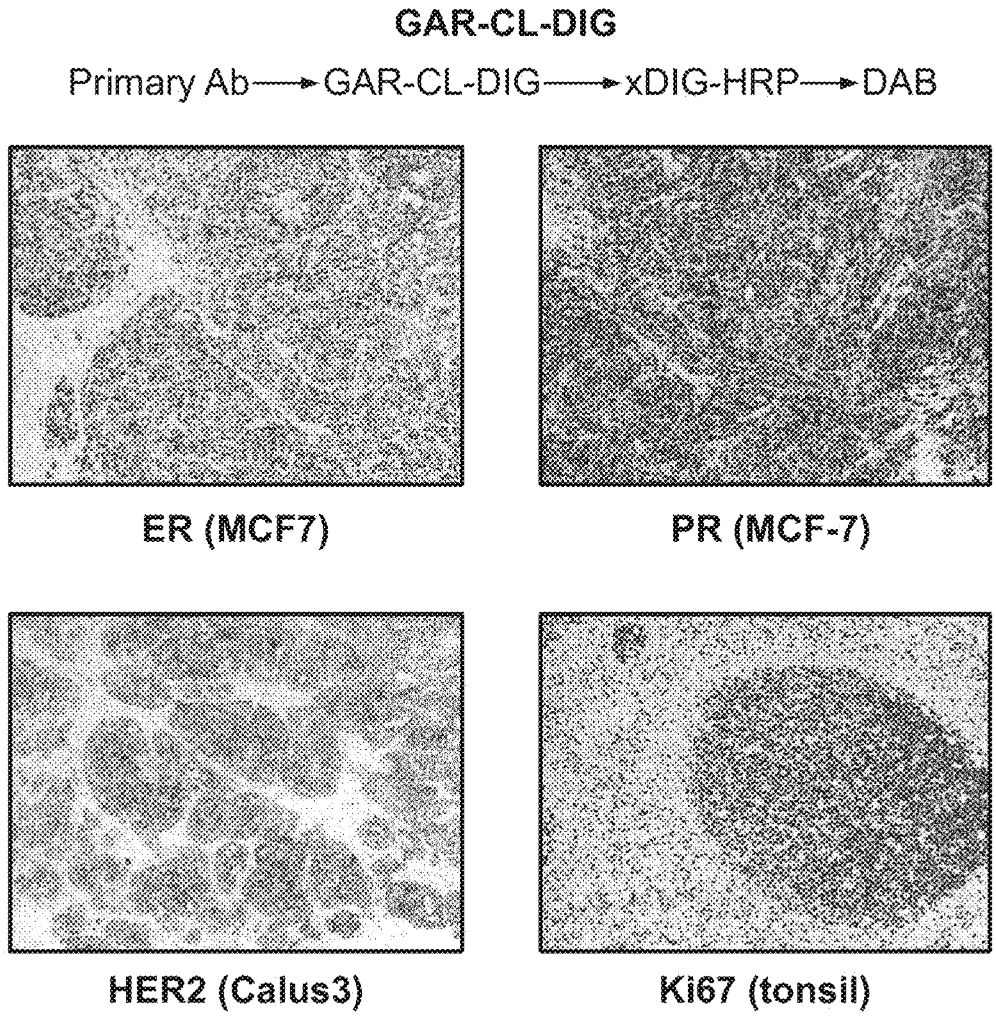
FIG. 3 illustrates staining of a sample with a coumarin-based conjugate including a goat-anti-rabbit antibody and a DIG hapten. Here, two tonsil tissue samples were labeled with primary antibodies specific to estrogen receptor (ER), progesterone receptor (PR), HER2, and Ki67, followed by the introduction of the coumarin-based conjugate to label the target within the sample with DIG. DIG is then detected through the introduction of an anti-DIG antibody coupled to a peroxidase, the peroxidase acting upon introduced 3,3'-Diaminobenzidine ("DAB").

By way of example, FIGS. 2 and 3 illustrate a secondary antibody-coumarin-based reagent conjugate which are utilized to label a primary antibody deposited onto tissue. In these figures, the secondary antibody is an anti-antibody antibody; and the conjugate is coupled to DIG. The DIG may be detected or visualized through the use of an anti-DIG antibody conjugated to an enzyme, followed by introduction of a chromogen, e.g. DAB.

In some embodiments, a coumarin-based conjugate may include a primary antibody where the coumarin-based primary antibody conjugate is specific for a target of interest, and where upon application of the coumarin-based primary antibody conjugate to the tissue sample, a target-coumarin-based primary antibody conjugate complex is formed. Following application of the coumarin-based primary antibody conjugate, detection reagents (e.g. an anti-label antibody or an anti-hapten antibody) may subsequently be applied such that the target-coumarin-based primary antibody conjugate complex may be detected. In some embodiments, the detection reagents comprise an anti-hapten antibody specific to the particular hapten detectable label of the coumarin-based primary antibody conjugate, where the anti-hapten antibody comprises a reporter moiety. The single target may then be visualized or otherwise detected.

In other embodiments, a tissue sample is first contacted with a primary antibody or a nucleic acid probe, forming either a target-primary antibody complex or a target-nucleic acid probe complex. Subsequently, a coumarin-based conjugate comprising a secondary antibody is introduced to the tissue sample, the secondary antibody portion of the coumarin-based conjugate being specific to either the (i) primary antibody, (ii) a label conjugated to the primary antibody, or (iii) a label conjugated to the nucleic acid probe. Application of the coumarin-based secondary antibody conjugate allows formation of a secondary complex, allowing the target to be "labeled." Following application of the coumarin-based secondary antibody conjugate and formation of the secondary complex, detection reagents (e.g. an anti-label antibody, an anti-hapten antibody) may be applied such that the secondary complex may be detected. In some embodiments, the detection reagents comprise an anti-hapten antibody specific to a particular label of the coumarin-based secondary antibody conjugate, where the anti-hapten antibody comprises a reporter moiety. The target may then be visualized or otherwise detected through the coupled reporter moiety.

Figure 4:
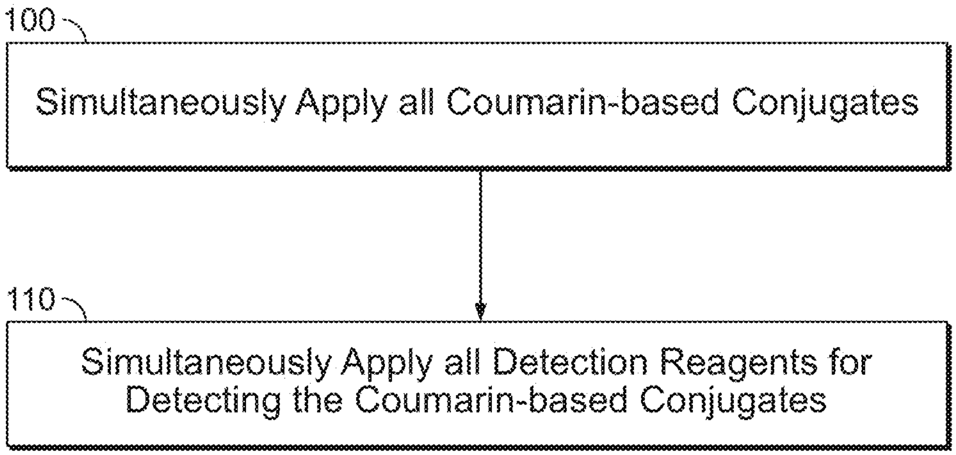
FIG. 4 sets forth a flowchart illustrating the steps of a multiplex detection strategy in accordance with some embodiments.

In some aspects of the present disclosure are provided methods of multiplex detection, including automated multiplex detection. FIG. 4 provides a flowchart illustrating one method for the multiplex detection of targets where a tissue sample is contacted simultaneously with a plurality of coumarin-based conjugates (step 100), where each coumarin-based conjugate is specific for a particular target, and where each coumarin-based conjugate comprises a different detectable label. While FIG. 4 depicts the application of coumarin-based conjugate, the skilled artisan will understand that the coumarin-based conjugate may comprise coumarin-based nucleic acid conjugates, coumarin-based primary antibody conjugates, and coumarin-based secondary antibody conjugates, depending on the target within the sample (e.g. a nucleic acid sequence, a protein target recognized by a primary antibody coumarin-based conjugate, or a pre-deposited primary antibody recognized by a secondary antibody coumarin-based conjugate).

In some embodiments, the sample may be contacted with two coumarin-based conjugates, where each coumarin-based conjugate is specific for a particular target, and where each coumarin-based conjugate comprises a different detectable label. In other embodiments, the sample may be contacted with three coumarin-based conjugates, where each coumarin-based conjugate is specific for a particular target, and where each coumarin-based conjugate comprises a different detectable label.

The coumarin-based conjugates (such as any of the conjugates of Formulas (IXA), (IXB)), may be supplied to the tissue sample as a "pool" or "cocktail" comprising each of the coumarin-based conjugates needed for the particular assay. The pooling of coumarin-based conjugates is believed to be possible since the coumarin-based conjugates are believed not to be cross-reactive to each other, at least not to the extent where any cross-reactivity would interfere with staining performance. Each coumarin-based conjugate will bind to their respective targets and form detectable target-coumarin-based conjugate complexes. In some embodiments, and following application of the coumarin-based conjugates, a blocking step is performed.

Following the simultaneous application of the coumarin-based conjugates (step 100), a plurality of detection reagents are simultaneously applied to the tissue sample (step 110), where each detection reagent facilitates detection of one of the coumarin-based conjugates initially applied (at step 100), and where each detection reagent comprises a different detectable label. In other embodiments, the detection reagents are secondary antibodies specific for a detectable label of the coumarin-based conjugate (e.g. anti-label antibodies specific to a label of the coumarin-based conjugate). In embodiments where anti-hapten antibodies are employed, the anti-hapten antibodies may be supplied to the tissue sample as a pool or cocktail comprising each of the anti-hapten antibodies necessary for detection of the target-coumarin-based antibody conjugate complexes. Following application of the detection reagents, in some embodiments the tissue sample may be stained with a counterstain. Signals from each of the reporter moieties may be visualized or otherwise detected (e.g. simultaneously visualized or detected).

One example of a multiplex assay utilizing coumarin-based conjugates is as follows. A first coumarin-based antibody conjugate comprising a first detectable label and specific to a first target (e.g. specific to one of PD-L1, ER, PR, HER2, CD68, Ki67, CD20, etc.) is introduced to a tissue sample. In some embodiments, the first coumarin-based antibody conjugate forms a detectable first target-coumarin-based antibody conjugate complex. Simultaneously, a second coumarin-based antibody conjugate comprising a detectable label and specific to a second target (e.g. another of PD-L1, ER, PR, HER2, CD68, Ki67, CD20, etc.) is introduced to the sample to form a second target-coumarin-based antibody conjugate complex. Third, fourth, and $n^{th}$ additional coumarin-based conjugates specific to other targets (forming "n" target-detection probe complexes) and having different detectable labels be further introduced simultaneously with the first and second coumarin-based conjugates.

After the coumarin-based antibody conjugates are deposited, they may be detected, either directly or indirectly depending, of course, on their configuration. In some embodiments, anti-label antibodies are introduced to enable detection of each of the target-coumarin-based antibody conjugate complex. In some embodiments, the anti-label antibodies are specific to the different reporter moieties of the coumarin-based conjugates, and where the anti-label antibodies are each conjugated to a different detectable label. In some embodiments, the detectable reagents are anti-label antibodies each conjugated to a fluorophore. In some embodiments, first, second, and $n^{th}$ anti-label antibodies are simultaneously introduced, where each of the first, second, and $n^{th}$ detection reagents are specific to the different coumarin-based conjugates, where each of the anti-label antibodies are conjugated to a fluorophore. In other embodiments, first, second, and $n^{th}$ anti-label antibodies are sequentially introduced, where each of the first, second, and $n^{th}$ detection reagents are specific to the different coumarin-based conjugates, and wherein each of the anti-label antibodies are conjugated to an enzyme.

As a further example of a multiplex assay according to the present disclosure, a first coumarin-based antibody conjugate specific to a first target (e.g. PD-L1, ER, PR, HER2) is introduced to a tissue sample, the first coumarin-based antibody conjugate having a first detectable label. In some embodiments, the first coumarin-based antibody conjugate forms a detectable first target-coumarin-based antibody conjugate complex. Either simultaneously or subsequently, a second coumarin-based antibody conjugate specific to a second target (e.g. PD-L1, ER, PR, HER2) is introduced to the sample to form a second target-coumarin-based antibody conjugate complex, the second coumarin-based antibody conjugate having a second detectable label. Third, fourth, and $n^{th}$ additional coumarin-based antibody conjugates each specific to other targets (forming "n" target-coumarin-based antibody conjugate complexes) may be further introduced, again either sequentially or simultaneously with the first and/or second coumarin-based antibody conjugates, where the third, fourth and $n^{th}$ coumarin-based antibody conjugates each have yet different detectable labels. After the coumarin-based antibody conjugates are deposited, they may be detected. In some embodiments, additional detection reagents are introduced to enable the detection of the targets and the additional detection reagents include those described herein (e.g. chromogenic detection reagents). In some embodiments, first, second, and $n^{th}$ detection reagents are sequentially introduced, where each of the first, second, and $n^{th}$ detection reagents comprise (i) a secondary antibody, namely an anti-label antibody, specific to each of the detectable label of the coumarin-based antibody conjugates, wherein the secondary antibody is conjugated to an enzyme; and (ii) a chromogenic substrate; wherein each of the first, second, and $n^{th}$ chromogenic substrates are different.

In yet other embodiments, the multiplex detection method comprises the steps of (i) contacting a biological sample with a first coumarin-based antibody conjugate to form a first target coumarin-based antibody conjugate complex; (ii) contacting the biological sample with a first labeling conjugate wherein the first labeling conjugate comprises a first enzyme (where the first labeling conjugate is an anti-label antibody that specifically binds to the first coumarin-based antibody conjugate and is configured to label the target with an enzyme); (iii) contacting the biological sample with a first signaling conjugate comprising a first latent reactive moiety and a first chromogenic moiety (see, e.g. U.S. patent application Ser. No. 13/849,160, the disclosure of which is incorporated herein by reference for a description of signaling conjugates and their constituent components); (iv) inactivating the first enzyme, such as by contacting the sample with a first enzyme inactivation composition to substantially inactivate or completely inactivate the first enzyme contained in the biological sample.

After the first enzyme is inactivated (optional), the multiplex method further comprises the steps of (v) contacting a biological sample with a second coumarin-based antibody conjugate to form a second target-coumarin-based antibody conjugate; (vi) contacting the biological sample with a second labeling conjugate wherein the second labeling conjugate comprises a second enzyme (where the second labeling conjugate is an anti-label antibody that specifically binds to the second coumarin-based antibody conjugate and is configured to label the target with an enzyme); (vii) contacting the biological sample with a second signaling conjugate comprising a second latent reactive moiety and a second chromogenic moiety; (viii) inactivating the second enzyme, such as by contacting the sample with a first enzyme inactivation composition to substantially inactivate or completely inactivate the first enzyme contained in the biological sample.

After the second enzyme is inactivated, the method may be repeated such that additional coumarin-based antibody conjugates may be introduced, along with additional detection reagents, to effectuate detection of other targets. Following introduction of all of the coumarin-based antibody conjugates (and other detection probes) and respective detection reagents or kits, the method further comprises the step of counterstaining the sample and/or detecting signals (manually or via an automated method) from the first, second, and $n^{th}$ chromogenic moieties, wherein each of the first, second, and $n^{th}$ chromogenic moieties are each different. Alternatively, each of the coumarin-based antibody conjugate may be added simultaneously or sequentially, but before any labeling conjugate is added. As another example, three coumarin-based antibody conjugate may be sequentially applied initially, prior to introduction of any detection reagents, and then each of the detection reagents added sequentially.

In the context of a multiplex assay where multiple targets are detected sequentially, and where the detection employs the use of enzymes, it is desirable to inactivate any reagent or endogenous enzymes between successive detection steps. As a result, it is believed that enzymes present in any one detection step will not interfere with those in a later detection steps. This in turn is believed to improve upon the visualization and detection of the different detectable moieties used in the multiplex assay. Any enzyme inactivation composition known in the art may be used for this purpose. In some embodiments, an enzyme inactivation composition is applied to inactivate the reagent or endogenous enzymes after each detection step. Exemplary enzyme inactivation compositions are disclosed in United States Patent Publication No. 2018/0120202 the disclosure of which is incorporated by reference herein in its entirety.

In some embodiments, a denaturation step prevents the enzyme used in a first set of detection reagents from acting on a second substrate. In some embodiments, the denaturant is a substance that denatures the enzyme in the first detection reagent set. In some embodiments, the denaturant is, for example, formamide, an alkyl-substituted amide, urea or a urea-based denaturant, thiourea, guanidine hydrochloride, or derivatives thereof. Examples of alkyl-substituted amides include, but are not limited to, N-propylformamide, N-butylformamide, N-isobutylformamide, and N,N-dipropylaformamide. In some embodiments, the denaturant is provided in a buffer. For example, formamide may be provided in a hybridization buffer comprising 20 mM dextran sulfate (50-57% % formamide (UltraPure formamide stock), 2×SSC (20×SSC stock containing 0.3 M citrate and 3M NaCl), 2.5 mM EDTA (0.5M EDTA stock), 5 mM Tris, pH 7.4 (1 mM Tris, pH 7.4 stock), 0.05% Brij-35 (10% stock containing polyoxyethylene (23) lauryl ether), pH 7.4. In some embodiments, the sample is treated with the denaturant for a period of time and under conditions sufficient to denature the first target probe detection enzyme, for example alkaline phosphatase. In some embodiments, the sample is treated with the denaturant for about 15 to about 30 minutes, preferably about 20 to 24 minutes at about 37° C. In some embodiments, the sample is treated with the denaturant for a period of time and under conditions sufficient to denature the target enzyme while preserving hybridization of the second nucleic acid probe to the target.

For those embodiments employing an anti-label antibody conjugated to an enzyme, conditions suitable for introducing the signaling conjugates or chromogenic substrates with the biological sample are used, and typically include providing a reaction buffer or solution that comprises a peroxide (e.g., hydrogen peroxide), and that has a salt concentration and pH suitable for allowing or facilitating the enzyme to perform its desired function. In general, this step of the method is performed at temperatures ranging from about 35° C. to about 40° C., although the skilled artisan will be able to select appropriate temperature ranges appropriate for the enzymes and signalizing conjugates selected. For example, it is believed that these conditions allow the enzyme and peroxide to react and promote radical formation on the latent reactive moiety of the signaling conjugate. The latent reactive moiety, and therefore the signaling conjugate as a whole, will deposit covalently on the biological sample, particularly at one or more tyrosine residues proximal to the immobilized enzyme conjugate, tyrosine residues of the enzyme portion of the enzyme conjugate, and/or tyrosine residues of the antibody portion of the enzyme conjugate. The biological sample is then illuminated with light and the target may be detected through absorbance of the light produced by the chromogenic moiety of the signaling conjugate.

Methods of Detecting the Conjugates of any of Formulas (IXA), (IXB), (IXC), (IXD), (IXE), and (IXF) in Conjunction with Other Specific Binding Entities In some aspects of the present disclosure, the conjugates of any of Formulas (IXA), (IXB), (IXC), and (IXD) are used in conjugation with other specific binding entities to effect multiplex detection of targets in a tissue sample. The skilled artisan will appreciate that any of the above-identified methods and procedures may be adapted accordingly for any assay employing both conjugates of any of Formulas (IXA), (IXB), (IXC), and (IXD) and other specific binding entities.

In some embodiments, the other specific binding entities include nucleic acids for in situ hybridization and unmodified antibodies for IHC. As used herein, the terms "unmodified antibody" or "unmodified antibodies" refer to those antibodies that do not comprise a coumarin-based reagent as disclosed herein, but includes those antibodies conjugated to a hapten or another label. In essence, "unmodified antibodies" are native antibodies traditionally used in IHC assays, which are specific to a particular target (e.g. an anti-CD3 antibody) and which may be detected, such as with anti-species secondary antibodies or, if they comprise a label, an anti-label antibody. By way of example, a rabbit anti-CD3 antibody may be detected with a goat anti-rabbit antibody. Likewise, a rabbit anti-CD3 antibody conjugated to a hapten may be detected with an anti-hapten antibody. For example, a unmodified antibody specific to ER may be introduced to a sample and later detected, while simultaneously or sequentially a coumarin-based conjugate of the present disclosure specific to PR may be introduced to the same sample and then detected.

Methods of Detecting Targets in a Sample Using the Coumarin-Based Reagents of Formulas (IIIA), (IIIB), (IIIC), and (IIID)

The present disclosure also provides methods of detecting one or more targets within a tissue sample using coumarin-based reagents, e.g. those compounds of Formulas (IIIA), (IIIB), (IIIC), and (IIID)).

In some embodiments, a compound of Formula (IIIA), (IIIB), (IIIC), and (IIID) having an enzyme reactive moiety (e.g. where "A" is a derivative of tyramide or a quinone methide derivative) and having a detectable label (e.g. where "B" is a hapten) is brought into contact with a target-bound enzyme (e.g. an antibody-enzyme conjugate or a nucleic acid-enzyme conjugate which has been already deposited onto a biological sample) to produce a reactive intermediate. For example, an antibody-peroxidase conjugate may be deposited onto a target and the peroxidase enzyme may react with an enzyme reactive moiety of a compound of any of Formulas (IIIA), (IIIB), (IIIC), and (IIID) upon its introduction to the sample. By way of another example, a nucleic acid-phosphatase conjugate may hybridize to a target within a sample and the conjugated phosphatase enzyme may react with an enzyme reactive moiety of a compound of any of Formulas (IIIA), (IIIB), (IIIC), and (IIID) upon its introduction to the sample.

In some embodiments, the reactive intermediate forms a covalent bond to a nucleophile on or within a biological sample, thus providing an immobilized tissue-coumarin based compound complex. By virtue of the detectable label of the compounds of Formulas (IIIA), (IIIB), (IIIC), and (IIID), the tissue-coumarin based complex may be visualized. For example, if the detectable label is a hapten, anti-hapten antibodies conjugated to a reporter (e.g. a chromogen or a fluorophore) may be introduced to detect the tissue-coumarin based compound complex. Methods of detection and visualization using compounds having an enzyme reactive moiety are described in US Patent Publication Nos. 2017/0089911 and 2012/0171668, the disclosures of which are hereby incorporated by reference herein in their entireties.

Figure 5:
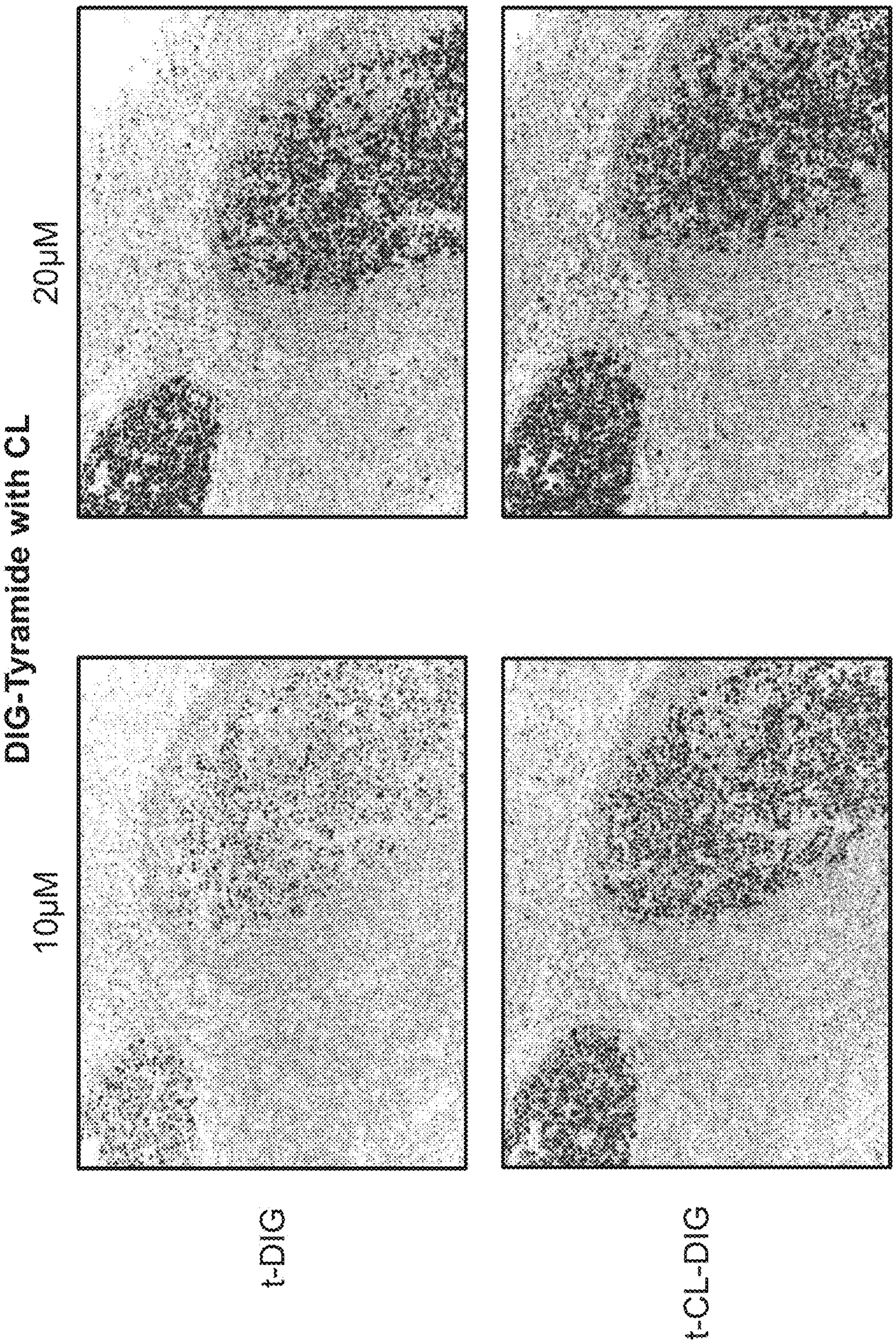
FIG. 5 illustrates the use of coumarin-based moieties of any of Formula (IIIA), (IIIB), (IIIC), and (IIID) coupled to a tyramide moiety and a hapten, e.g. DIG, and compares staining performance to those tyramide moieties coupled directed to DIG.

FIG. 5 illustrates the use of coumarin-based moieties of any of Formula (IIIA), (IIIB), (IIIC), and (IIID) coupled to a tyramide moiety and a hapten, e.g. DIG, and compares staining performance to those tyramide moieties coupled directed to DIG.

Methods of Detecting Targets in a Sample Using the Click Conjugates of Formulas (IIIE) and (IIIF)

The reagents of Formulas (IIIE) and (IIIF) may be used to detect targets within a sample using certain click conjugates. In some embodiments, a reagent having a Formula (IIIE) or (IIIF), which includes an enzyme reactive moiety and further includes a functional group capable of participating in a click chemistry reaction, is brought into contact with a target-bound enzyme (e.g. the target bound enzyme may be an antibody-enzyme conjugate which has been already deposited onto a biological sample) to produce a reactive intermediate. In some embodiments, the reactive intermediate forms a covalent bond to a nucleophile on or within a biological sample, thus providing an immobilized tissue-coumarin based compound complex. The immobilized tissue-click conjugate complex may then react with a click conjugate comprising a reporter moiety and including a functional group capable of participating in a click chemistry reaction, provided that the click conjugate and immobilized tissue-click conjugate complex possess reactive functional groups that may react with each other to form a covalent bond. The reaction product of immobilized tissue-click conjugate complex and the click conjugate produces the immobilized tissue-click adduct complex. The tissue-click adduct complex may be detected by virtue of signals transmitted from the linked reporter moiety. Click conjugates useful for reacting with the immobilized tissue-click conjugate complex include those described in PCT Publication No. WO/2018/002016, the disclosure of which is hereby incorporated by reference herein in its entirety. Further details of methods of detection are also disclosed in PCT Publication No. WO/2018/002016 and again, those disclosures are each incorporated by reference herein in their entireties.

Synthesis of Coumarin-Based Reagents

Methods of synthesizing various types of coumarin-based reagents, such as any of the reagents of Formulas (IA) or (IB) are described below.

Synthesis of 2,5-dioxopyrrolidin-1-yl 7-hydroxy-2-oxo-2H-chromene-3-carboxylate 7-hydroxy-2-oxo-2H-chromene-3-carboxylic acid (Sigma-Aldrich, 500 mg, 2.27 mmol) was dissolved in 10 ml dry DMF and to the solution added DSC (641 mg, 2.50 mmol) and DMAP (416 mg, 3.40 mmol). The solution was stirred at room temperature (r.t.) for one hour and then diluted with 50 ml DCM. The solution was washed 3 times with 50 ml water and ounce with 50 ml brine then concentrated under vacuum before purifying by silica gel chromatography (2% isopropanol/DCM to 10% isopropanol/DCM) to give 632 mg (86% yield) of 2,5-dioxopyrrolidin-1-yl 7-hydroxy-2-oxo-2H-chromene-3-carboxylate (compound 10).

(10)

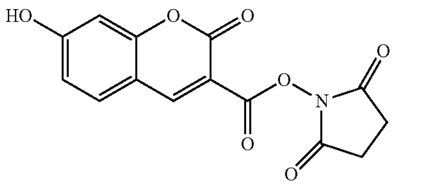

Synthesis of tert-butyl (1-(7-hydroxy-2-oxo-2H-chromen-3-yl)-1-oxo-6,9,12-trioxa-2-azapentadecan-15-yl)carbamate In this example, a linker group is introduced to the coumarin moiety.

2,5-dioxopyrrolidin-1-yl 7-hydroxy-2-oxo-2H-chromene-3-carboxylate (500 mg, 1.65 mmol) was dissolved in 10 ml DCM and to the solution added tert-butyl (3-(2-(3-amino-propoxy) ethoxy)propyl)carbamate (547 mg, 1.98 mmol) and triethylamine (334 mg, 3.3 mmol) and the reaction stirred at r. t. for 16 hr. Upon completion, the reaction was concentrated under reduced pressure, and purified by silica gel chromatography (2% methanol/DCM to 10% methanol/DCM) to give 688 mg (82% yield) tert-butyl (1-(7-hydroxy-2-oxo-2H-chromen-3-yl)-1-oxo-6,9,12-trioxa-2-azapenta-decan-15-yl)carbamate (compound 11) as a yellow oil.

(11)

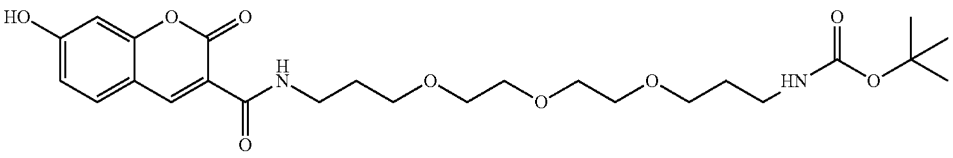

Synthesis of tert-butyl 2-((3-((2,2-dimethyl-4-oxo-3,9,12,15-tetraoxa-5-azaoctadecan-18-yl)carbamoyl)-2-oxo-2H-chromen-7-yl)oxy)acetate tert-butyl (1-(7-hydroxy-2-oxo-2H-chromen-3-yl)-1-oxo-6,9,12-trioxa-2-azapentadecan-15-yl)carbamate (407 mg, 0.80 mmol) was dissolved in 10 ml of dry DMF and to the solution added tert-butyl 2-bromoacetate (172 mg, 0.884 mmol) and potassium carbonate (330 mg, 2.41 mmol) and the reaction stirred on an oil bath at 60 C. After 3 hr, the reaction was diluted with 70 ml DCM, and the solution washed 3 times with 100 ml water and ounce with 100 ml brine. The solution was concentrated under vacuum before purifying by silica gel chromatography (2% methanol/DCM to 12% methanol/DCM) to give 398 mg (80% yield) of tert-butyl 2-((3-((2,2-dimethyl-4-oxo-3,9,12,15-tetraoxa-5-azaoctadecan-18-yl)carbamoyl)-2-oxo-2H-chromen-7-yl)oxy)acetate (compound 12).

(12)

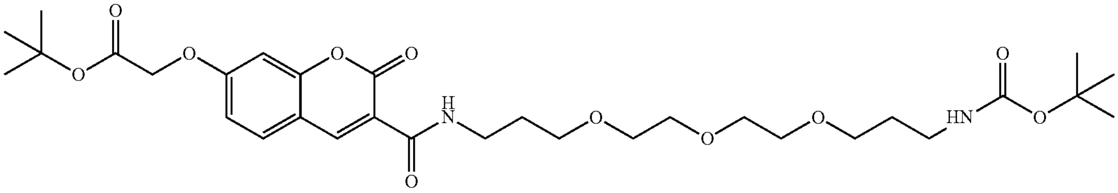

Synthesis of 2-((3-((3-(2-(2-(3-aminopropoxy)ethoxy)ethoxy)propyl)-carbamoyl)-2-oxo-2H-chromen-7-yl)oxy)acetic acid tert-butyl 2-((3-((2,2-dimethyl-4-oxo-3,9,12,15-tetraoxa-5-azaoctadecan-18-yl)carbamoyl)-2-oxo-2H-chromen-7-yl)oxy)acetate (398 mg, 0.64 mmol) was dissolved in 20 ml 35% TFA/DCM and stirred at r.t until the reaction was complete by HPLC (approximately 4 hr). The reaction was then concentrated under vacuum, azeotroped 3× with toluene and dried overnight under high vacuum to give 372 mg 2,2,2-trifluoroacetic acid compound with 2-((3-((3-(2-(2-(3-aminopropoxy)ethoxy)ethoxy)propyl)carbamoyl)-2-oxo-2H-chromen-7-yl)oxy)acetic acid (compound 13) (1:1) which was used without further purification.

(13)

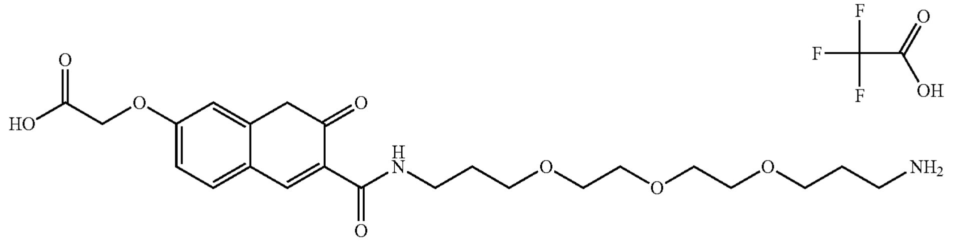

Synthesis of 2-((3-((1-(((3S,10S,12R,13S,14S,17R)-12,14-dihydroxy-10,13-dimethyl-17-(5-oxo-2,5-dihydrofuran-3-yl)hexadecahydro-1H-cyclopenta[a]phenanthren-3-yl)oxy)-2,10-dioxo-15,18,21-trioxa-3,11-diazatetracosan-24-yl)carbamoyl)-2-oxo-2H-chromen-7-yl)oxy)acetic acid In this example, a hapten moiety is introduced.

To a solution of 2,5-dioxopyrrolidin-1-yl 7-(2-(((3S,10S,12R,13S,14S,17R)-12,14-dihydroxy-10,13-dimethyl-17-(5-oxo-2,5-dihydrofuran-3-yl)hexadecahydro-1H-cyclopenta[a]phenanthren-3-yl)oxy)acetamido)heptanoate (90 mg, 0.137 mmol) in 3 ml dry DMF was added 2-((3-((3-(2-(2-(3-aminopropoxy)ethoxy)ethoxy)propyl)carbamoyl)-2-oxo-2H-chromen-7-yl)oxy)acetic acid 2,2,2-trifluoroacetic acid salt (1:1) (120 mg 0.205 mmol) and Huenigs base (82 µL, 0.480 mmol) and the reaction allowed to stir o.n. at r.t. The crude reaction was filtered through a 0.2-micron filter and purified by preparative HPLC. The pure fractions were combined and lyophilized to give 116 mg (83% yield) of 2-((3-((1-(((3S,10S,12R,13S,14S,17R)-12,14-dihydroxy-10,13-dimethyl-17-(5-oxo-2,5-dihydrofuran-3-yl)hexadecahydro-1H-cyclopenta[a]phenanthren-3-yl)oxy)-2,10-dioxo-15,18,21-trioxa-3,11-diazatetracosan-24-yl)carbamoyl)-2-oxo-2H-chromen-7-yl)oxy)acetic acid (compound 14) as on off white powder.

Synthesis of 1-((3-((1-(((3S,10S,12R,13S,14S,17R)-12,14-dihydroxy-10,13-dimethyl-17-(5-oxo-2,5-dihydrofuran-3-yl)hexadecahydro-1H-cyclopenta[a]phenanthren-3-yl)oxy)-2,10-dioxo-15,18,21-trioxa-3,11-diazatetracosan-24-yl)carbamoyl)-2-oxo-2H-chromen-7-yl)oxy)-2-oxo-6,9,12,15-tetraoxa-3-azaoctadecan-18-oic acid In this example, a second Linker is introduced to the coumarin moiety.

To a solution of 2-((3-((1-(((3S,10S,12R,13S,14S,17R)-12,14-dihydroxy-10,13-dimethyl-17-(5-oxo-2,5-dihydrofuran-3-yl)hexadecahydro-1H-cyclopenta[a]phenanthren-3-yl)oxy)-2,10-dioxo-15,18,21-trioxa-3,11-diazatetracosan-24-yl)carbamoyl)-2-oxo-2H-chromen-7-yl)oxy)acetic acid (130 mg, 0.129 mmol) in 10 ml dry DCM was added N-hydroxysuccinimide (19 mg, 0.167 mmol) and 1.0 M DCC in DCM (167 µL, 0.167 mmol) and the reaction stirred at r.t. until the formation of the active ester was complete as determined by HPLC (approximately 4 hours). The urea byproduct was removed by filtration and to the solution was added 1-amino-3,6,9,12-tetraoxapentadecan-15-oic acid (44 mg, 0.167 mmol) and Huenigs base (66 µL, 0.167 mmol) and the reaction stirred at r.t. overnight. The reaction was concentrated, taken in minimal methanol and purified by preparative HPLC. The pure fractions were combined and (14)

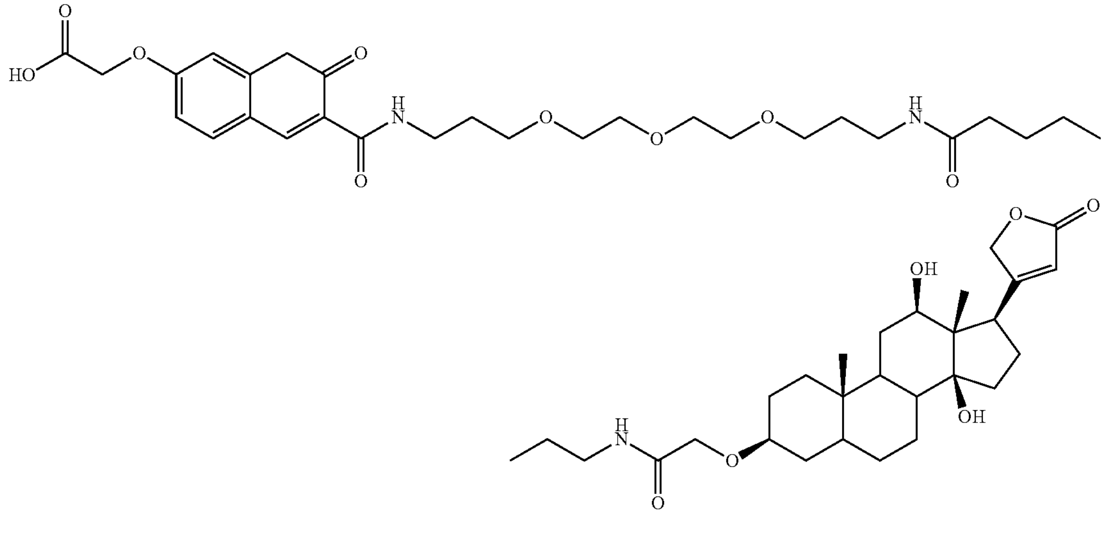

lyophilized to give 125 mg (76% yield) of 1-((3-((1-(((3 S,10S,12R,13 S,14S,17R)-12,14-dihydroxy-10,13-dimethyl-17-(5-oxo-2,5-dihydrofuran-3-yl)hexadecahydro-11H-cyclopenta[a]phenanthren-3-yl)oxy)-2,10-dioxo-15,18,21-trioxa-3,11-diazatetracosan-24-yl)carbamoyl)-2-oxo-2H-chromen-7-yl)oxy)-2-oxo-6,9,12,15-tetraoxa-3-azaoctadecan-18-oic acid (compound 15) as an off white powder.

(15)

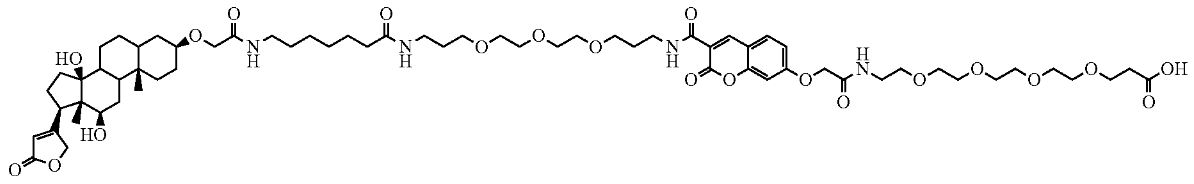

Synthesis of 2,5-dioxopyrrolidin-1-yl 1-((3-((1-(((3S,10S,12R,13S,14S,17R)-12,14-dihydroxy-10,13-dimethyl-17-(5-oxo-2,5-dihydrofuran-3-yl)hexadecahydro-1H-cyclopenta[a]phenanthren-3-yl)oxy)-2,10-dioxo-15,18,21-trioxa-3,11-diazatetracosan-24-yl)carbamoyl)-2-oxo-2H-chromen-7-yl)oxy)-2-oxo-6,9,12,15-tetraoxa-3-azaoctadecan-18-oate In this example, the starting material is derivatized such that the resulting reagent is able to be coupled to a macromolecule, such as a protein or antibody.

To a solution of 1-((3-((1-(((3S,10S,12R,13S,14S,17R)-12,14-dihydroxy-10,13-dimethyl-17-(5-oxo-2,5-dihydrofuran-3-yl)hexadecahydro-1H-cyclopenta[a]phenanthren-3-yl)oxy)-2,10-dioxo-15,18,21-trioxa-3,11-diazatetracosan-24-yl)carbamoyl)-2-oxo-2H-chromen-7-yl)oxy)-2-oxo-6,9,12,15-tetraoxa-3-azaoctadecan-18-oic acid (25 mg, 0.02 mmol) in 10 ml dry DCM was added N-hydroxysuccinimide (2.3 mg, 0.03 mmol) and 1.0 M DCC in DCM (30 μL, 0.03 mmol) and the reaction stirred at r.t. until the formation of the active ester was complete as determined by HPLC (approximately 4 hours). The urea byproduct was removed by filtration, the reaction concentrated, taken in minimal methanol and purified by preparative HPLC. The pure fractions were combined and lyophilized to give 22 mg (80% yield) of 2,5-dioxopyrrolidin-1-yl 1-((3-((1-(((3S,10S,12R,13S,14S,17R)-12,14-dihydroxy-10,13-dimethyl-17-(5-oxo-2,5-dihydrofuran-3-yl)hexadecahydro-1H-cyclopenta[a]phenanthren-3-yl)oxy)-2,10-dioxo-15,18,21-trioxa-3,11-diazatetracosan-24-yl)carbamoyl)-2-oxo-2H-chromen-7-yl)oxy)-2-oxo-6,9,12,15-tetraoxa-3-azaoctadecan-18-oate (compound 16) as an off white powder.

(16)

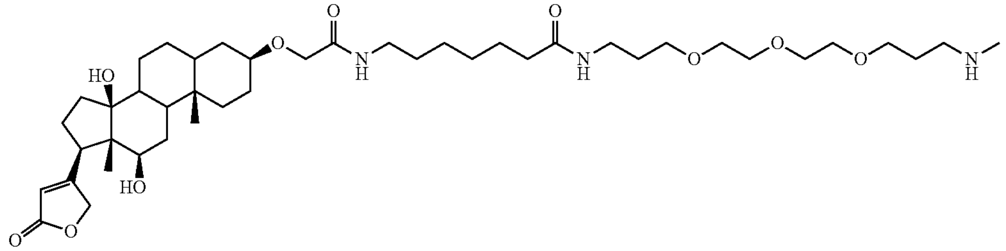

-continued

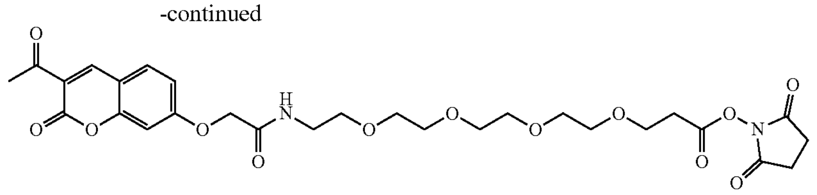

Synthesis of 4-hydroxyphenethyl 1-((3-((1-(((3S,10S,12R,13S,14S,17R)-12,14-dihydroxy-10,13-dimethyl-17-(5-oxo-2,5-dihydrofuran-3-yl)hexadecahydro-1H-cyclopenta[a]phenanthren-3-yl)oxy)-2,10-dioxo-15,18,21-trioxa-3,11-diazatetracosan-24-yl)carbamoyl)-2-oxo-2H-chromen-7-yl)oxy)-2-oxo-6,9,12,15-tetraoxa-3-azaoctadecan-18-oate In this example, an enzyme reactive moiety is introduced, specifically a tyramide moiety.

To a solution of 2,5-dioxopyrrolidin-1-yl 1-((3-((1-(((3S,10S,12R,13S,14S,17R)-12,14-dihydroxy-10,13-dimethyl-17-(5-oxo-2,5-dihydrofuran-3-yl)hexadecahydro-1H-cyclopenta[a]phenanthren-3-yl)oxy)-2,10-dioxo-15,18,21-trioxa-3,11-diazatetracosan-24-yl)carbamoyl)-2-oxo-2H-chromen-7-yl)oxy)-2-oxo-6,9,12,15-tetraoxa-3-azaoctadecan-18-oate (20 mg, 0.015 mmol) in 2 ml dry DMF was added tyramine (4.1 mg, 0.030 mmol) and triethyl amine (4.2 μL, 0.030 mmol) and the reaction stirred at r.t. overnight. The crude reaction was filtered through a 0.2 micron filter and purified by preparative HPLC. The pure fractions were combined and lyophilized to give 17 mg (81% yield) of 4-hydroxyphenethyl 1-((3-((1-(((3S,10S,12R,13S,14S,17R)-12,14-dihydroxy-10,13-dimethyl-17-(5-oxo-2,5-dihydrofuran-3-yl)hexadecahydro-1H-cyclopenta[a]phenanthren-3-yl)oxy)-2,10-dioxo-15,18,21-trioxa-3,11-diazatetracosan-24-yl)carbamoyl)-2-oxo-2H-chromen-7-yl)oxy)-2-oxo-6,9,12,15-tetraoxa-3-azaoctadecan-18-oate (compound 17) as an off white powder.

(17)

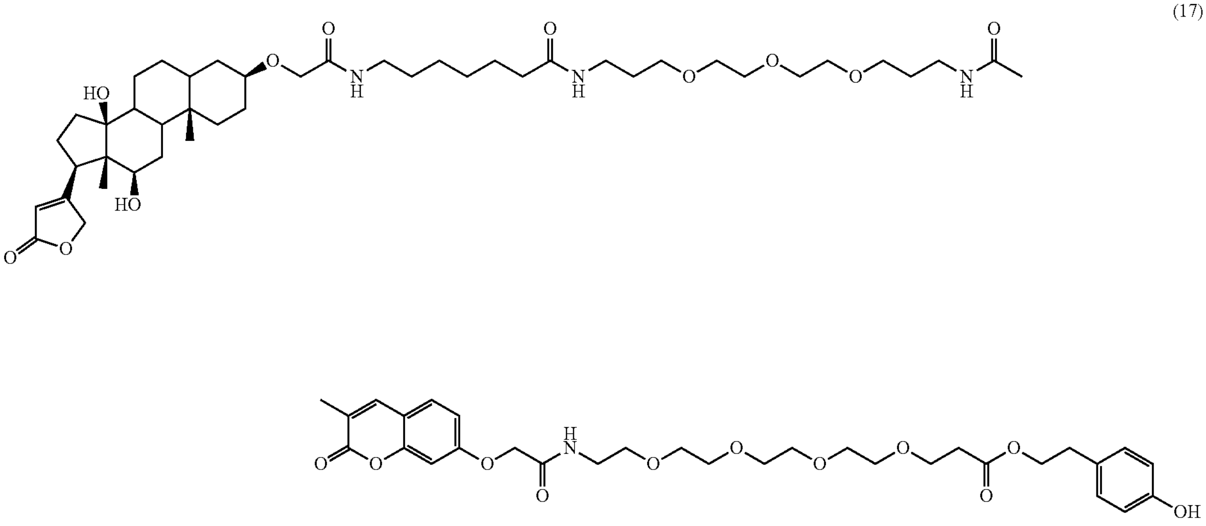

Synthesis of 2-((3-((2,2-dimethyl-4-oxo-3,9,12,15-tetraoxa-5-azaoctadecan-18-yl)carbamoyl)-2-oxo-2H-chromen-7-yl)oxy)acetic acid To a solution of 2,2,2-trifluoroacetic acid salt of 2-((3-((3-(2-(2-(3-aminopropoxy)ethoxy)ethoxy)propyl)carbamoyl)-2-oxo-2H-chromen-7-yl)oxy)acetic acid (1:1) (8.03 g, 13.83 mmol) in 50 ml dioxane/water (1:1) was added (Boc)2O (3.02 g, 13.83 mmol) and triethyl amine (4.38 ml, 31.46) and the reaction stirred at r.t. overnight. The reaction was diluted with 100 ml DCM and washed 2× with 50 ml water and ounce with brine. The organic phase dried by filtering through a plug of MgSO4 then concentrated prior to purification by silica gel chromatography (4% methanol/DCM to 15% methanol/DCM) to give 6.48 g (83% yield) of 2-((3-((2,2-dimethyl-4-oxo-3,9,12,15-tetraoxa-5-azaoctadecan-18-yl)carbamoyl)-2-oxo-2H-chromen-7-yl)oxy)acetic acid (compound 20).

(20)

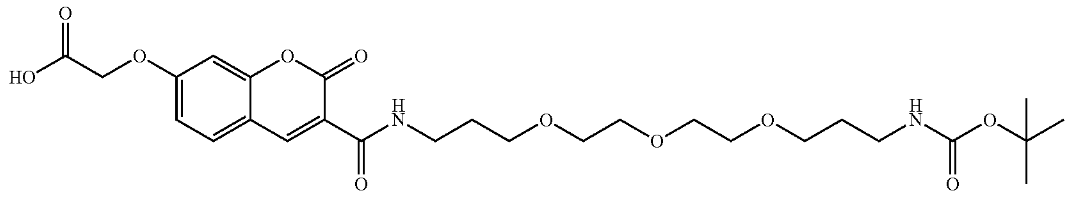

Synthesis of 1-((3-((2,2-dimethyl-4-oxo-3,9,12,15-tetraoxa-5-azaoctadecan-18-yl)carbamoyl)-2-oxo-2H-chromen-7-yl)oxy)-2-oxo-6,9,12,15-tetraoxa-3-azaoctadecan-18-oic acid To a solution of 2-((3-((2,2-dimethyl-4-oxo-3,9,12,15-tetraoxa-5-azaoctadecan-18-yl)carbamoyl)-2-oxo-2H-chromen-7-yl)oxy)acetic acid (6.48 g, 11.4 mmol) in 40 ml dry DCM was added 1.0 M DCC in DCM (17.16 ml, 17.16 mmol) and NHS (1.97 g, 17.16 mmol) and the reaction stirred at r.t. until the ester formation was complete (5 hr). The urea byproduct was removed by filtration and to the solution was added 1-amino-3,6,9,12-tetraoxapentadecan-15-oic acid (4.55 g, 17.16 mmol) and Huenigs base (2.22 g, 17.16 mmol) and the reaction stirred at r.t. overnight. The reaction was concentrated, taken in minimal methanol and purified by preparative HPLC. The pure fractions were combined and lyophilized to give 7.42 g (80% yield) of 1-((3-((2,2-dimethyl-4-oxo-3,9,12,15-tetraoxa-5-azaoctadecan-18-yl)carbamoyl)-2-oxo-2H-chromen-7-yl)oxy)-2-oxo-6,9,12,15-tetraoxa-3-azaoctadecan-18-oic acid (compound 21).

(21)

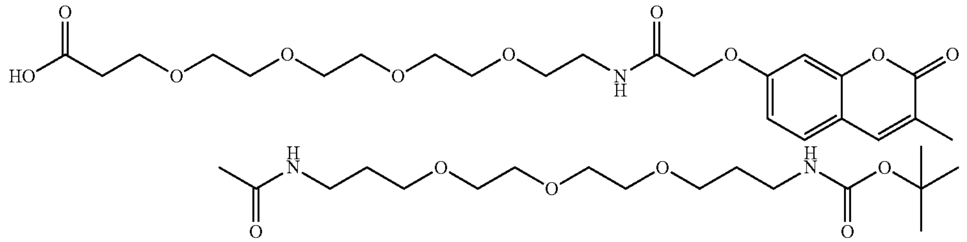

Synthesis of 1-((3-((3-(2-(2-(3-aminopropoxy) ethoxy)ethoxy)-propyl)carbamoyl)-2-oxo-2H-chromen-7-yl)oxy)-2-oxo-6,9,12,15-tetraoxa-3-azaoctadecan-18-oic acid (1:1)

1-((3-((2,2-dimethyl-4-oxo-3,9,12,15-tetraoxa-5-azaoctadecan-18-yl)carbamoyl)-2-oxo-2H-chromen-7-yl)oxy)-2-oxo-6,9,12,15-tetraoxa-3-azaoctadecan-18-oic acid (7.42 g, 9.12 mmol) was dissolved in 50 ml 35% TFA/DCM and stirred at r.t until the reaction was complete by HPLC (approximately 4 hr). The reaction was then concentrated under vacuum, azeotroped 3× with toluene and dried overnight under high vacuum to give 7.92 g of the 2,2,2-trifluoroacetic acid salt of 1-((3-((3-(2-(2-(3-aminopropoxy) ethoxy)ethoxy)propyl)carbamoyl)-2-oxo-2H-chromen-7-yl) oxy)-2-oxo-6,9,12,15-tetraoxa-3-azaoctadecan-18-oic acid (compound 22) (1:1) as a light yellow oil.

(22)

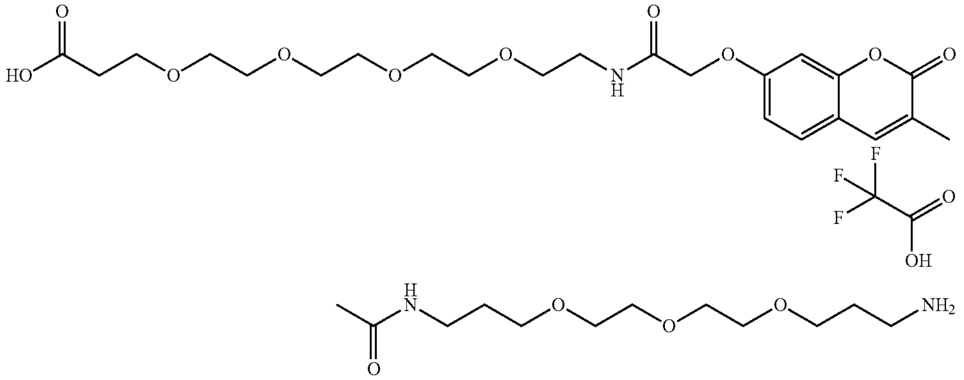

Synthesis of 1-((3-((1-(benzo[c][1,2,5]oxadiazol-5-yl)-1-oxo-6,9,12-trioxa-2-azapentadecan-15-yl)carbamoyl)-2-oxo-2H-chromen-7-yl)oxy)-2-oxo-6,9,12,15-tetraoxa-3-azaoctadecan-18-oic acid To a solution of benzo[c][1,2,5]oxadiazole-5-carboxylic acid (13 mg, 0.079 mmol) in 5 ml of dry DCM was added 1.0 M DCC in DCM (100 ul, 0.10 mmol) and N-hydroxysuccinimide (12 mg, 0.10 mmol) and the solution stirred at r.t. until the reaction was complete by HPLC (approximately 4 hr). The urea byproduct was removed by filtration and to the solution was added the 2,2,2-trifluoroacetic acid salt of 1-((3-((3-(2-(2-(3-aminopropoxy)ethoxy)ethoxy)propyl) carbamoyl)-2-oxo-2H-chromen-7-yl)oxy)-2-oxo-6,9,12,15-tetraoxa-3-azaoctadecan-18-oic acid (1:1) (82.8 mg, 0.10 mmol) and triethyl amine (30 mg, 0.30 mmol) and the reaction stirred at r.t. overnight. The reaction was concentrated, taken in minimal methanol and purified by preparative HPLC. The pure fractions were combined and lyophilized to give 42 mg (62% yield) of 1-((3-((1-(benzo[c][1,2,5]oxadiazol-5-yl)-1-oxo-6,9,12-trioxa-2-azapentadecan-15-yl)carbamoyl)-2-oxo-2H-chromen-7-yl)oxy)-2-oxo-6,9,12,15-tetraoxa-3-azaoctadecan-18-oic acid (compound 23).

(23)

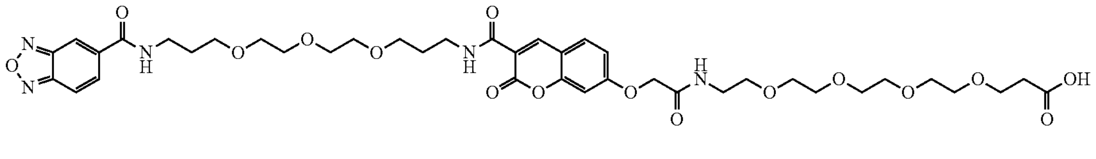

Synthesis of 2,5-dioxopyrrolidin-1-yl 1-((3-((1-(benzo[c][1,2,5]oxadiazol-5-yl)-1-oxo-6,9,12-trioxa-2-azapentadecan-15-yl)carbamoyl)-2-oxo-2H-chromen-7-yl)oxy)-2-oxo-6,9,12,15-tetraoxa-3-azaoctadecan-18-oate To a solution of 1-((3-((1-(benzo[c][1,2,5]oxadiazol-5-yl)-1-oxo-6,9,12-trioxa-2-azapentadecan-15-yl)carbamoyl)-2-oxo-2H-chromen-7-yl)oxy)-2-oxo-6,9,12,15-tetraoxa-3-azaoctadecan-18-oic acid (42 mg, 0.049 mmol) in 10 ml of dry DCM was added 1.0 M DCC in DCM (60 μL, 0.06 mmol) and N-hydroxysuccinimide (12 mg, 0.06 mmol) and the solution stirred at r.t. until the reaction was complete by HPLC (approximately 4 hr). The urea byproduct was removed by filtration, the reaction concentrated, taken in minimal methanol and purified by preparative HPLC. The pure fractions were combined and lyophilized to give 38 mg (81% yield) of 2,5-dioxopyrrolidin-1-yl 1-((3-((1-(benzo[c][1,2,5]oxadiazol-5-yl)-1-oxo-6,9,12-trioxa-2-azapentadecan-15-yl)carbamoyl)-2-oxo-2H-chromen-7-yl)oxy)-2-oxo-6,9,12,15-tetraoxa-3-azaoctadecan-18-oate (compound 24).

(24)

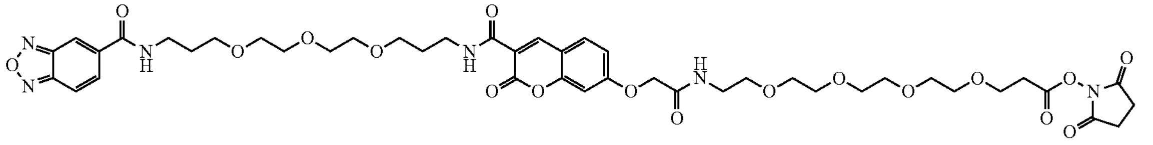

Synthesis of N-(1-(7-((21-(4-hydroxyphenyl)-2,18-dioxo-6,9,12,15-tetraoxa-3,19-diazahenicosyl)oxy)-2-oxo-2H-chromen-3-yl)-1-oxo-6,9,12-trioxa-2-aza-pentadecan-15-yl)benzo[c] [1,2,5]oxadiazole-5-carboxamide To a solution of benzo[c][1,2,5]oxadiazole-5-carboxylic acid (13 mg, 0.079 mmol) in 5 ml of dry DCM was added 1.0 M DCC in DCM (100 ul, 0.10 mmol) and N-hydroxysuccinimide (12 mg, 0.10 mmol) and the solution stirred at r.t. until the reaction was complete by HPLC (approximately 4 hr). The urea byproduct was removed by filtration and to the solution was added N-(3-(2-(2-(3-aminopropoxy)ethoxy)ethoxy)propyl)-7-((21-(4-hydroxyphenyl)-2,18-dioxo-6,9,12,15-tetraoxa-3,19-diazahenicosyl)oxy)-2-oxo-2H-chromene-3-carboxamide 2,2,2-trifluoroacetate (94.7 mg, 0.10 mmol) and triethyl amine (30 mg, 0.30 mmol) and the reaction stirred at r.t. overnight. The reaction was concentrated, taken in minimal methanol and purified by preparative HPLC. The pure fractions were combined and lyophilized to give 40 mg (52% yield) of N-(1-(7-((21-(4-hydroxyphenyl)-2,18-dioxo-6,9,12,15-tetraoxa-3,19-diazahenicosyl)oxy)-2-oxo-2H-chromen-3-yl)-1-oxo-6,9,12-trioxa-2-azapentadecan-15-yl)benzo[c][1,2,5]oxadiazole-5-carboxamide (compound 25).

(30)

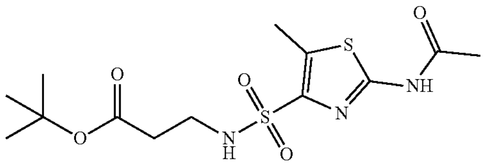

Synthesis of 3-(2-acetamido-5-methylthiazole-4-sulfonamido)propanoic acid

Tert-butyl 3-(2-acetamido-5-methylthiazole-4-sulfonamido)propanoate (1.33 g, 3.65 mmol) was taken in 30 ml of 30% TFA/DCM and the reaction stirred at r.t. until the reaction was complete by HPLC (approximately 3 hr). The reaction was then concentrated under vacuum, azeotroped 3× with toluene and dried overnight under high vacuum to give 3-(2-acetamido-5-methylthiazole-4-sulfonamido)propanoic acid (compound 31) which was used without further purification.

(25)

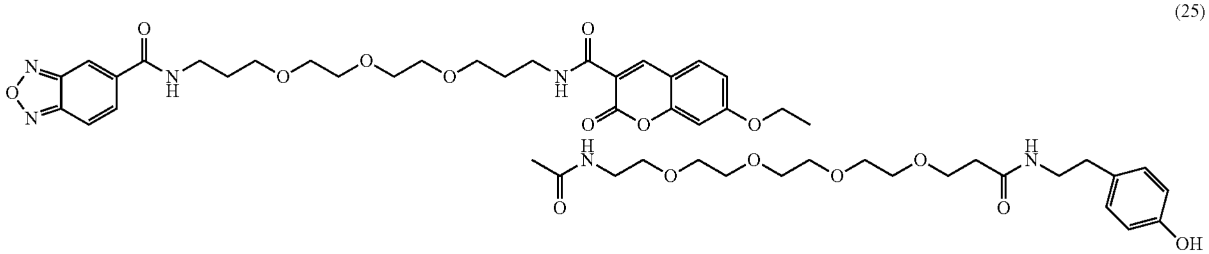

Synthesis of tert-butyl 3-(2-acetamido-5-methylthiazole-4-sulfonamido)propanoate To a solution of 2-acetamido-5-methylthiazole-4-sulfonyl chloride (1.01 g, 3.97 mmol) in 30 ml dry DCM was added tert-butyl 3-aminopropanoate hydrochloride (1.44 g, 7.94 mmol) and triethyl amine (2.21 ml, 15.88 mmol) and the reaction stirred at r.t. for 1 hour. The reaction was concentrated to approximately 5 ml then purification by silica gel chromatography (1% methanol/DCM to 15% methanol/DCM) to give 1.33 g (92% yield) of tert-butyl 3-(2-acetamido-5-methylthiazole-4-sulfonamido)propanoate (compound 30).

(31)

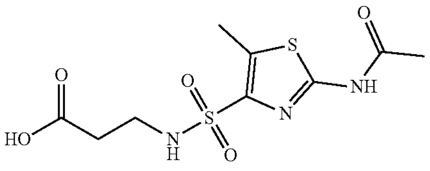

Synthesis of 2-((3-((17-(2-acetamido-5-methylthiazole-4-sulfonamido)-15-oxo-4,7,10-trioxa-14-azaheptadecyl) carbamoyl-2-oxo-2H-chromen-7-yl)oxy) acetic acid To a solution of 3-(2-acetamido-5-methylthiazole-4-sulfonamido)propanoic acid) (325 mg, 1.06 mmol) in 20 ml of dry DCM was added 1.0 M DCC in DCM (1.27 ml, 1.27 mmol) and N-hydroxysuccinimide (146 mg, 1.27 mmol) and the solution stirred at r.t. until the reaction was complete by HPLC (approximately 4 hr). The urea byproduct was removed by filtration and to the solution was added 2-((3-((3-(2-(2-(3-aminopropoxy)ethoxy)ethoxy)propyl) carbamoyl-2-oxo-2H-chromen-7-yl)oxy)acetic acid 2,2,2-trifluoroacetic acid salt (1:1) (850 mg, 1.46 mmol) and triethyl amine (442 μL, 3.17 mmol) and the reaction allowed to stir o.n. at room temperature. The crude reaction was filtered through a 0.2 micron filter and purified by preparative HPLC. The pure fractions were combined and lyophilized to give 627 mg (79% yield) of 2-((3-((17-(2-acetamido-5-methylthiazole-4-sulfonamido)-15-oxo-4,7,10-trioxa-14-azaheptadecyl) carbamoyl-2-oxo-2H-chromen-7-yl)oxy)acetic acid (compound 32).

(32)

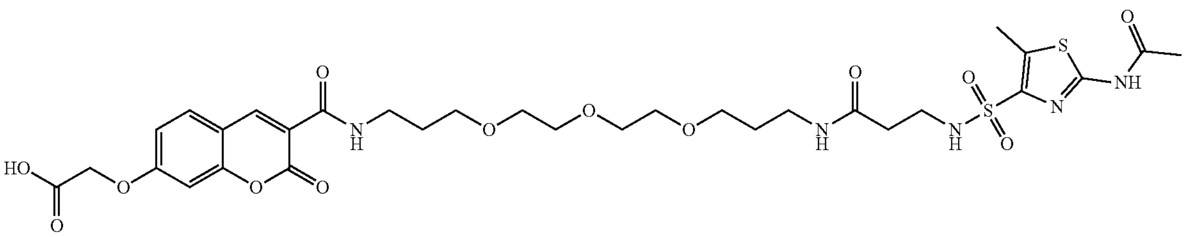

-

Synthesis of 1-((3-((17-(2-acetamido-5-methylthiazole-4-sulfonamido)-15-oxo-4,7,10-trioxa-14-azaheptadecyl)carbamoyl)-2-oxo-2H-chromen-7-yl)oxy)-2-oxo-6,9,12,15-tetraoxa-3-azaoctadecan-18-oic acid To a solution of 2-((3-((17-(2-acetamido-5-methylthiazole-4-sulfonamido)-15-oxo-4,7,10-trioxa-14-azaheptadecyl) carbamoyl-2-oxo-2H-chromen-7-yl)oxy)acetic acid (142 mg, 0.188 mmol) in 10 ml of dry DCM was added 1.0 M DCC in DCM (0.226 μL, 0.226 mmol) and N-hydroxysuccinimide (26 mg, 0.226 mmol) and the solution stirred at r.t. until the reaction was complete by HPLC (approximately 3.5 hr).). The urea byproduct was removed by filtration and to the solution was added 1-amino-3,6,9,12-tetraoxapentadecan-15-oic acid (60 mg, 0.226 mmol) and triethyl amine (79 μL, 0.564 mmol) and the reaction stirred at r.t. overnight. The reaction was concentrated, taken in minimal methanol and purified by preparative HPLC. The pure fractions were combined and lyophilized to give 158 mg (84% yield) 1-((3-((17-(2-acetamido-5-methylthiazole-4-sulfonamido)-15-oxo-4,7,10-trioxa-14-azaheptadecyl) carbamoyl)-2-oxo-2H-chromen-7-yl)oxy)-2-oxo-6,9,12,15-tetraoxa-3-azaoctadecan-18-oic acid (compound 33).

(33)

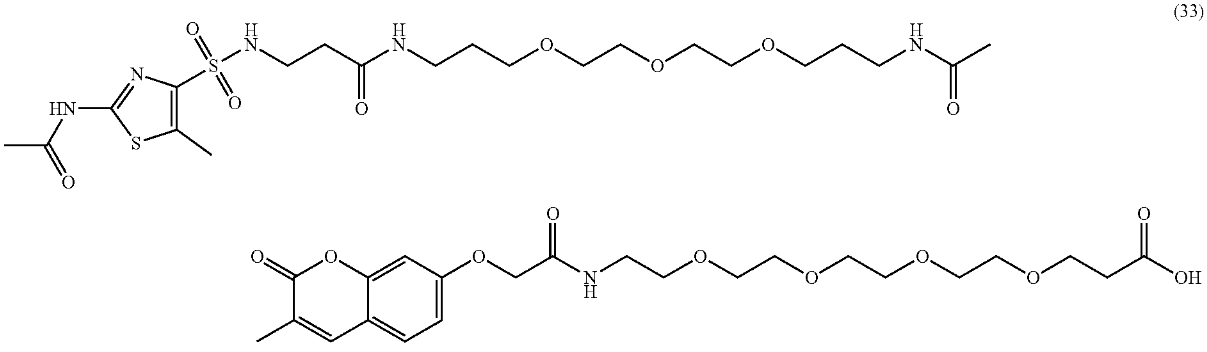

Synthesis of 2,5-dioxopyrrolidin-1-yl 1-((3-((17-(2-acetamido-5-methylthiazole-4-sulfonamido)-15-oxo-4,7,10-trioxa-14-azaheptadecyl)carbamoyl)-2-oxo-2H-chromen-7-yl)oxy)-2-oxo-6,9,12,15-tetraoxa-3-azaoctadecan-18-oate To a solution of 1-((3-((17-(2-acetamido-5-methylthiazole-4-sulfonamido)-15-oxo-4,7,10-trioxa-14-azaheptadecyl)carbamoyl)-2-oxo-2H-chromen-7-yl)oxy)-2-oxo-6,9,12,15-tetraoxa-3-azaoctadecan-18-oic acid (250 mg, 0.216 mmol) in 10 ml of dry DCM was added 1.0 M DCC in DCM (275 µL, 0.275 mmol) and N-hydroxysuccinimide (32 mg, 0.275 mmol) and the solution stirred at r.t. until the reaction was complete by HPLC (approximately 3 hr). The urea byproduct was removed by filtration, the reaction concentrated, taken in minimal methanol and purified by preparative HPLC. The pure fractions were combined and lyophilized to give 193 mg (83% yield) of 2,5-dioxopyrrolidin-1-yl 1-((3-((17-(2-acetamido-5-methylthiazole-4-sulfonamido)-15-oxo-4,7,10-trioxa-14-azaheptadecyl) carbamoyl)-2-oxo-2H-chromen-7-yl)oxy)-2-oxo-6,9,12,15-tetraoxa-3-azaoctadecan-18-oate (compound 34).

(34)

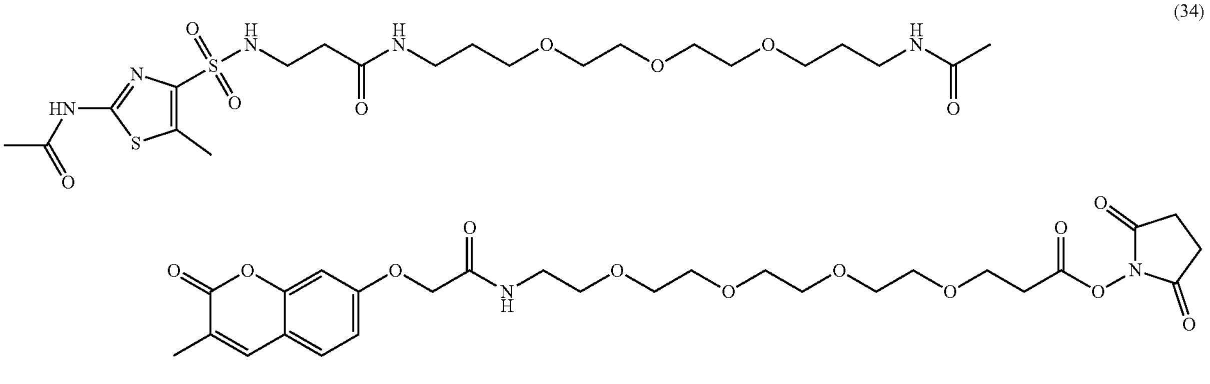

Synthesis of N-(17-(2-acetamido-5-methylthiazole-4-sulfonamido)-15-oxo-4,7,10-trioxa-14-azaheptadecyl)-7-((21-(4-hydroxyphenyl)-2,18-dioxo-6,9,12,15-tetraoxa-3,19-diazahenicosyl)oxy)-2-oxo-2H-chromene-3-carboxamide To a solution of 2,5-dioxopyrrolidin-1-yl 1-((3-((17-(2-acetamido-5-methylthiazole-4-sulfonamido)-15-oxo-4,7,10-trioxa-14-azaheptadecyl)carbamoyl)-2-oxo-2H-chromen-7-yl)oxy)-2-oxo-6,9,12,15-tetraoxa-3-azaoctadecan-18-oate (50 mg, 0.045 mmol) in 5 ml dry DCM was added tyramine (8 mg, 0.059 mmol) and triethyl amine (19 µL, 0.135 mmol) and the reaction stirred at r.t. overnight. The crude reaction was filtered through a 0.2 micron filter and purified by preparative HPLC. The pure fractions were combined and lyophilized to give 43 mg (86% yield)N-(17-(2-acetamido-5-methylthiazole-4-sulfonamido)-15-oxo-4,7,10-trioxa-14-azaheptadecyl)-7-((21-(4-hydroxyphenyl)-2,18-dioxo-6,9,12,15-tetraoxa-3,19-diazahenicosyl)oxy)-2-oxo-2H-chromene-3-carboxamide (compound 35).

(35)

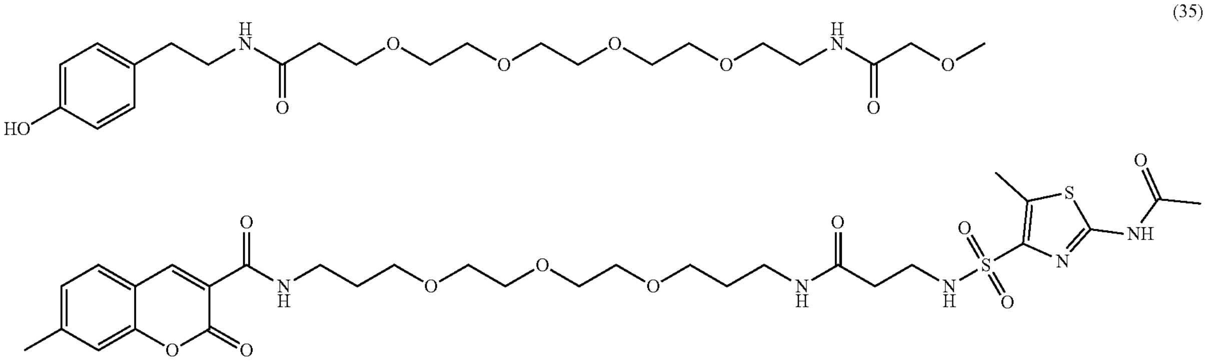

Synthesis of 2-((3-((17-(2,5-dioxo-2,5-dihydro-1H-pyrrol-1-yl)-15-oxo-4,7,10-trioxa-14-azaheptadecyl) carbamoyl)-2-oxo-2H-chromen-7-yl)oxy)acetic acid To a solution of 3-(2,5-dioxo-2,5-dihydro-1H-pyrrol-1-yl) propanoic acid (500 mg, 2.96 mmol) in 20 ml of dry DCM was added 1.0 M DCC in DCM (3.55 ml, 3.55 mmol) and N-hydroxysuccinimide (408 mg, 3.55 mmol) and the solution stirred at r.t. until the reaction was complete by HPLC (approximately 1 hr). The urea byproduct was removed by filtration and to the solution was added 2-((3-((3-(2-(2-(3-aminopropoxy)ethoxy)ethoxy)propyl)carbamoyl)-2-oxo-2H-chromen-7-yl)oxy)acetic acid 2,2,2-trifluoroacetic acid salt(1:1) (1.20 g, 2.00 mmol) and triethyl amine (700 μL, 5.00 mmol) and the reaction allowed to stir o.n. at room temperature. The crude reaction was filtered through a 0.2 micron filter and purified by preparative HPLC. The pure fractions were combined and lyophilized to give 889 mg (72% yield) of 2-((3-((17-(2,5-dioxo-2,5-dihydro-1H-pyrrol-1-yl)-15-oxo-4,7,10-trioxa-14-azaheptadecyl)carbamoyl)-2-oxo-2H-chromen-7-yl)oxy)acetic acid (compound 40).

To a solution of 2-((3-((17-(2,5-dioxo-2,5-dihydro-1H-pyrrol-1-yl)-15-oxo-4,7,10-trioxa-14-azaheptadecyl)carbamoyl)-2-oxo-2H-chromen-7-yl)oxy)acetic acid (573 mg, 0.928 mmol) in 20 ml dry DCM was added 1.0 M DCC in DCM (1.20 ml, 01.20 mmol) and N-hydroxysuccinimide (139 mg, 01.26 mmol) and the solution stirred at r.t. until the reaction was complete by HPLC (approximately 3 hr). The urea byproduct was removed by filtration and to the solution was added 1-amino-3,6,9,12-tetraoxapentadecan-15-oic acid (369 mg, 1.80 mmol) and triethyl amine (388 μL, 0.564 mmol) and the reaction stirred at r.t. overnight. The reaction was concentrated, taken in minimal methanol and purified by preparative HPLC. The pure fractions were combined and lyophilized to give 586 mg (73% yield) of 1-((3-((17-(2,5-dioxo-2,5-dihydro-1H-pyrrol-1-yl)-15-oxo-4,7,10-trioxa-14-azaheptadecyl)carbamoyl)-2-oxo-2H-chromen-7-yl)oxy)-2-oxo-6,9,12,15-tetraoxa-3-azaoctadecan-18-oic acid (compound 41).

(40)

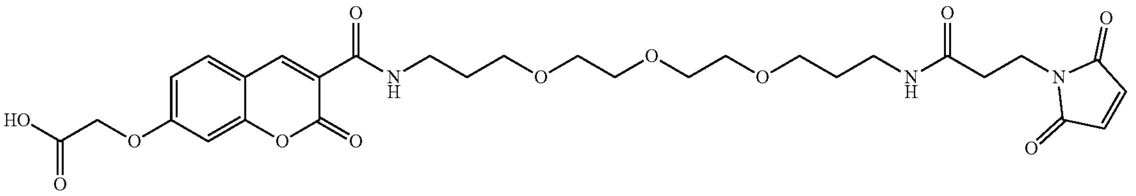

Synthesis of 1-((3-((17-(2,5-dioxo-2,5-dihydro-1H-pyrrol-1-yl)-15-oxo-4,7,10-trioxa-14-azaheptadecyl) carbamoyl)-2-oxo-2H-chromen-7-yl)oxy)-2-oxo-6,9,12,15-tetraoxa-3-azaoctadecan-18-oic acid To a solution of 2-((3-((17-(2,5-dioxo-2,5-dihydro-1H-pyrrol-1-yl)-15-oxo-4,7,10-trioxa-14-azaheptadecyl)carbamoyl)-2-oxo-2H-chromen-7-yl)oxy)acetic acid (573 mg, 0.928 mmol) in 20 ml dry DCM was added 1.0 M DCC in DCM (1.20 ml, 01.20 mmol) and N-hydroxysuccinimide (139 mg, 01.26 mmol) and the solution stirred at r.t. until the reaction was complete by HPLC (approximately 3 hr). The urea byproduct was removed by filtration and to the solution was added 1-amino-3,6,9,12-tetraoxapentadecan-15-oic acid (369 mg, 1.80 mmol) and triethyl amine (388 μL, 0.564 mmol) and the reaction stirred at r.t. overnight. The reaction was concentrated, taken in minimal methanol and purified by preparative HPLC. The pure fractions were combined and lyophilized to give 586 mg (73% yield) of 1-((3-((17-(2,5-dioxo-2,5-dihydro-1H-pyrrol-1-yl)-15-oxo-4,7,10-trioxa-14-azaheptadecyl)carbamoyl)-2-oxo-2H-chromen-7-yl)oxy)-2-oxo-6,9,12,15-tetraoxa-3-azaoctadecan-18-oic acid (compound 41).

Synthesis of 2,5-dioxopyrrolidin-1-yl 1-((3-((17-(2,5-dioxo-2,5-dihydro-1H-pyrrol-1-yl)-15-oxo-4,7,10-trioxa-14-azaheptadecyl)carbamoyl)-2-oxo-2H-chromen-7-yl)oxy)-2-oxo-6,9,12,15-tetraoxa-3-azaoctadecan-18-oate To a solution of 1-((3-((17-(2,5-dioxo-2,5-dihydro-1H-pyrrol-1-yl)-15-oxo-4,7,10-trioxa-14-azaheptadecyl)carbamoyl)-2-oxo-2H-chromen-7-yl)oxy)-2-oxo-6,9,12,15-tetraoxa-3-azaoctadecan-18-oic acid (367 mg, 0.424 mmol) in 5 ml of dry DMF was added DSC (bis(2,5-dioxopyrrolidin-1-yl) carbonate) (120 mg, 0.467) and DMAP (78 mg, 0.636 mmol) and the solution stirred at r.t. until the reaction was complete by HPLC (approximately 30 min). The crude reaction was filtered through a 0.2 micron filter and purified by preparative HPLC. The pure fractions were combined and lyophilized to give 351 mg (86% yield) of 2,5-dioxopyrrolidin-1-yl 1-((3-((17-(2,5-dioxo-2,5-dihydro-1H-pyrrol-1-yl)-15-oxo-4,7,10-trioxa-14-azaheptadecyl)carbamoyl)-2-oxo-2H-chromen-7-yl)oxy)-2-oxo-6,9,12,15-tetraoxa-3-azaoctadecan-18-oate (compound 42).

(41)

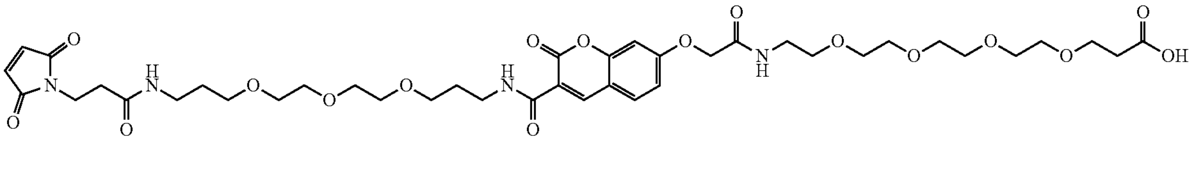

(42)

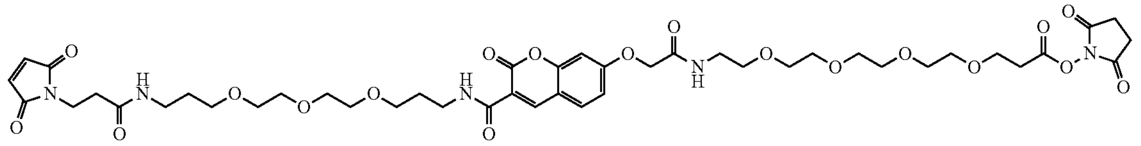

Synthesis of N-(1-(7-amino-4-methyl-2-oxo-2H-chromen-3-yl)-2-oxo-7,10,13-trioxa-3-azahexadecan-16-yl)benzo[c] [1,2,5]oxadiazole-5-carboxamide To a solution of 2-(7-amino-4-methyl-2-oxo-2H-chromen-3-yl)acetic acid (152 mg, 0.652 mmol) in 5 ml dry DMF was added DSC (176 mg, 0.685) and DMAP (120 mg, 0.978 mmol) and the solution stirred at r.t. until the reaction was complete by HPLC (approximately 30 min). N-(3-(2-(2-(3-aminopropoxy)ethoxy)ethoxy)propyl)benzo[c][1,2,5]oxadiazole-5-carboxamide 2,2,2-trifluoroacetate (360 mg, 0.749 mmol) and triethyl amine (273 μL, 1.956 mmol) were then added and the reaction stirred at r.t. overnight. The reaction was concentrated, taken in minimal methanol and purified by preparative HPLC. The pure fractions were combined and lyophilized to give 269 mg (71% yield) of N-(1-(7-amino-4-methyl-2-oxo-2H-chromen-3-yl)-2-oxo-7,10,13-trioxa-3-azahexadecan-16-yl)benzo[c][1,2,5]oxadiazole-5-carboxamide (compound 50).

(50)

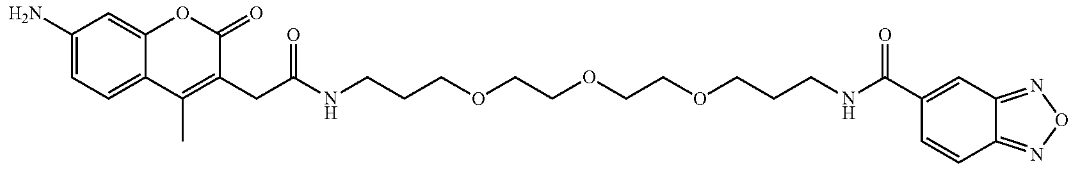

Synthesis of tert-butyl 2-((3-(1-(benzo[c][1,2,5]oxadiazol-5-yl)-1,17-dioxo-6,9,12-trioxa-2,16-diazaoctadecan-18-yl)-4-methyl-2-oxo-2H-chromen-7-yl)amino)acetate To a solution of N-(1-(7-amino-4-methyl-2-oxo-2H-chromen-3-yl)-2-oxo-7,10,13-trioxa-3-azahexadecan-16-yl)benzo[c][1,2,5]oxadiazole-5-carboxamide (200 mg, 0.344 mmol) in 10 ml dry DMF was added tert-butyl 2-bromoacetate (67 mg, 0.344 mmol) and triethyl amine (144 μL, 1.03 mmol) and the reaction stirred at 60 Co overnight. The reaction was diluted with 50 ml of DCM and washed 2× with 50 ml of saturated sodium bicarbonate then 2× with 50 ml of brine. The organic phase was concentrated to approximately 5 ml then purification by silica gel chromatography (2% methanol/DCM to 16% methanol/DCM) to give 218 mg (91% yield) of tert-butyl 2-((3-(1-(benzo[c][1,2,5]oxadiazol-5-yl)-1,17-dioxo-6,9,12-trioxa-2,16-diazaoctadecan-18-yl)-4-methyl-2-oxo-2H-chromen-7-yl)amino)acetate (51).

(51)

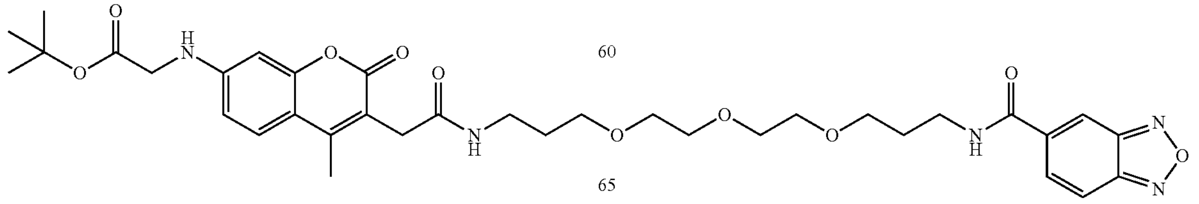

Synthesis of 2-((3-(1-(benzo[c][1,2,5]oxadiazol-5-yl)-1,17-dioxo-6,9,12-trioxa-2,16-diazaoctadecan-18-yl)-4-methyl-2-oxo-2H-chromen-7-yl)amino) acetic acid Tert-butyl 2-((3-(1-(benzo[c][1,2,5]oxadiazol-5-yl)-1,17-dioxo-6,9,12-trioxa-2,16-diazaoctadecan-18-yl)-4-methyl-2-oxo-2H-chromen-7-yl)amino)acetate (218 mg, 0.313 mmol) was taken in 20 ml of 30% TFA/DCM and the reaction stirred at r.t. until the reaction was complete by HPLC (approximately 4.5 hr). The reaction was then concentrated under vacuum, azeotroped 3× with toluene and dried overnight under high vacuum to give 220 mg (quantitative yield) 2-((3-(1-(benzo[c][1,2,5]oxadiazol-5-yl)-1,17-dioxo-6,9,12-trioxa-2,16-diazaoctadecan-18-yl)-4-methyl-2-oxo-2H-chromen-7-yl)amino)acetic acid which was used without further purification (52).

(52)

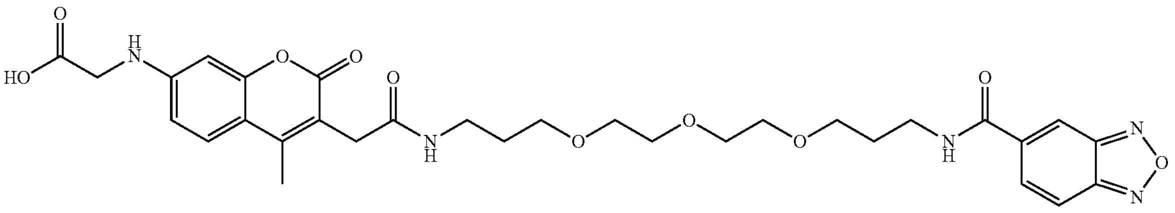

Synthesis of 1-((3-(1-(benzo[c][1,2,5]oxadiazol-5-yl)-1,17-dioxo-6,9,12-trioxa-2,16-diazaoctadecan-18-yl)-4-methyl-2-oxo-2H-chromen-7-yl)amino)-2-oxo-6,9,12,15-tetraoxa-3-azaoctadecan-18-oic acid To a solution of 2-((3-(1-(benzo[c][1,2,5]oxadiazol-5-yl)-1,17-dioxo-6,9,12-trioxa-2,16-diazaoctadecan-18-yl)-4-methyl-2-oxo-2H-chromen-7-yl)amino)acetic acid (220 mg, 0.345 mmol) in 10 ml dry DCM was added 1.0 M DCC in DCM (413 μL, 0.413 mmol) and N-hydroxysuccinimide (47 mg, 0.413 mmol) and the solution stirred at r.t. until the reaction was complete by HPLC (approximately 4 hr). The urea byproduct was removed by filtration and to the solution was added 1-amino-3,6,9,12-tetraoxapentadecan-15-oic acid (182 mg, 0.686 mmol) and triethyl amine (200 μL, 1.44 mmol) and the reaction stirred at r.t. overnight. The reaction was concentrated, taken in minimal methanol and purified by preparative HPLC. The pure fractions were combined and lyophilized to give 517 mg (85% yield) of 1-((3-(1-(benzo[c][1,2,5]oxadiazol-5-yl)-1,17-dioxo-6,9,12-trioxa-2,16-diazaoctadecan-18-yl)-4-methyl-2-oxo-2H-chromen-7-yl)amino)-2-oxo-6,9,12,15-tetraoxa-3-azaoctadecan-18-oic acid (compound 53).

(53)

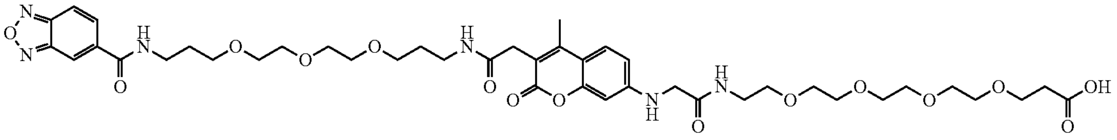

Synthesis of 2,5-dioxopyrrolidin-1-yl 1-((3-(1-(benzo[c][1,2,5]oxadiazol-5-yl)-1,17-dioxo-6,9,12-trioxa-2,16-diazaoctadecan-18-yl)-4-methyl-2-oxo-2H-chromen-7-yl)amino)-2-oxo-6,9,12,15-tetraoxa-3-azaoctadecan-18-oate To a solution of 1-((3-(1-(benzo[c][1,2,5]oxadiazol-5-yl)-1,17-dioxo-6,9,12-trioxa-2,16-diazaoctadecan-18-yl)-4-methyl-2-oxo-2H-chromen-7-yl)amino)-2-oxo-6,9,12,15-tetraoxa-3-azaoctadecan-18-oic acid (120 mg, 0.135 mmol) in 10 ml of dry DCM was added 1.0 M DCC in DCM (156 μL, 0.156 mmol) and N-hydroxysuccinimide (18 mg, 0.156 mmol) and the solution stirred at r.t. until the reaction was complete by HPLC (approximately 5 hr). The urea byproduct was removed by filtration, the reaction concentrated, taken in minimal methanol and purified by preparative HPLC. The pure fractions were combined and lyophilized to give 109 mg (82% yield) of 2,5-dioxopyrrolidin-1-yl 1-((3-(1-(benzo[c][1,2,5]oxadiazol-5-yl)-1,17-dioxo-6,9,12-trioxa-2,16-diazaoctadecan-18-yl)-4-methyl-2-oxo-2H-chromen-7-yl)amino)-2-oxo-6,9,12,15-tetraoxa-3-azaoctadecan-18-oate (compound 54).

Synthesis of 2-amino-6-(7-(diethylamino)-2-oxo-2H-chromene-3-carboxamido)hexanoic acid 2-((tert-butoxycarbonyl)amino)-6-(7-(diethylamino)-2-oxo-2H-chromene-3-carboxamido) hexanoic acid (2.62 g, 5.36 mmol) was dissolved in 50 ml 35% TFA/DCM and stirred at r.t until the reaction was complete by HPLC (approximately 3 hr). The reaction was then concentrated under vacuum, azeotroped 3× with toluene and dried overnight under high vacuum to give the 2,2,2-trifluoroacetic acid salt of 2-amino-6-(7-(diethylamino)-2-oxo-2H-chromene-3-carboxamido)hexanoic acid (compound 61) (1:1) which was used without further purification.

(54)

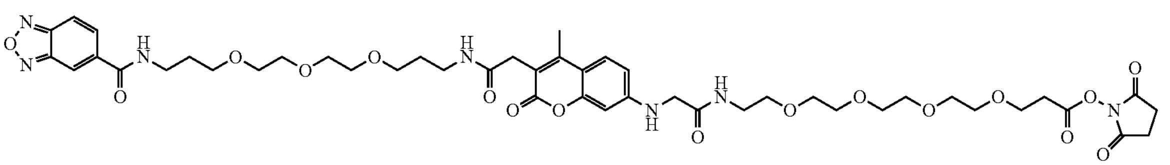

Synthesis of 2-((tert-butoxycarbonyl)amino)-6-(7-(diethylamino)-2-oxo-2H-chromene-3-carboxamido) hexanoic acid To a solution of 7-(diethylamino)-2-oxo-2H-chromene-3-carboxylic acid (1.57 g, 6.02 mmol) in 25 ml of dry DCM was added 1.0 M DCC in DCM 7.22 ml, 7.22 mmol) and N-hydroxysuccinimide (830 mg, 7.22 mmol) and the solution stirred at r.t. until the reaction was complete by HPLC (approximately 4 hr). The urea byproduct was removed by filtration and to the solution was added 6-amino-2-((tert-butoxycarbonyl)amino)hexanoic acid (1.77 g, 0.686 mmol) and triethyl amine (2.52 ml, 18.06 mmol) and the reaction stirred at r.t. overnight. The reaction was diluted with 50 ml of DCM and washed 2× with 50 ml of saturated sodium bicarbonate then 2× with 50 ml of brine. The organic phase was concentrated to approximately 5 ml then purification by silica gel chromatography (3% methanol/DCM to 16% methanol/DCM) to give 2.62 g (89% yield) of 2-((tert-butoxycarbonyl)amino)-6-(7-(diethylamino)-2-oxo-2H-chromene-3-carboxamido)hexanoic acid (compound 60).

(60)

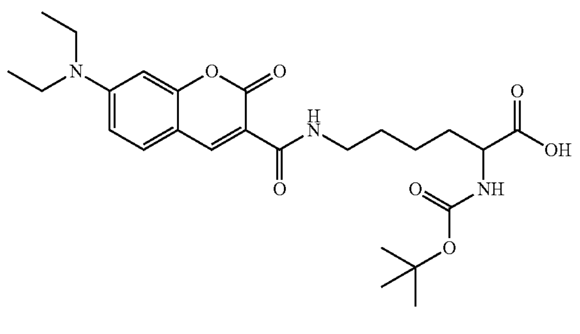

(61)

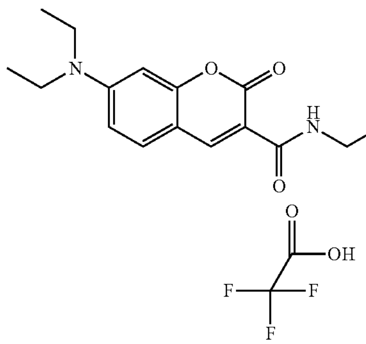

Synthesis of 1-(2-acetamido-5-methylthiazole-4-sulfonamido)-3,6,9,12,15,18,21,24-octaoxaheptacosan-27-oic acid To a solution of 2-acetamido-5-methylthiazole-4-sulfonyl chloride (246 mg, 0.967 mmol) in 15 ml dry DCM was added 1-amino-3,6,9,12,15,18,21,24-octaoxaheptacosan-27-oic acid (507 mg, 0.967 mmol) and triethyl amine (350 μL, 2.50 mmol) and the reaction stirred at r.t. overnight. The reaction was diluted with 20 ml of DCM and washed 2× with 30 ml of saturated sodium bicarbonate then 2× with 30 ml of brine. The organic phase was concentrated to approximately 5 ml then purification by silica gel chromatography (4% methanol/DCM to 15% methanol/DCM) to give 530 mg (83% yield) of 1-(2-acetamido-5-methylthiazole-4-sulfonamido)-3,6,9,12,15,18,21,24-octaoxaheptacosan-27-oic acid (compound 62).

(62)

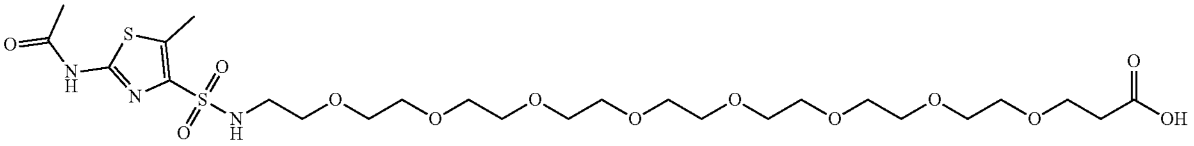

Synthesis of 2,5-dioxopyrrolidin-1-yl 1-(2-acetamido-5-methylthiazole-4-sulfonamido)-3,6,9,12,15,18,21,24-octaoxaheptacosan-27-oate To a solution of 1-(2-acetamido-5-methylthiazole-4-sulfonamido)-3,6,9,12,15,18,21,24-octaoxaheptacosan-27-oic acid (530 mg, 0.803 mmol) in 20 ml of dry DCM was added 1.0 M DCC in DCM (964 μL, 0.964 mmol) and N-hydroxysuccinimide (111 mg, 0.964 mmol) and the solution stirred at r.t. until the reaction was complete by HPLC (approximately 3 hr). The urea byproduct was removed by filtration, the reaction concentrated, taken in minimal methanol and purified by preparative HPLC. The pure fractions were combined and lyophilized to give 510 mg (84% yield) of 2,5-dioxopyrrolidin-1-yl 1-(2-acetamido-5-methylthiazole-4-sulfonamido)-3,6,9,12,15,18,21,24-octaoxaheptacosan-27-oate (compound 63).

(63)

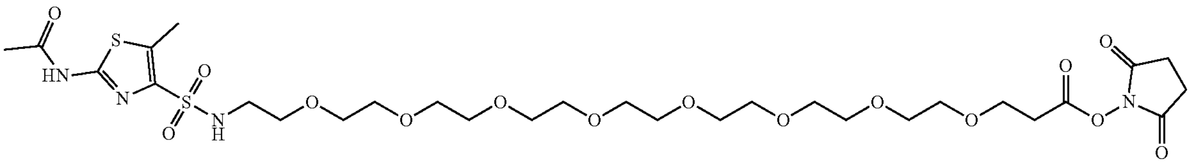

[Synthesis of 1-(2-acetamido-5-methylthiazole-4-sulfonamido)-29-(4-(7-(diethylamino)-2-oxo-2H-chromene-3-carboxamido)butyl)-27-oxo-3,6,9,12,15,18,21,24-octaoxa-28-azatriacontan-30-oic acid To a solution of 2,5-dioxopyrrolidin-1-yl 1-(2-acetamido-5-methylthiazole-4-sulfonamido)-3,6,9,12,15,18,21,24-octaoxaheptacosan-27-oate (608 mg, 0.803 mmol) in 25 ml of dry DCM was added the 2,2,2-trifluoroacetic acid salt of 2-amino-6-(7-(diethylamino)-2-oxo-2H-chromene-3-carboxamido)hexanoic acid (1:1) (485, 0.9636 mmol) and triethyl amine (336 μL, 2.409 mmol) and the solution stirred at r.t. until the reaction was complete by HPLC (approximately 6 hr). The reaction was diluted with 30 ml of DCM and washed 2× with 40 ml of saturated sodium bicarbonate then 2× with 40 ml of brine. The organic phase was concentrated, taken in minimal methanol and purified by preparative HPLC. The pure fractions were combined and lyophilized to give 637 mg (77% yield) of 1-(2-acetamido-5-methylthiazole-4-sulfonamido)-29-(4-(7-(diethylamino)-2-oxo-2H-chromene-3-carboxamido)butyl)-27-oxo-3,6,9,12,15,18,21,24-octaoxa-28-azatriacontan-30-oic acid (compound 64).

(64)

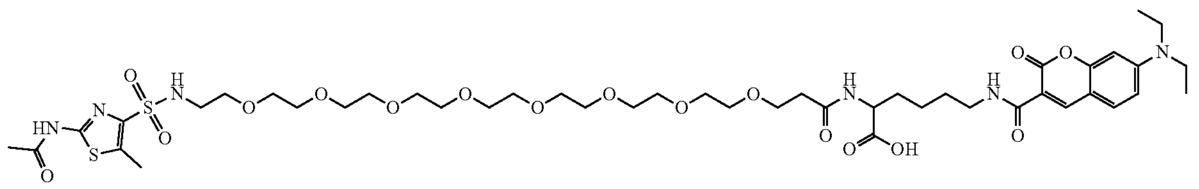

Synthesis of 1-(2-acetamido-5-methylthiazole-4-sulfonamido)-29-(4-(7-(diethylamino)-2-oxo-2H-chromene-3-carboxamido)butyl)-27,30-dioxo-3,6,9,12,15,18,21,24,34,37,40,43-dodecaoxa-28,31-diazahexatetracontan-46-oic acid To a solution of 1-(2-acetamido-5-methylthiazole-4-sulfonamido)-29-(4-(7-(diethylamino)-2-oxo-2H-chromene-3-carboxamido)butyl)-27-oxo-3,6,9,12,15,18,21,24-octaoxa-28-azatriacontan-30-oic acid (310 mg, 0.301 mmol) in 20 ml of dry DCM was added 1.0 M DCC in DCM (450 μL, 0.450 mmol) and N-hydroxysuccinimide (52 mg, 0.450 mmol) and the solution stirred at r.t. until the reaction was complete by HPLC (approximately 3.5 hr). The urea byproduct was removed by filtration and to the reaction added 1-amino-3,6,9,12-tetraoxapentadecan-15-oic acid (96 mg, 0.361 mmol) and triethyl amine (126 μL, 0.903 mmol) and the reaction stirred at r.t. overnight. The reaction was diluted with 30 ml of DCM and washed 2× with 50 ml of saturated sodium bicarbonate then 2× with 50 ml of brine. The organic phase was concentrated, taken in minimal methanol and purified by preparative HPLC. The pure fractions were combined and lyophilized to give 327 mg (97% yield) of 1-(2-acetamido-5-methylthiazole-4-sulfonamido)-29-(4-(7-(diethylamino)-2-oxo-2H-chromene-3-carboxamido)butyl)-27,30-dioxo-3,6,9,12,15,18,21,24,34,37,40,43-dodecaoxa-28,31-diazahexatetracontan-46-oic acid (compound 65).

Synthesis of 2,5-dioxopyrrolidin-1-yl 1-(2-acetamido-5-methylthiazole-4-sulfonamido)-29-(4-(7-(diethylamino)-2-oxo-2H-chromene-3-carboxamido)butyl)-27,30-dioxo-3,6,9,12,15,18,21,24,34,37,40,43-dodecaoxa-28,31-diazahexatetracontan-46-oate To a solution of 1-(2-acetamido-5-methylthiazole-4-sulfonamido)-29-(4-(7-(diethylamino)-2-oxo-2H-chromene-3-carboxamido)butyl)-27,30-dioxo-3,6,9,12,15,18,21,24,34,37,40,43-dodecaoxa-28,31-diazahexatetracontan-46-oic acid (178 mg, 0.139 mmol) in 15 ml of dry DCM was added 1.0 M DCC in DCM (167 μL, 0.167 mmol) and N-hydroxysuccinimide (19 mg, 0.167 mmol) and the solution stirred at r.t. until the reaction was complete by HPLC (approximately 4.5 hr). The urea byproduct was removed by filtration, the reaction concentrated, taken in minimal methanol and purified by preparative HPLC. The pure fractions were combined and lyophilized to give 168 mg (88% yield) of 2,5-dioxopyrrolidin-1-yl 1-(2-acetamido-5-methylthiazole-4-sulfonamido)-29-(4-(7-(diethylamino)-2-oxo-2H-chromene-3-carboxamido)butyl)-27,30-dioxo-3,6,9,12,15,18,21,24,34,37,40,43-dodecaoxa-28,31-diazahexatetracontan-46-oate (compound 66).

(65)

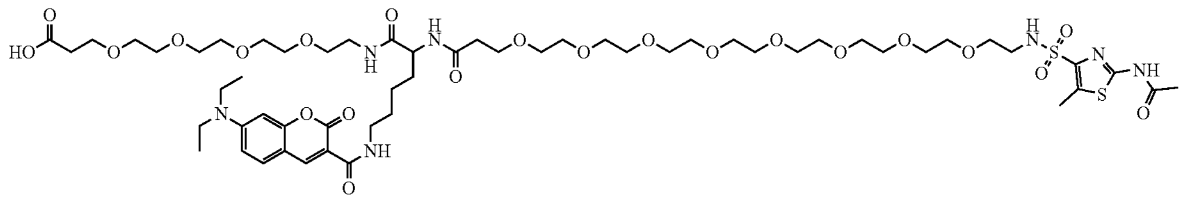

65

(66)

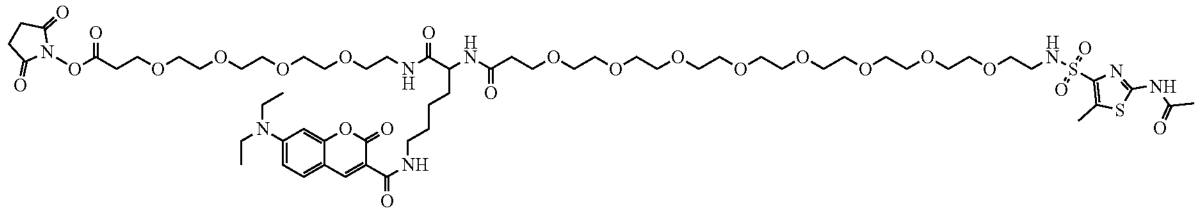

Automation

The multiplex assays and methods may be automated and may be combined with a specimen processing apparatus. The specimen processing apparatus can be an automated apparatus, such as the BENCHMARK XT instrument and SYMPHONY instrument sold by Ventana Medical Systems, Inc. Ventana Medical Systems, Inc. is the assignee of a number of United States patents disclosing systems and methods for performing automated analyses, including U.S. Pat. Nos. 5,650,327, 5,654,200, 6,296,809, 6,352,861, 6,827,901 and 6,943,029, and U.S. Published Patent Application Nos. 2003/0211630 and 2004/0052685, each of which is incorporated herein by reference in its entirety. Alternatively, specimens can be manually processed.

The specimen processing apparatus can apply fixatives to the specimen. Fixatives can include cross-linking agents (such as aldehydes, e.g., formaldehyde, paraformaldehyde, and glutaraldehyde, as well as non-aldehyde cross-linking agents), oxidizing agents (e.g., metallic ions and complexes, such as osmium tetroxide and chromic acid), protein-denaturing agents (e.g., acetic acid, methanol, and ethanol), fixatives of unknown mechanism (e.g., mercuric chloride, acetone, and picric acid), combination reagents (e.g., Carnoy's fixative, methacarn, Bouin's fluid, B5 fixative, Rossman's fluid, and Gendre's fluid), microwaves, and miscellaneous fixatives (e.g., excluded volume fixation and vapor fixation).

If the specimen is a sample embedded in paraffin, the sample can be deparaffinized with the specimen processing apparatus using appropriate deparaffinizing fluid(s). After the waste remover removes the deparaffinizing fluid(s), any number of substances can be successively applied to the specimen. The substances can be for pretreatment (e.g., protein-crosslinking, expose nucleic acids, etc.), denaturation, hybridization, washing (e.g., stringency wash), detection (e.g., link a visual or marker molecule to a probe), amplifying (e.g., amplifying proteins, genes, etc.), counterstaining, coverslipping, or the like.

The specimen processing apparatus can apply a wide range of substances to the specimen. The substances include, without limitation, stains, probes, reagents, rinses, and/or conditioners. The substances can be fluids (e.g., gases, liquids, or gas/liquid mixtures), or the like. The fluids can be solvents (e.g., polar solvents, non-polar solvents, etc.), solutions (e.g., aqueous solutions or other types of solutions), or the like. Reagents can include, without limitation, stains, wetting agents, antibodies (e.g., monoclonal antibodies, polyclonal antibodies, etc.), antigen recovering fluids (e.g., aqueous- or non-aqueous-based antigen retrieval solutions, antigen recovering buffers, etc.), or the like. Probes can be an isolated nucleic acid or an isolated synthetic oligonucleotide, attached to a detectable label or reporter molecule. Labels can include radioactive isotopes, enzyme substrates, co-factors, ligands, chemiluminescent or fluorescent agents, haptens, and enzymes.

After the specimens are processed, a user can transport specimen-bearing slides to the imaging apparatus. The imaging apparatus used here is a brightfield imager slide scanner. One brightfield imager is the iScan Coreo™ brightfield scanner sold by Ventana Medical Systems, Inc. In automated embodiments, the imaging apparatus is a digital pathology device as disclosed in International Patent Application No.: PCT/US2010/002772 (Patent Publication No.: WO/2011/049608) entitled IMAGING SYSTEM AND TECHNIQUES or disclosed in U.S. Patent Publication No. 2014/0178169 filed on Sep. 9, 2011, entitled IMAGING SYSTEMS, CASSETTES, AND METHODS OF USING THE SAME.

Counterstaining

Counterstaining is a method of post-treating the samples after they have already been stained with agents to detect one or more targets, such that their structures can be more readily visualized under a microscope. For example, a counterstain is optionally used prior to coverslipping to render the immunohistochemical stain more distinct. Counterstains differ in color from a primary stain. Numerous counterstains are well known, such as hematoxylin, eosin, methyl green, methylene blue, Giemsa, Alcian blue, and Nuclear Fast Red. DAPI (4',6-diamidino-2-phenylindole) is a fluorescent stain that may be used.

In some examples, more than one stain can be mixed together to produce the counterstain. This provides flexibility and the ability to choose stains. For example, a first stain, can be selected for the mixture that has a particular attribute, but yet does not have a different desired attribute. A second stain can be added to the mixture that displays the missing desired attribute. For example, toluidine blue, DAPI, and pontamine sky blue can be mixed together to form a counterstain.

Imaging

Certain aspects, or all, of the disclosed embodiments can be automated, and facilitated by computer analysis and/or image analysis system. In some applications, precise color or fluorescence ratios are measured. In some embodiments, light microscopy is utilized for image analysis. Certain disclosed embodiments involve acquiring digital images. This can be done by coupling a digital camera to a microscope. Digital images obtained of stained samples are analyzed using image analysis software. Color or fluorescence can be measured in several different ways. For example, color can be measured as red, blue, and green values; hue, saturation, and intensity values; and/or by measuring a specific wavelength or range of wavelengths using a spectral imaging camera. The samples also can be evaluated qualitatively and semi-quantitatively. Qualitative assessment includes assessing the staining intensity, identifying the positively-staining cells and the intracellular compartments involved in staining, and evaluating the overall sample or slide quality. Separate evaluations are performed on the test samples and this analysis can include a comparison to known average values to determine if the samples represent an abnormal state.

Samples and Targets

Samples include biological components and generally are suspected of including one or more target molecules of interest. Target molecules can be on the surface of cells and the cells can be in a suspension, or in a tissue section. Target molecules can also be intracellular and detected upon cell lysis or penetration of the cell by a probe. One of ordinary skill in the art will appreciate that the method of detecting target molecules in a sample will vary depending upon the type of sample and probe being used. Methods of collecting and preparing samples are known in the art.

Samples for use in the embodiments of the method and with the composition disclosed herein, such as a tissue or other biological sample, can be prepared using any method known in the art by of one of ordinary skill. The samples can be obtained from a subject for routine screening or from a subject that is suspected of having a disorder, such as a genetic abnormality, infection, or a neoplasia. The described embodiments of the disclosed method can also be applied to samples that do not have genetic abnormalities, diseases, disorders, etc., referred to as "normal" samples. Such normal samples are useful, among other things, as controls for comparison to other samples. The samples can be analyzed for many different purposes. For example, the samples can be used in a scientific study or for the diagnosis of a suspected malady, or as prognostic indicators for treatment success, survival, etc.

Samples can include multiple targets that can be specifically bound by a probe or reporter molecule. The targets can be nucleic acid sequences or proteins. In some examples, the target is a protein or nucleic acid molecule from a pathogen, such as a virus, bacteria, or intracellular parasite, such as from a viral genome. For example, a target protein may be produced from a target nucleic acid sequence associated with (e.g., correlated with, causally implicated in, etc.) a disease.

The skilled artisan will appreciate that coumarin-based conjugates may be developed which are specific to any of the following targets:

In specific, non-limiting examples, a target protein is produced by a target nucleic acid sequence (e.g., genomic target nucleic acid sequence) associated with a neoplasm (for example, a cancer). Numerous chromosome abnormalities (including translocations and other rearrangements, amplification or deletion) have been identified in neoplastic cells, especially in cancer cells, such as B cell and T cell leukemias, lymphomas, breast cancer, colon cancer, neurological cancers and the like. Therefore, in some examples, at least a portion of the target molecule is produced by a nucleic acid sequence (e.g., genomic target nucleic acid sequence) amplified or deleted in at least a subset of cells in a sample.

In other examples, a target protein produced from a nucleic acid sequence (e.g., genomic target nucleic acid sequence) that is a tumor suppressor gene that is deleted (lost) in malignant cells. For example, the p16 region (including D9S1749, D9S1747, p16(INK4A), p14(ARF), D9S1748, p15(INK4B), and D9S1752) located on chromosome 9p21 is deleted in certain bladder cancers. Chromosomal deletions involving the distal region of the short arm of chromosome 1 (that encompasses, for example, SHGC57243, TP73, EGFL3, ABL2, ANGPTL1, and SHGC-1322), and the pericentromeric region (e.g., 19p13-19q13) of chromosome 19 (that encompasses, for example, MAN2B1, ZNF443, ZNF44, CRX, GLTSCR2, and GLTSCR1) are characteristic molecular features of certain types of solid tumors of the central nervous system.

Numerous other cytogenetic abnormalities that correlate with neoplastic transformation and/or growth are known to those of ordinary skill in the art. Target proteins that are produced by nucleic acid sequences (e.g., genomic target nucleic acid sequences), which have been correlated with neoplastic transformation and which are useful in the disclosed methods, also include the EGFR gene (7p12; e.g., GENBANK™ Accession No. NC 000007, nucleotides 55054219-55242525), the C-MYC gene (8q24.21; e.g., GENBANK™ Accession No. NC 000008, nucleotides 128817498-128822856), D5S271 (5p15.2), lipoprotein lipase (LPL) gene (8p22; e.g., GENBANK™ Accession No. NC-000008, nucleotides 19841058-19869049), RB1 (13q14; e.g., GENBANK™ Accession No. NC 000013, nucleotides 47775912-47954023), p53 (17p13.1; e.g., GENBANK™ Accession No. NC 000017, complement, nucleotides 7512464-7531642)), N-MYC (2p24; e.g., GENBANK™ Accession No. NC-000002, complement, nucleotides 151835231-151854620), CHOP (12q13; e.g., GENBANK™ Accession No. NC 000012, complement, nucleotides 56196638-56200567), FUS (16p11.2; e.g., GENBANK™ Accession No. NC 000016, nucleotides 31098954-31110601), FKHR (13p14; e.g., GENBANK™ Accession No. NC-000013, complement, nucleotides 40027817-40138734), as well as, for example: ALK (2p23; e.g., GENBANK™ Accession No. NC-000002, complement, nucleotides 29269144-29997936), Ig heavy chain, CCND1 (11q13; e.g., GENBANK™ Accession No. NC-000011, nucleotides 69165054.69178423), BCL2 (18q21.3; e.g., GENBANK™ Accession No. NC-000018, complement, nucleotides 58941559-59137593), BCL6 (3q27; e.g., GENBANK™ Accession No. NC-000003, complement, nucleotides 188921859-188946169), MALF1, AP1 (1p32-p31; e.g., GENBANK™ Accession No. NC 000001, complement, nucleotides 59019051-59022373), TOP2A (17q21-q22; e.g., GENBANK™ Accession No. NC 000017, complement, nucleotides 35798321-35827695), TMPRSS (21q22.3; e.g., GENBANK™ Accession No. NC 000021, complement, nucleotides 41758351-41801948), ERG (21q22.3; e.g., GENBANK™ Accession No. NC-000021, complement, nucleotides 38675671-38955488); ETV1 (7p21.3; e.g., GENBANK™ Accession No. NC-000007, complement, nucleotides 13897379-13995289), EWS (22q12.2; e.g., GENBANK™ Accession No. NC 000022, nucleotides 27994271-28026505); FLI1 (11q24.1-q24.3; e.g., GENBANK™ Accession No. NC 000011, nucleotides 128069199-128187521), PAX3 (2q35-q37; e.g., GENBANK™ Accession No. NC 000002, complement, nucleotides 222772851-222871944), PAX7 (1p36.2-p36.12; e.g., GENBANK™ Accession No. NC-000001, nucleotides 18830087-18935219), PTEN (10q23.3; e.g., GENBANK™ Accession No. NC-000010, nucleotides 89613175-89716382), AKT2 (19q13.1-q13.2; e.g., GENBANK™ Accession No. NC 000019, complement, nucleotides 45431556-45483036), MYCL1 (1p34.2; e.g., GENBANK™ Accession No. NC 000001, complement, nucleotides 40133685-40140274), REL (2p13-p12; e.g., GENBANK™ Accession No. NC-000002, nucleotides 60962256-61003682) and CSF1R (5q33-q35; e.g., GENBANK™ Accession No. NC-000005, complement, nucleotides 149413051-149473128).

Examples

Bioconjugate Synthesis and Purification

BSA-Hapten Conjugates

BSA protein solid (Fraction V, 60 mg) was dissolved in 3 mL PBS (100 mM phosphate, 150 mM NaCl, pH=7.5) and rotated at room temperature for 1 h. The resulting solution was filtered with a 0.2μ Pall GHP syringe filter and analyzed by UV-VIS for concentration resulting in an 18.1 mg/mL solution. The BSA stock (1 mL) was treated with 20 equivalents the NHS ester of the appropriate labeling reagent in anhydrous DMF. The DMF volume was maintained at or below approximately 15% (v/v). The resulting mixture was rotated over night at room temperature. The resulting mixture was filtered with a 0.2μ Pall GHP syringe filter and purified by size exclusion chromatography. The resulting conjugate fractions were combined and analyzed by UV-VIS for concentration and label/protein ratio. Samples were stored at 2-6° C. until use.

GAR-Hapten Conjugates

Goat anti-rabbit pAb (1 mg/mL in PBS) was treated with 30 equivalents the NHS ester of the appropriate labeling reagent in anhydrous DMF. The DMF volume was maintained at or below approximately 15% (v/v). The resulting mixture was rotated over night at room temperature. The resulting mixture was filtered with a 0.2μ Pall GHP syringe filter and purified by size exclusion chromatography. The resulting conjugate fractions were combined and analyzed by UV-VIS for concentration and label/protein ratio. Samples were stored at 2-6° C. until use.

BioLayer Interferometry (BLI) Analysis

Figure 6:
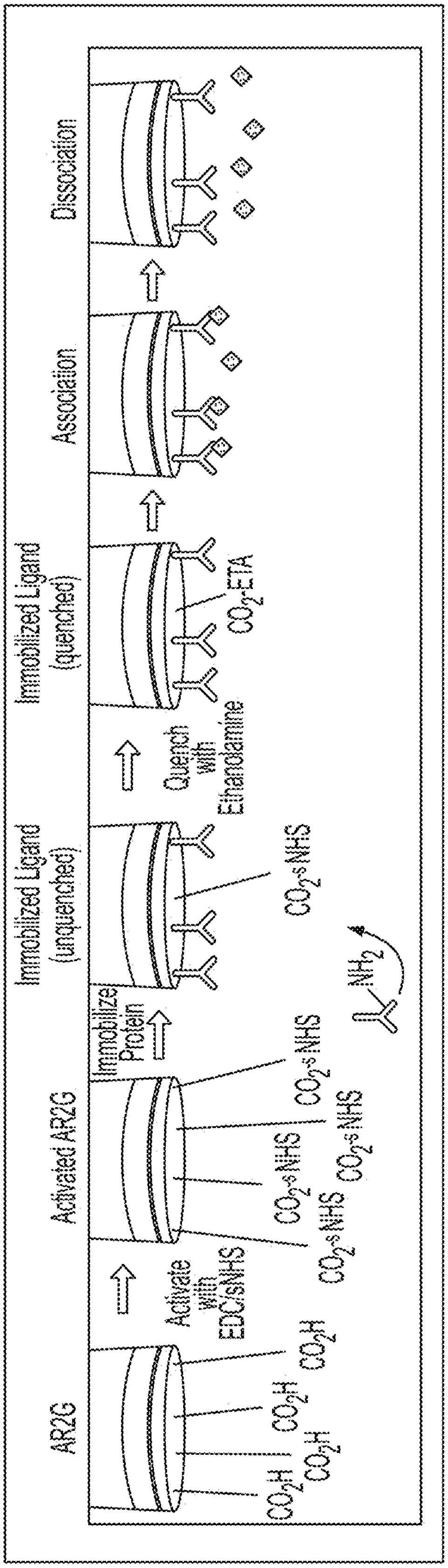
FIG. 6 provides a scheme for covalent immobilization of a protein on AR2G biosensors with subsequent analyte binding. After activation, immobilization and quenching, the kinetics of association and dissociation between the immobilized ligand and analyte are measured.
Figure 20:
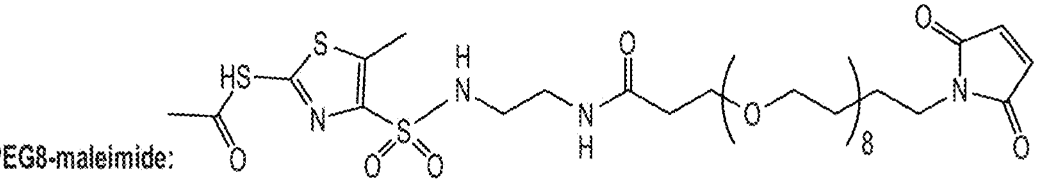
FIG. 20 illustrates examples of labeling reagents for biological proteins, which may include, but not be limited to, maleimides, NHS esters, hydrazides and ethyl carbodiamides.
Figure 20:
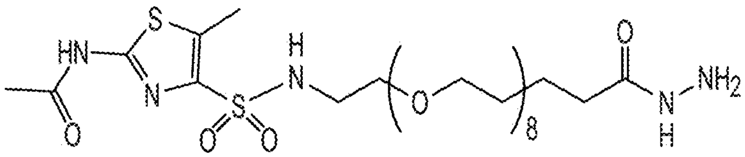
Figure 20:
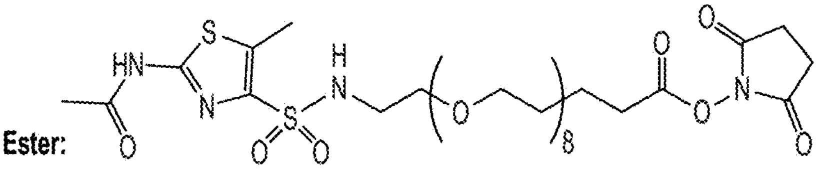
Figure 20:
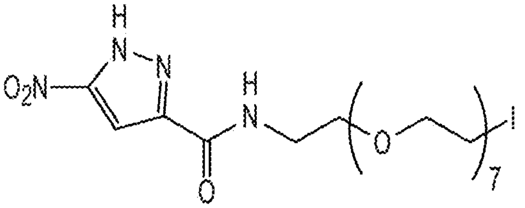
Figure 20:
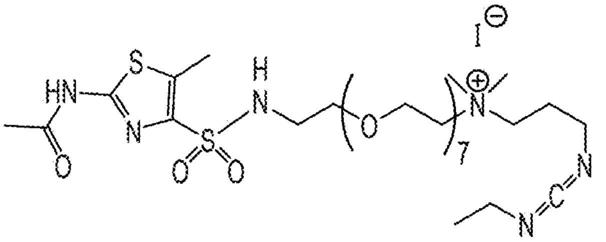
Figure 20:
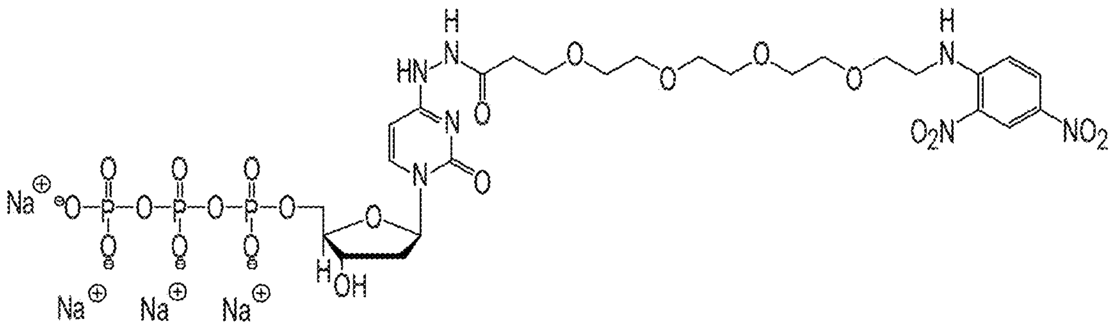
Figure 21:
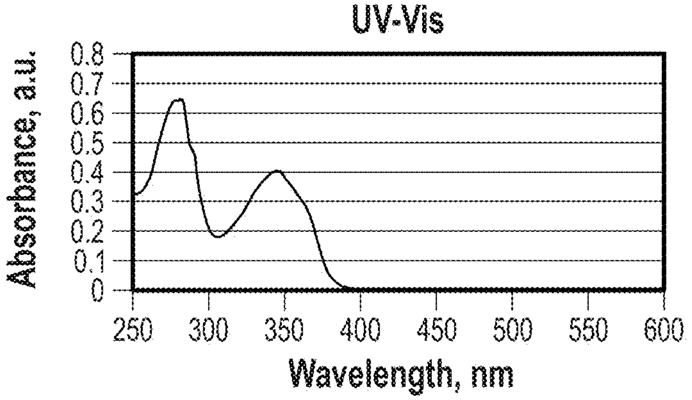
FIG. 21 illustrates absorbance spectra of a coumarin-based conjugate of the present disclosure.
Figure 22:
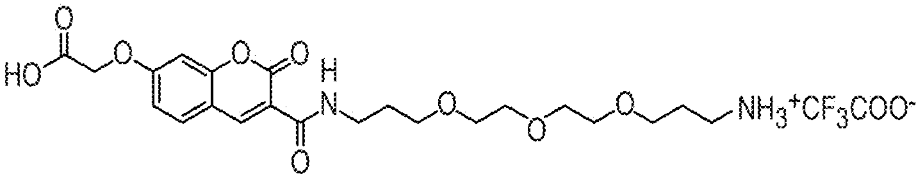
FIG. 22 illustrates absorbance spectra of a coumarin-based conjugate of the present disclosure.
Figure 22:
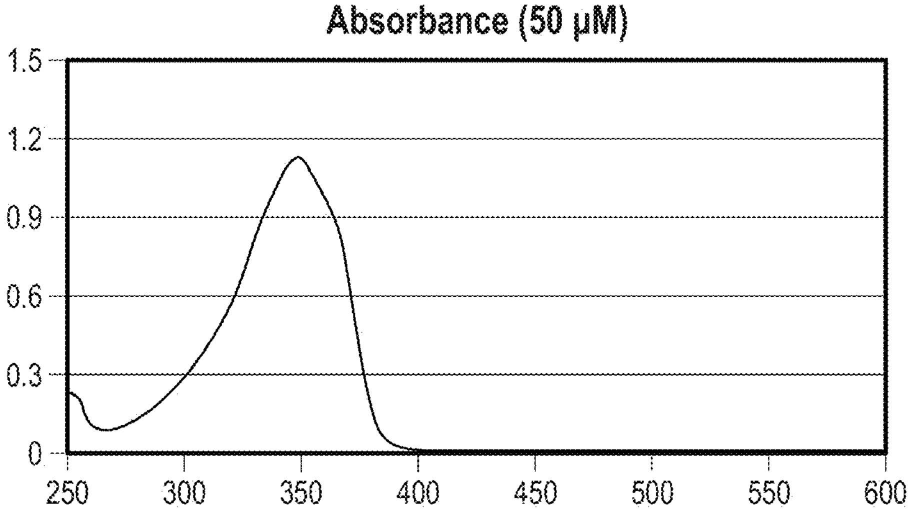
Figure 24:
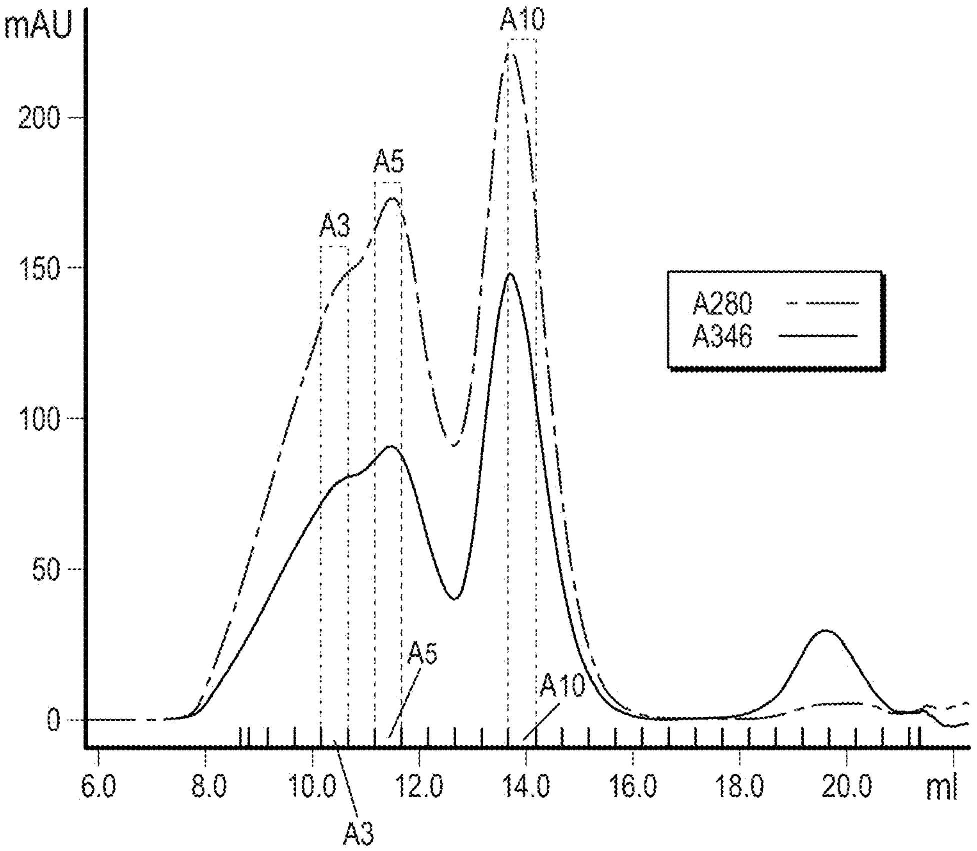
FIG. 24 illustrates size exclusion chorography spectra of the three coumarin-based conjugates of FIG. 23 according to the present disclosure.

Individual protein conjugates (antibody conjugates or BSA immunogens) were labeled with the new coumarin-based reagents disclosed herein and with tyramide-dPEG8-hapten and NHS-dPEG8-hapten labeling reagents (see FIG. 20) (and as disclosed in PCT Application No. PCT/US2011/042849), the disclosure of which is hereby incorporated by reference herein in its entirety. BioLayer Interferometry (BLI) was used to characterize the impact of protein labeling on protein interactions on a Pall-ForteBio Octet Red instrument with amine reactive 2nd Generation (AR2G) biosensors (FIG. 6). The AR2G biosensors provide a surface with a high density of carboxylic acids and a low propensity for non-specific interactions. Protein immobilization was achieved through standard EDC-catalyzed amide bond formation to create a covalent bond between a reactive amine on the protein and the carboxy-terminated biosensor surface. The carboxylic acids were activated by reaction with EDC (1-Ethyl-3-[3-dimethyl-aminopropyl] carbodiimide hydrochloride) and s-NHS (N-hydroxysulfosuccinimide) to generate highly reactive NHS esters. The esters rapidly reacted with the primary amines of proteins to form highly stable amide bonds. The covalent immobilization fastened the protein to the biosensor surface allowing analysis of binding events and kinetic characterization.

Representative BLI Assays

Octet RED BLI analytical assays were performed using Pall-ForteBio AR2G Biosensor tips. Assay conditions were performed as suggested in Pall-ForteBio Dip and Read™ Amine Reactive Second-Generation Technical Note 26 with minor modifications. The AR2G biosensors activation and quenching were performed as suggested in technical note 26. Individual reagent concentrations were modified as necessary in each assay as needed to maximize signal-to-noise while minimizing background binding events. All BLI assay steps were performed at 37° C. Each representative assay is discussed below.

Coumarin-Based Reagent Antibody Cross-Reactivity Study

This assay was performed to access any potential cross reactivity with the coumarin-based reagents described herein. A BSA-CLBF immunogen was immobilized on the AR2G Biosensor at 1.25 μg/mL concentration in 100 mM NaOAc (pH=5). Assessment of anti-hapten cross reactivity was performed at 725 ng/mL anti-hapten mAb in PBS (100 mM phosphate, 150 mM NaCl, pH=7.5) with Pall-ForteBio Kinetics Additive. Time steps are shown in the table below.

| Step | Step Name | Time (s) | Shake Speed |
|---|---|---|---|
| 1 | Sensor Equilibrium | 300 | 1000 |
| 2 | EDC/s-NHS Sensor Activation | 300 | 1000 |
| 3 | BSA Immunogen Immobilization | 1200 | 1000 |
| 4 | Ethanolamine Sensor Quench | 300 | 1000 |
| 5 | Sensor Baseline | 300 | 1000 |
| 6 | Anti-hapten mAb Binding | 2400 | 1000 |
| 7 | Anti-hapten mAb Dissociation | 2400 | 1000 |

Coumarin-Based Reagent Impact on Antigen and Anti-Label Recognition [Rb Immobilization—Labelled GAR Recognition—Anti-Label Recognition]

This assay was performed to better understand how the coumarin-based reagent structure impacted a labelled antibody's ability to detect its antigen. Additionally, a secondary anti-label antibody was used to better understand how a linker structure impacted label detection. A rabbit pAb was immobilized on the AR2G Biosensor at 25 μg/mL concentration in 100 mM NaOAc (pH=5). GAR recognition of the Rb mAb was performed at 3 μg/mL in PBS (100 mM phosphate, 150 mM NaCl, pH=7.5) with Pall-ForteBio Kinetics Additive. Anti-label recognition was performed at 3 μg/mL in PBS (100 mM phosphate, 150 mM NaCl, pH=7.5) with Pall-ForteBio Kinetics Additive. Time steps are shown in the table below.

| Step | Step Name | Time (s) | Shake Speed |
|---|---|---|---|
| 1 | Sensor Equilibrium | 300 | 1000 |
| 2 | EDC/s-NHS Sensor Activation | 300 | 1000 |
| 3 | Rabbit mAb Immobilization | 1200 | 1000 |
| 4 | Ethanolamine Sensor Quench | 300 | 1000 |
| 5 | Sensor Baseline | 300 | 1000 |
| 6 | Hapten Labeled GAR pAb Binding | 1500 | 1000 |
| 7 | Hapten Labeled GAR pAb Dissociation | 1500 | 1000 |
| 8 | Anti-hapten mAb Binding | 1500 | 1000 |
| 9 | Anti-hapten mAb Dissociation | 800 | 1000 |

Results and Discussions

Coumarin-Based Reagent Antibody Cross-Reactivity Study

Figure 7:
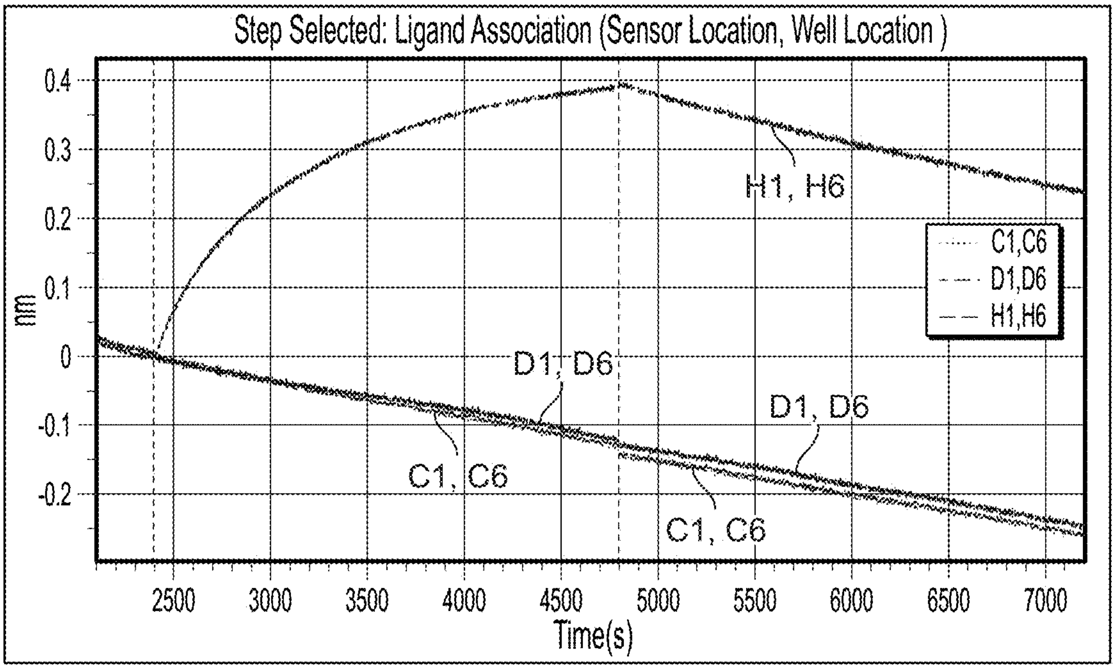
FIG. 7 sets forth a representative cross-reactivity screen for mouse anti-hapten antibody association and dissociation steps with BSA-CL-BF immunogen are shown above. Shown are Ms Anti-BF mAb (H1, H6), Ms Anti-PPT mAb (C1, C6), and Ms Anti-DABSYL mAb (D1, D6) recognition. No significant interactions were observed with anti-PPT or anti-DABSYL mAbs.

The use of the coumarin-based reagents of the present disclosure enable the detection of hard-to-detect hapten labels. Hapten labels are commonly used in multiplex staining assays setting the requirements to understand if any interactions are observed with the anti-hapten antibody library. BioLayer Interferometry studies were performed where the BSA-CLBF immunogen was immobilized on the tip. The anti-hapten antibody library was then screen for any potential cross-reactivity. FIG. 7 sets forth an example of anticipated interaction of MS anti-BF mAb (H1, H6) with the modified tip. The MS anti-BF mAb binding to the sensor tip causes a net increase in layer growth on the tip resulting in a positive association signal through 4800s. Net dissociation is shown in the last frame after 4800s. The Ms Anti-PPT mAb (C1, C6) and Ms Anti-DABSYL mAb (D1, D6) antibodies do not show any significant interaction with the coumarin linker modified biosensor tips.

Figure 8:
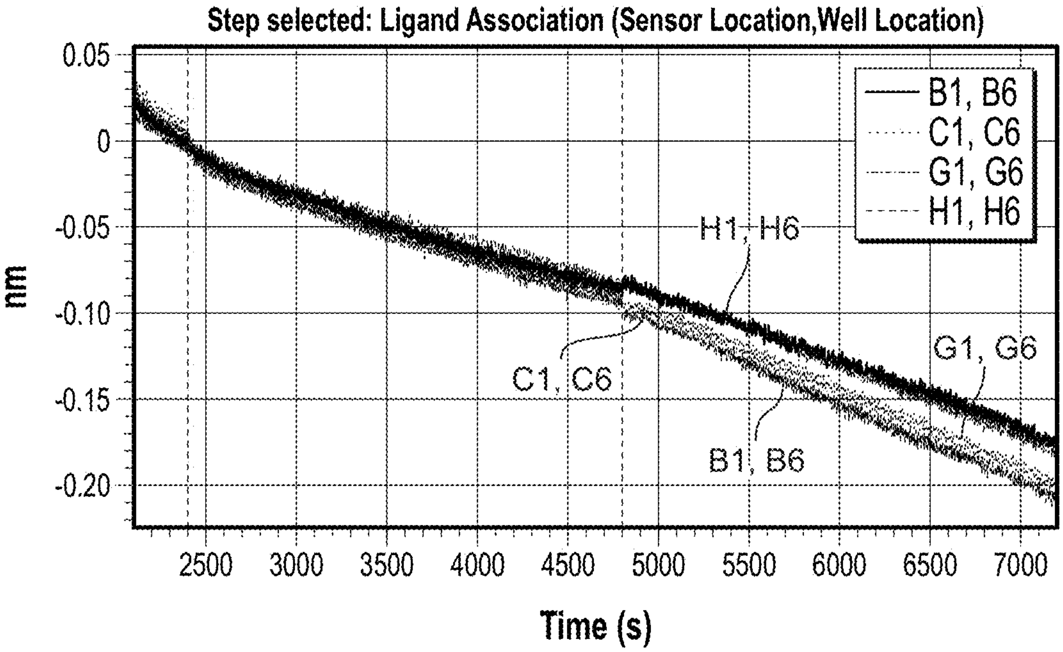
FIG. 8 sets forth a representative cross-reactivity screen for mouse anti-hapten antibody association and dissociation steps with BSA-CL-BF immunogen are shown above. Ms Anti-NP mAb (B1, B6; C1, C6) and Ms Anti-TS mAb (H1, H6; G1, G6) BSA-CLBF recognition are shown above.
Figure 9:
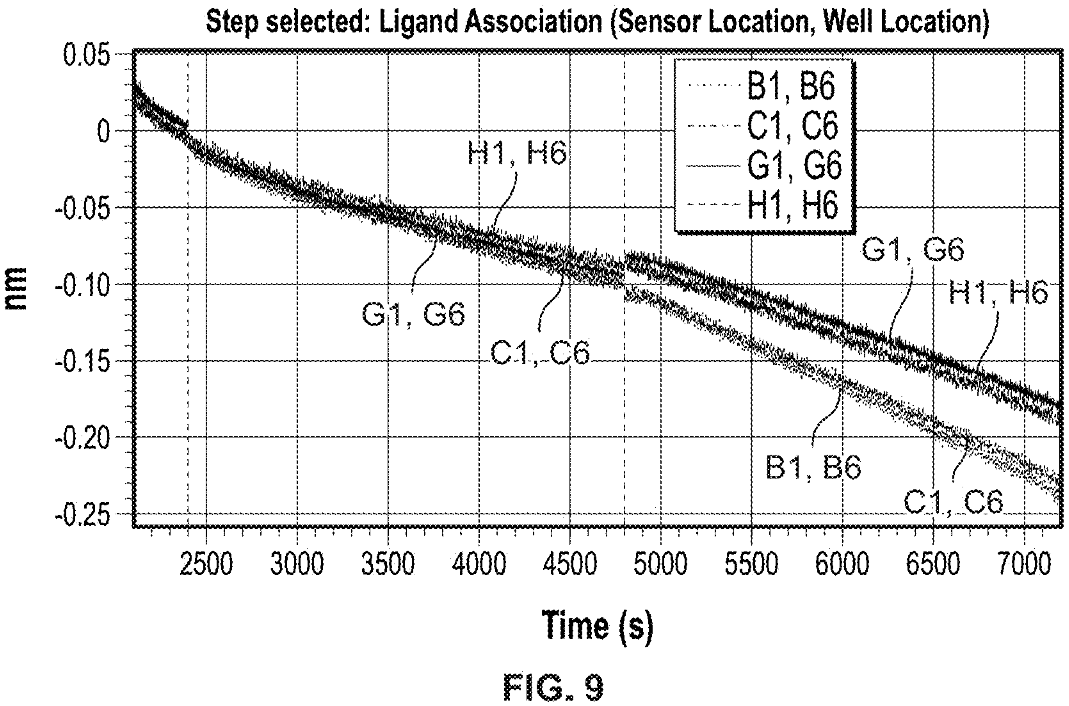
FIG. 9 sets forth a representative cross-reactivity screen for mouse anti-hapten antibody association and dissociation steps with BSA-CL-BF immunogen are shown above. Ms Anti-NCA mAb (B1, B6; C1, C6) and Ms Anti-HQ mAb (H1, H6; G1, G6) BSA-CLBF recognition are shown above.
Figure 10:
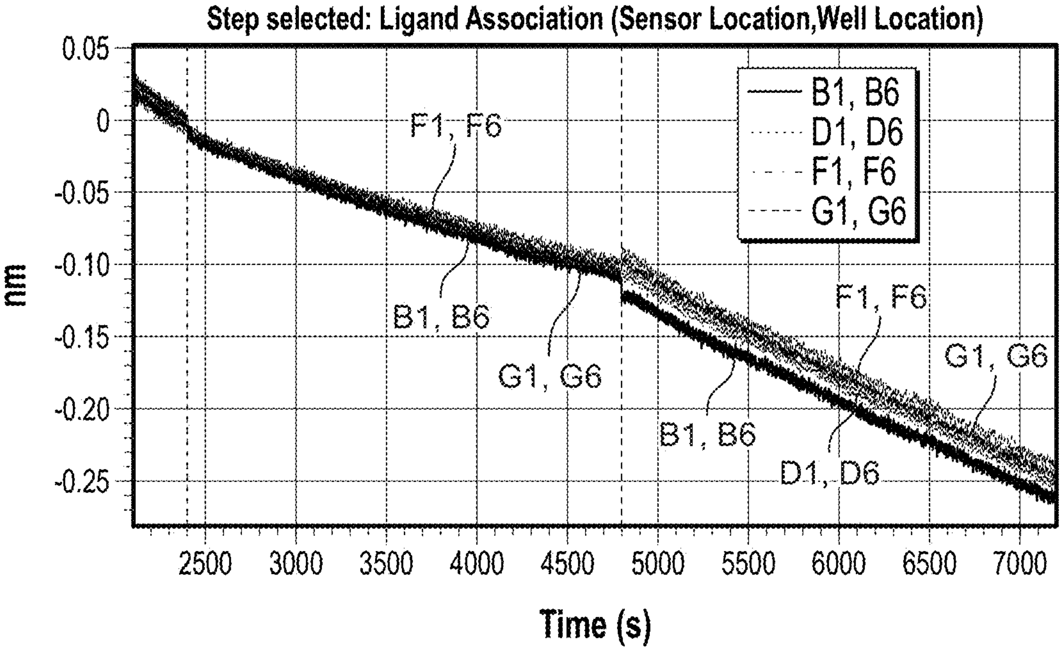
FIG. 10 sets forth a representative cross-reactivity screen for mouse anti-hapten antibody association and dissociation steps with BSA-CL-BF immunogen are shown above. Ms Anti-DCC mAb (B1, B6; D1, D6) and Ms Anti-ROT mAb (F1, F6; G1, G6) BSA-CLBF recognition are shown above.
Figure 11:
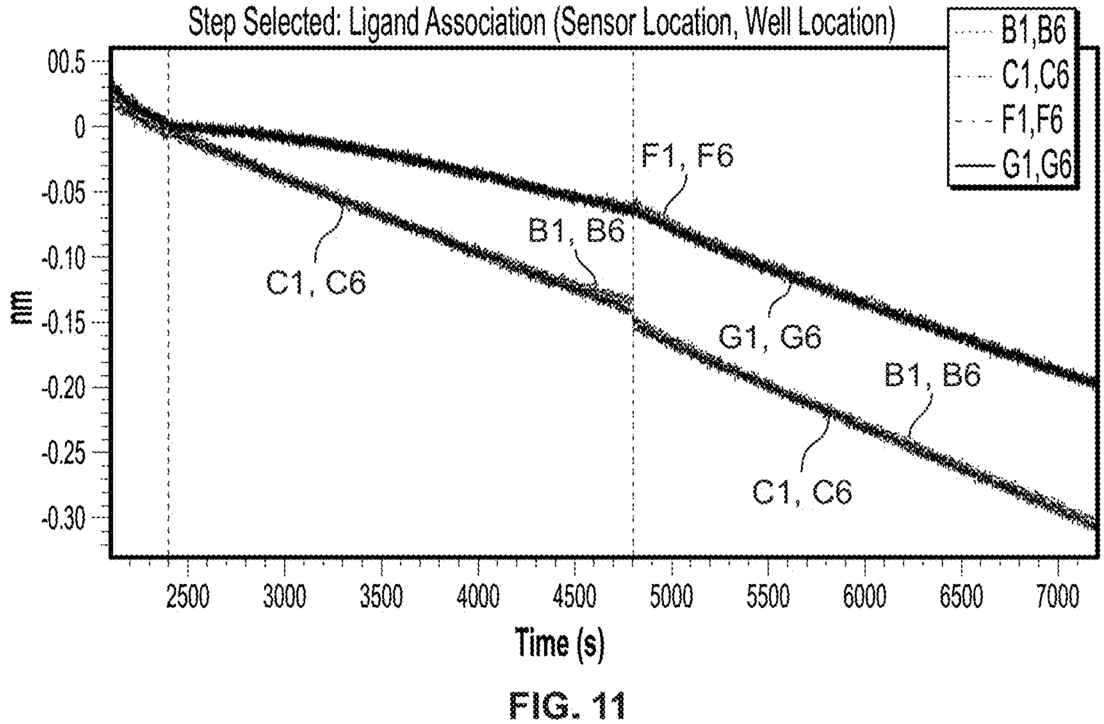
FIG. 11 sets forth a representative cross-reactivity screen for mouse anti-hapten antibody association and dissociation steps with BSA-CL-BF immunogen are shown above. Ms Anti-DIG mAb (B1, B6; C1, C6) and Ms Anti-DNP mAb (F1, F6; G1, G6) BSA-CLBF recognition are shown above.
Figure 12:
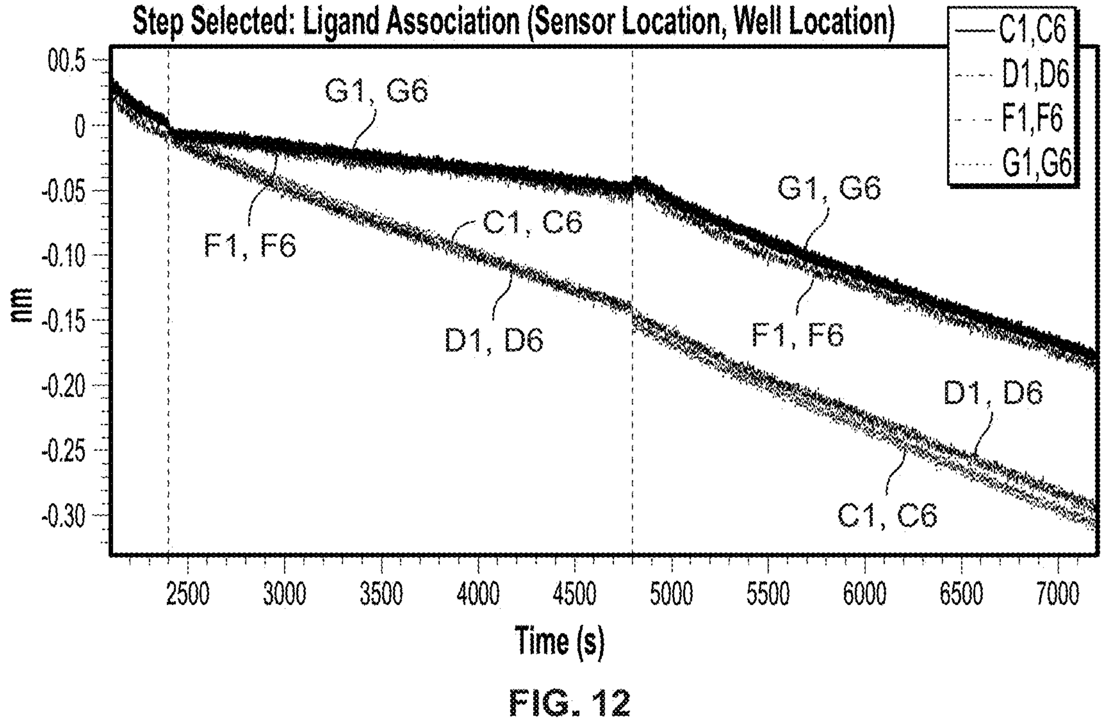
FIG. 12 sets forth a representative cross-reactivity screen for mouse anti-hapten antibody association and dissociation steps with BSA-CL-BF immunogen are shown above. Ms Anti-BD mAb (C1, C6; D1, D6) and Ms Anti-DNP mAb (F1, F6; G1, G6) BSA-CLBF recognition are shown above.

The remaining Ms anti-hapten library was screen against similar BSA-CLBF modified biosensor tips in separate BLI experiments. No significant interaction was observed in FIG. 8 with the coumarin-based reagent modified biosensor tips and Ms Anti-NP mAb (B1, B6; C1, C6) and Ms Anti-TS mAb (H1, H6; G1, G6) antibodies. The Ms Anti-NCA mAb (B1, B6; C1, C6) and Ms Anti-HQ mAb (H1, H6; G1, G6) antibodies also did not show any significant interaction with the coumarin-based reagent modified biosensor tips (see FIG. 8). No significant interaction was observed in FIG. 10 with the coumarin-based reagent modified biosensor tips and Ms Anti-DCC mAb (B1, B6; D1, D6) and Ms Anti-ROT mAb (F1, F6; G1, G6) antibodies. BLI results of FIG. 11 demonstrate that no interaction was observed with Ms Anti-DIG mAb (red, lgt. blue); however, Ms Anti-DNP mAb (B1, B6; C1, C6) antibodies showed positive interactions with the coumarin-based reagent. The Ms Anti-DNP mAb BLI binding response (80 pm) observed was approximately 15% the MS anti-BF mAb BLI binding response (520 pm, FIG. 7). Moreover, the Ms Anti-DNP mAb antibody non-specific binding failed to readily dissociate from the biosensor tip suggesting tissue background staining would be observed. The Ms Anti-DNP mAb (F1, F6; G1, G6) coumarin linker recognition was confirmed in a separate BLI experiment shown in FIG. 11. Again, the Ms Anti-DNP mAb antibody failed to readily dissociate from the biosensor tip. The BLI results in FIG. 12 also demonstrated that no interaction was observed with Ms Anti-BD mAb (C1, C6; D1, D6) and the biosensor tip.

Linker Impact on Antigen and Anti-Label Recognition [Rb Immobilization—Labelled GAR Recognition—Anti-Label Recognition]

Figure 13:
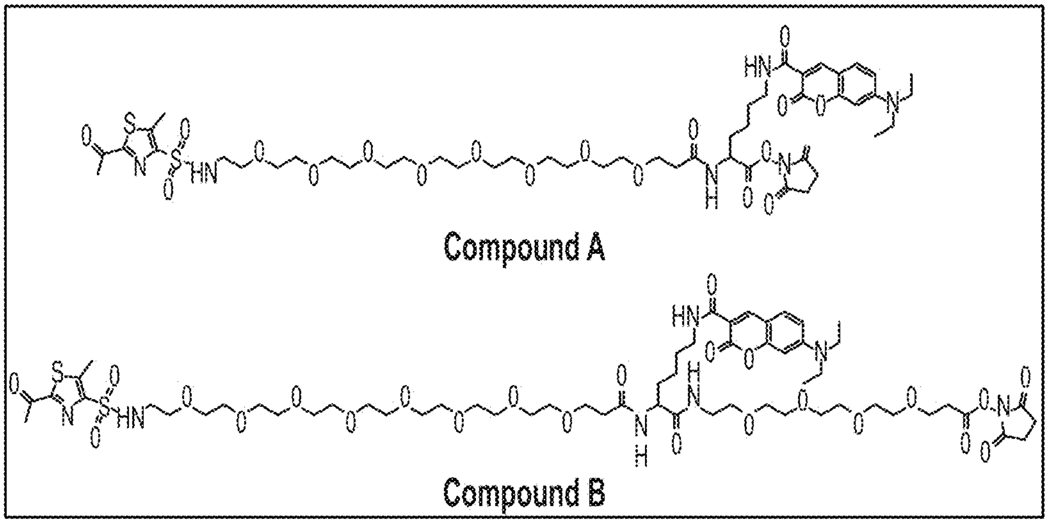
FIG. 13 sets forth branched chromogen linkers GAR-lys(DCC)dPEG8TS (Compound A) and GAR-dPEG4-lys(DCC)dPEG8TS (Compound B).

GAR-Lys(DCC)dPEG8TS Versus GAR-dPEG4-Lys(DCC) dPEG8TS Conjugate:

The GAR-lys(DCC)dPEG8TS and GAR-dPEG4-lys (DCC)dPEG8TS conjugates utilized a lysine amino acid core as a branched ligand. An easy to detect DCC coumarin hapten was used as a potential chromophore and directly bound to the lysine primary amine. A second-dPEGTS hapten group was used as a difficult to quantify label was bound to the lysine core secondary amine (See FIG. 13—Compound A). This group was directly conjugated to the protein with a NHS group directly on the lysine branch. A second bridge lysine linker core was generated where a dPEG4 handle was added to provide separation from the lysine bridge (See FIG. 13—Compound B). The extra dPEG4 spacer group was expected to decrease steric interactions and provide more flexibility to the labeling group making it easier to both increase protein loading capability and assay detection performance (1° antigen and anti-label recognitions).

The GAR pAb (1 mg, 1 mg/mL) was conjugated with 30 equivalents of both linker constructs. The GAR-lys(DCC) dPEG8TS conjugate (GAR+Compound A) was afforded a linker/GAR ratio=3.3 (913 mg, 89% yield). The GAR-dPEG4-lys(DCC)dPEG8TS conjugate (GAR+Compound B) was afforded a linker/GAR ratio=5.4 (913 mg, 84% yield). The extra dPEG4 spacer between the lysine bridge and NHS ester acted as expected to afford higher antibody label loading. Equivalent yields were afforded for both conjugates.

Figure 14:
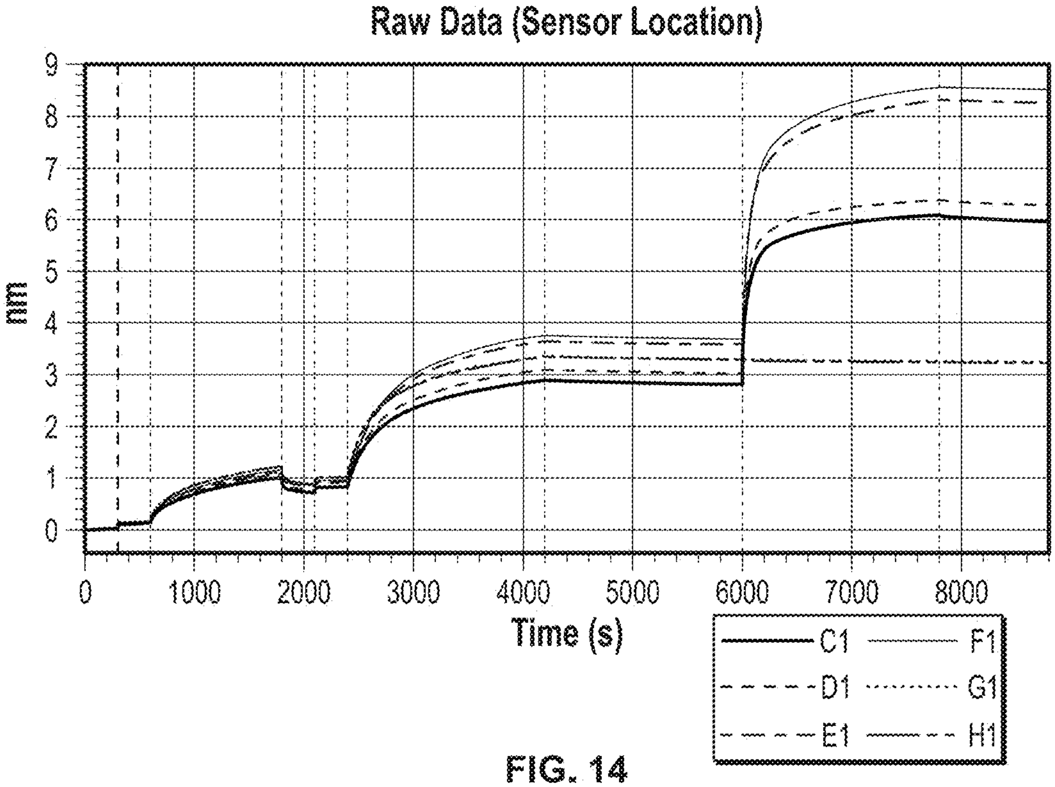
FIG. 14 sets forth the BLI Elisa assay profile shown was performed with Rb mAb immobilization (600-1800s), GAR-Rb recognition (2400-4200s), and anti-TS label recognition (6000-7800s). Shown are GAR-lys(DCC)dPEG8TS conjugate (D1, Cl), GAR-dPEG4-lys(DCC)dPEG8TS conjugate (F1, E1), and unmodified GAR pAb (G1, H1) recognition.
Figure 15:
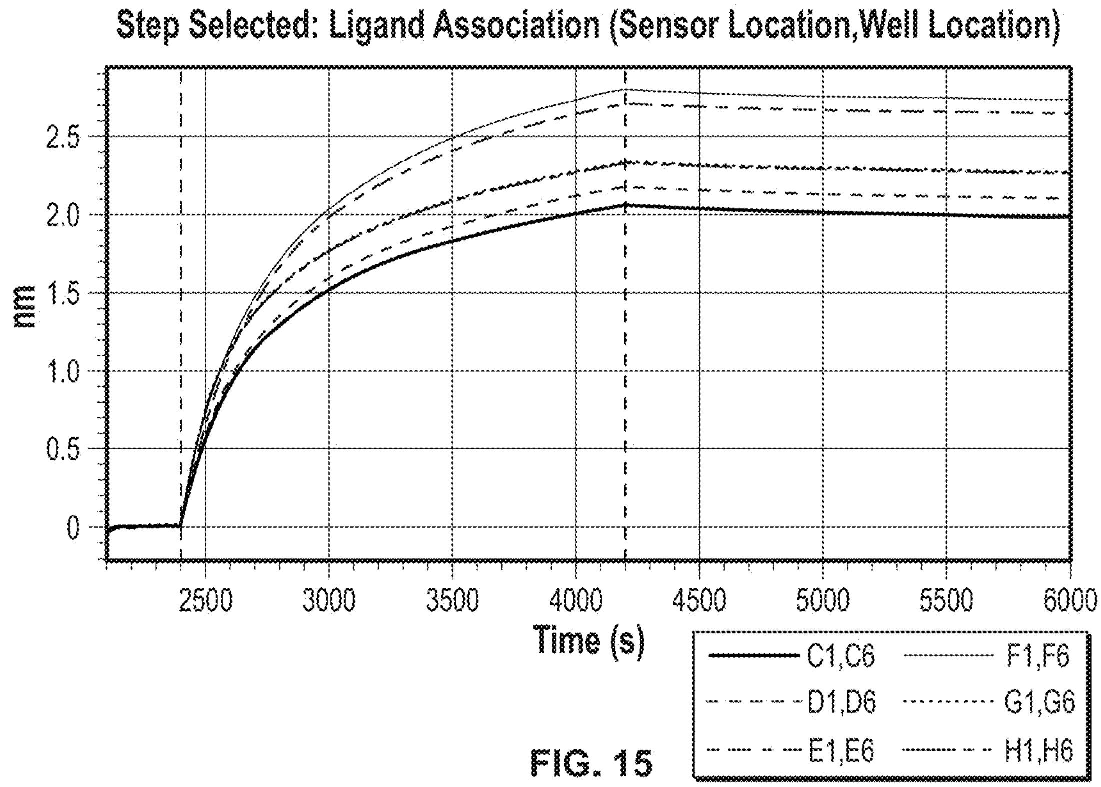
FIG. 15 sets forth the BLI Elisa assay profile shown GAR-Rb recognition (2400-4200s) and subsequent dissociation (4200-6000s). Shown are GAR-lys(DCC)dPEG8TS conjugate (C1, C6; D1, D6), GAR-dPEG4-lys(DCC)dPEG8TS conjugate (F1, F6; E1, E6), and unmodified GAR pAb (H1, H6; G1, G6) Rb mAb recognition.
Figure 16:
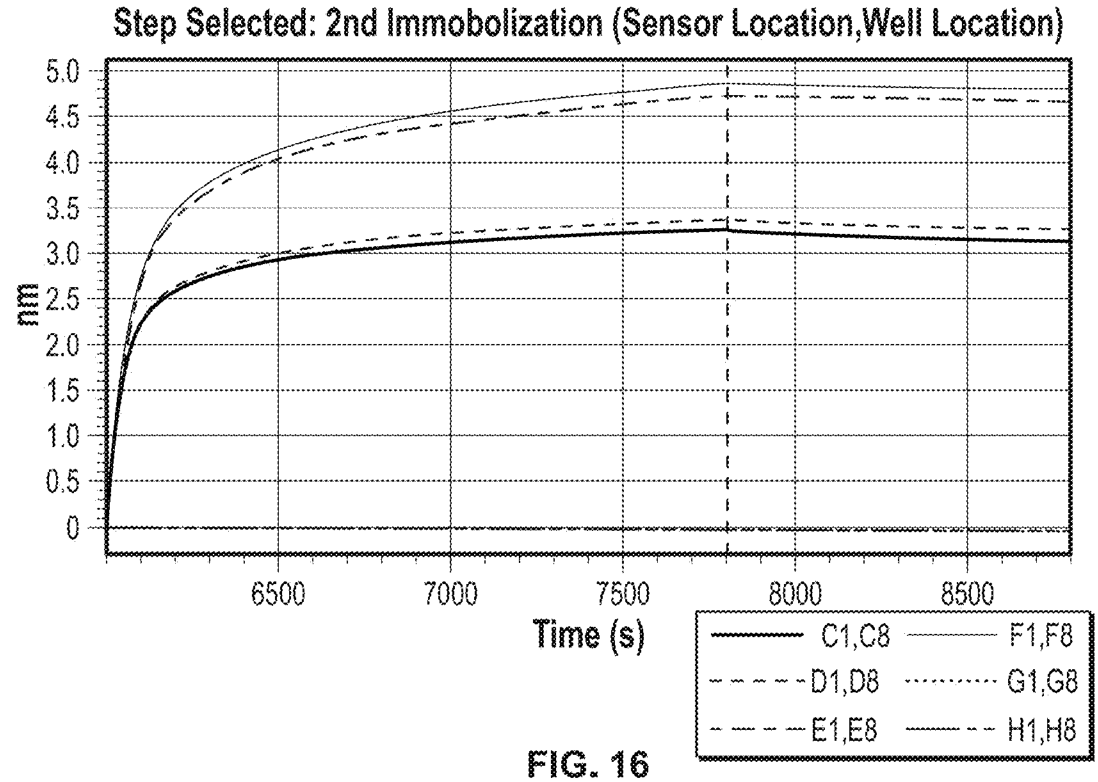
FIG. 16 sets forth the BLI Elisa assay profile shown for the Ms anti-TS mAb recognition of the TS-hapten label (6000-7800s) and subsequent Ab dissociation (7800-8800s). Shown are GAR-lys(DCC)dPEG8TS conjugate (C1, C8; D1, D8), GAR-dPEG4-lys(DCC)dPEG8TS conjugate (E1, E8; F1, F8), and unmodified GAR pAb (G1, G8; H1, H8).

The BLI assay was designed mimic a tissue staining assay. A rabbit mAb was bound to the biosensor tip then recognized with the above conjugates. Additionally, an unmodified GAR standard was used for comparison of labels impact on rabbit recognition. Tertiary recognition of the TS hapten labels was performed with Ms Anti-TS mAb (see FIG. 14). The GAR antibody conjugates recognized the rabbit antibody loaded biosensor tips similarly to the unmodified GAR antibody. Slightly thicker Elisa layer was observed with the GAR-dPEG4-lys(DCC)dPEG8TS conjugate than the GAR-lys(DCC)dPEG8TS conjugate (see FIG. 15). No differences were observed in the modified GAR conjugates dissociation rates. The additional dPEG4 spacer between the lysine bridge and NHS ester in the GAR-dPEG4-lys(DCC)dPEG8TS also afforded more Ms Anti-TS mAb (see FIG. 16).

GAR-CLBF Conjugate

The GAR pA (2 mg, 1 mg/mL) was labelled with 30 equivalents of BFdPEG8NHS and BFCLNHS reagents. The GAR-CLBF conjugate UV/VIS analysis showed a BF/GAR ratio=5.85 (1.6 mg, 80% yield). The CL coumarin detectable moiety provided a conjugate with label/Ab ratio and yields in the anticipated ranges. The GAR-dPEG8BF conjugate UV/VIS analysis overestimated the BF/GAR ratio=38.1 (860 mg, 43% yield) as expected. The GAR-dPEG8BF conjugate data is inaccurate and must be used as a relative approximation.

Figure 17:
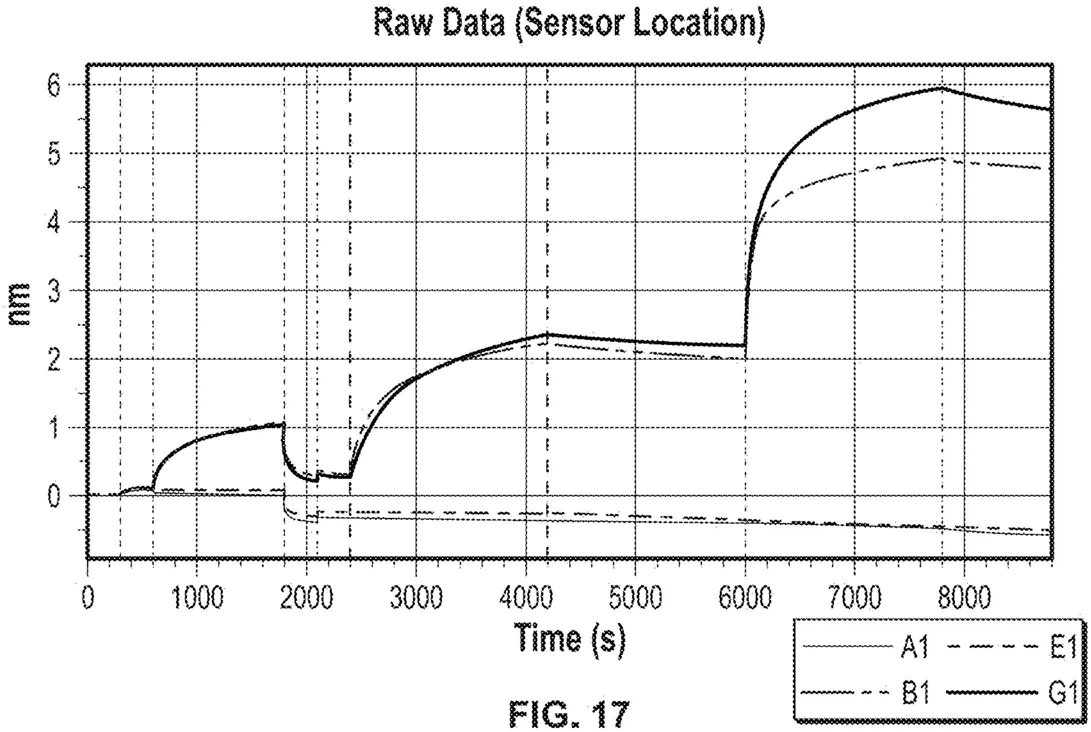
FIG. 17 sets forth the BLI Elisa assay profile shown was performed with Rb mAb immobilization (600-1800s), GAR-Rb recognition (2400-4200s), and anti-BF label recognition (6000-7800s). Shown are GAR-dPEG8BF conjugate (G1, B1) and GAR-CLBF conjugate (yellow, teal). Negative control sensors with no Rb mAb immobilization are shown (E1, A1)
Figure 18:
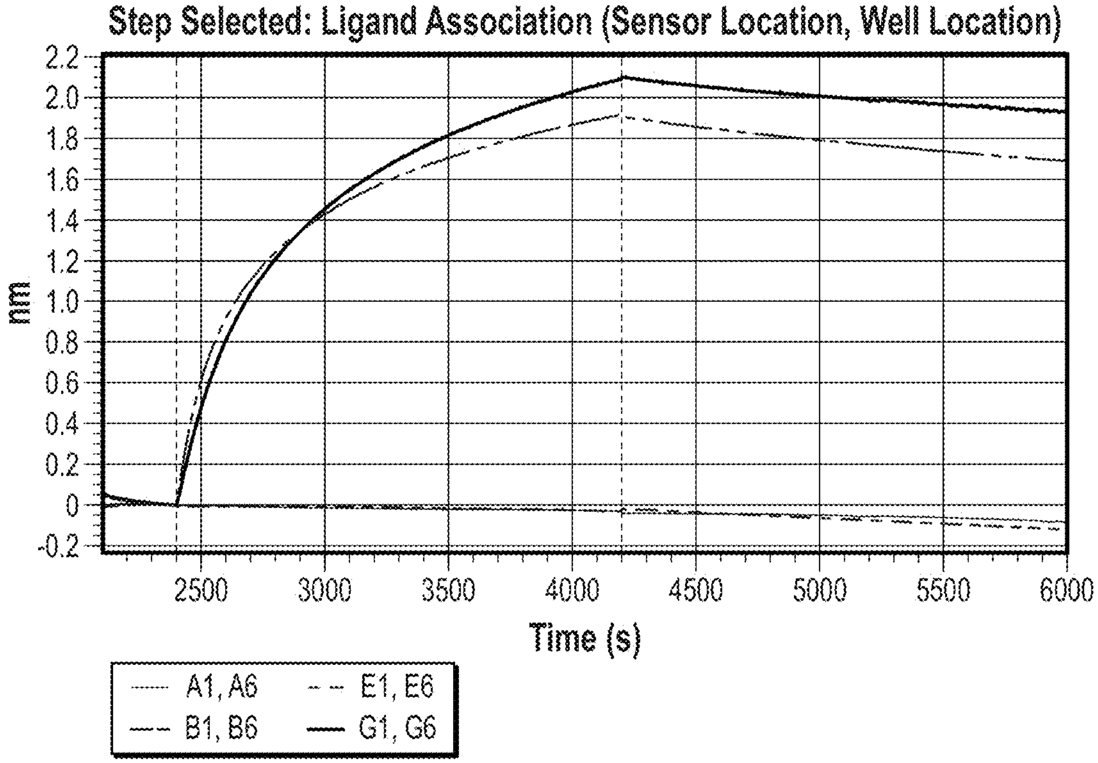
FIG. 18 sets forth the BLI Elisa assay profile shown GAR-Rb recognition (2400-4200s) and subsequent dissociation (4200-6000s). Shown are GAR-dPEG8BF conjugate (B1, B6; G1, G6) and GAR-CLBF conjugate (A1, A8; E1, E8).
Figure 19:
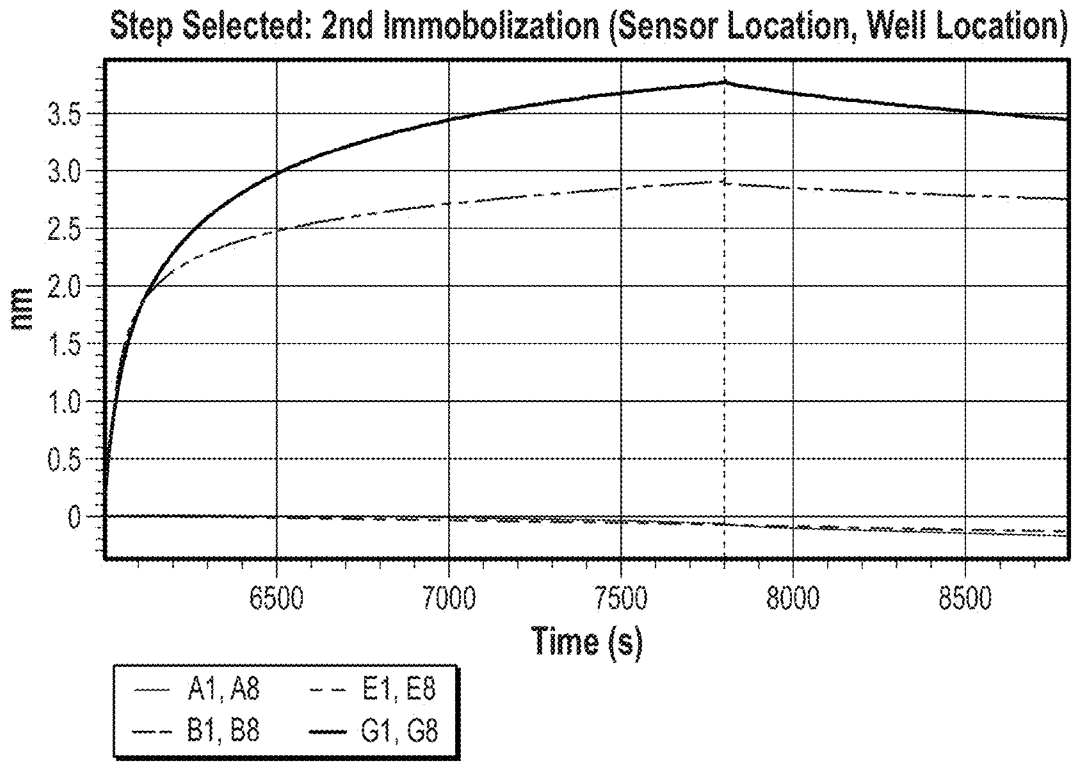
FIG. 19 sets forth the BLI Elisa assay profile shown for the Ms anti-BF mAb recognition of the BF-hapten label (6000-7800s) and subsequent Ab dissociation (7800-8800s). Shown are GAR-dPEG8BF conjugate (B1, B8; G1, G8) and GAR-CLBF conjugate (A1, A8; E1, E8).

The BLI assay was again designed mimic a tissue staining assay. A rabbit mAb was bound to the biosensor tip then recognized with the above conjugates. Tertiary recognition of the BF hapten labels was performed with Ms Anti-BF mAb (see FIG. 17). The GAR antibody conjugates recognized the rabbit antibody loaded biosensor tips with similarly (see FIG. 18). Slightly thicker Elisa layer was observed with the GAR-CLBF conjugate than the GAR-dPEG8BF conjugate. No significant differences were observed in the modified GAR conjugates dissociation rates. The -dPEG4-coumarin-dPEG4-BF linker is believed to be more rigid than the -dPEG-BF label. The GAR-CLBF conjugate provided a thicker Elisa layer on the biosensor tip when recognized by the Ms Anti-BF mAb (see FIG. 19). The Ms Anti-BF mAb did dissociate slightly faster from the GAR-CLBF conjugate than the GAR-dPEG8BF conjugate.

This increased Ms Anti-BF mAb dissociation from the GAR-CLBF conjugate maybe the result of looser binding (faster koff) caused by more Ms Anti-BF mAb affinity interactions versus avidity interaction. As previously stated, the CL coumarin linker is anticipated to be more rigid. The added flexibility of the -dPEG-BF label most likely allows unbound BF labels to bend and bind to the other complimentary domain of Ms Anti-BF mAbs with affinity interactions resulting in stronger avidity binding. Avidity binding (2-1) always results in less dissociation than affinity interactions (1-1) which may be competing with the coumarin linker. A similar dissociation phenomenon was observed in the cross-reactivity study (See FIG. 7, above).

Additional Embodiments

Additional Embodiment 1. A compound defined by the structure of any of Formulas (IA) or (IB):

$$A-\!\left[L^1\right]_m\!-W-\!\left[L^2\right]_n\!-B, \qquad \text{(IA)}$$

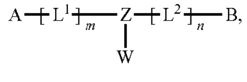

(IB)

wherein

A and B are independently a reactive functional group, a detectable label, or an enzyme reactive moiety;

$L^1$ and $L^2$ are linkers;

W includes a substituted or unsubstituted coumarin moiety or a moiety which is a substituted or an unsubstituted derivative or analog of coumarin;

Z is a bond, a —CH— group, a —CH—$CH_2$— group or a —$CH_2$—CH— group; and m and n are independently an integer ranging from 1 to 4.

Additional Embodiment 2. The compound of additional embodiment 1, wherein both A and B are reactive functional groups.

Additional Embodiment 3. The compound of additional embodiment 1, wherein A is a reactive functional group and B is a detectable label.

Additional Embodiment 4. The compound of additional embodiment 3, wherein the detectable label is a hapten, a chromogen, or a fluorophore.

Additional Embodiment 5. The compound of additional embodiment 4, wherein the hapten is selected from the group consisting of an oxazole, a pyrazole, a thiazole, a benzofurazan, a triterpene, a urea, a thiourea other than a rhodamine thiourea, a nitroaryl other than dinitrophenyl or trinitrophenyl, a rotenoid, a cyclolignan, a heterobiaryl, an azoaryl, and a benzodiazepine Additional Embodiment 6. The compound of additional embodiment 1, wherein A is an enzyme reactive moiety selected from the group consisting of tyramide moieties, moieties which are derivatives of tyramide moieties, and quinone methide precursor moieties.

Additional Embodiment 7. The compound of additional embodiment 6, wherein the enzyme reactive moiety has the structure of Formula (VIIA):

(VIIA)

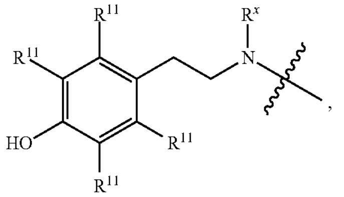

wherein each $R^{11}$ group is independently selected from hydrogen or a lower alkyl group having between 1 and 4 carbon atoms, and wherein $R^x$ is H or a $C_1$-$C_4$ alkyl group.

Additional Embodiment 8. The compound of additional embodiment 6, wherein the enzyme reactive moiety has the structure provided by Formula (VIIIA):

(VIIIA)

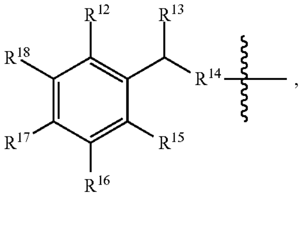

wherein $R^2$ is a group selected from phosphate, amide, nitro, urea, sulfate, methyl, ester, beta-lactam, or a sugar;

$R^{13}$ is a halide;

$R^{15}$, $R^{16}$, $R^{17}$, and $R^{18}$ are independently selected from hydrogen or an aliphatic group having between 1 and 4 carbon atoms; and $R^{14}$ is —$(CH_2)_w$NH—, —$O(CH_2)_w$NH—, —N(H)C(O)$(CH_2)_w$NH—, —C(O)N(H)$(CH_2)_w$NH—, —$(CH_2)_w$O—, —$O(CH_2)_w$O—, —$O(CH_2CH_2O)_w$—, —N(H)C(O)$(CH_2)_w$O—, —C(O)N(H)$(CH_2)_w$O—, —C(o)N(H)$(CH_2CH_2O)_w$—, —$(CH_2)_w$S—, —$O(CH_2)_w$S—, —N(H)C(O)$(CH_2)_w$S—, —C(O)N(H)$(CH_2)_w$S—, —$(CH_2)_w$NH—, —C(O)N(H)$(CH_2CH_2O)_w$$CH_2CH_2$NH, —C(O)$(CH_2CH_2O)_w$$CH_2CH_2$NH—, —C(O)N(H)$(CH_2)$NHC(O)CH$(CH_3)(CH_2)_w$NH—, or —N(H)$(CH_2)_w$NH—, where w is an integer ranging from 1 to 12.

Additional Embodiment 9. The compound of any of additional embodiments 6 to 8, wherein B is a hapten.

Additional Embodiment 10. The compound of any of additional embodiments 6 to 8, wherein B is a reactive group capable of participating in a click-chemistry reaction.

Additional Embodiment 11. The compound of additional embodiment 10, wherein the group capable of participating in the click-chemistry reaction is a DBCO group, an azide, a TCO group, a alkene group, or a tetrazine group.

Additional Embodiment 12. The compound of any of additional embodiments 1 to 11, wherein W has the structure of either Formula (IVA) or (IVB):

(IVA)

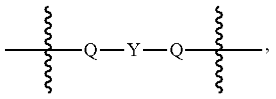

(IVB)

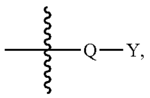

wherein Q is a bond or a substituted or unsubstituted, straight chain or branched $C_1$-$C_{16}$ alkyl group, —$[(CH_2CH_2)_j$—$O]_k$—$CH_2$—, —$[(CH_2)_j$—$O]_k$—$CH_2$—, where j is an integer ranging from 1 to 4 and k is an integer ranging from 1 to 16; —N—$R^x$—; —C(O)—N—$R^x$—; or —N—$R^x$—C(O)—, $R^x$ is H or a $C_1$-$C_4$ alkyl group; and Y is a substituted or unsubstituted coumarin moiety or a moiety which is a substituted or an unsubstituted derivative or analog of coumarin.

Additional Embodiment 13. The compound of any of additional embodiments 1 to 11, wherein the substituted or unsubstituted coumarin moiety, or the moiety which is a substituted or an unsubstituted derivative or analog of coumarin, includes one or more moieties selected from the group consisting of a substituted or unsubstituted, straight chain or branched $C_1$-$C_6$ alkyl group; a substituted or unsubstituted, straight chain or branched $C_1$-$C_6$ alkoxy group; a substituted or unsubstituted, straight chain or branched $C_1$-$C_6$ heteroalkyl group; a trifluoromethyl group; a hydroxyl group; a sulfate group; a cyano group; a halogen; a phosphate group; a saccharide; a carboxylic acid group; a nitro group; —C(O)NR$^x$R$^y$; —S—R$^x$; —$SO_2$; —$SO_2$Cl; —$SO_3$H; —$SO_4$H; —$SO_2$NR$^x$R$^y$; —N(H)—NR$^x$R$^y$; and —NR$^x$R$^y$; and wherein R$^x$ and R$^y$ are independently H or a $C_1$-$C_4$ alkyl group.

Additional Embodiment 14. The compound of any of additional embodiments 1 to 11, wherein W has the structure of either of Formula (VA) or (VB):

(VA)

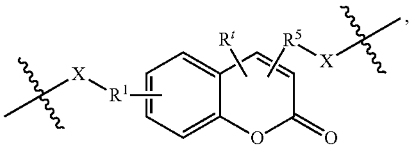

(VB)

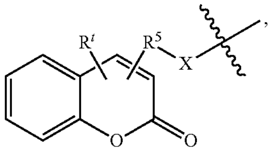

wherein the moiety of Formula (VA) may be substituted with 0, 1, 2, 3, or 4 R$^t$ groups; and wherein the compound of Formula (VB) may be substituted with 0, 1, 2, 3, 4, or 5 R$^t$ groups; and wherein each R$^t$ is independently selected from a substituted or unsubstituted, straight chain or branched $C_1$-$C_{12}$ alkyl group; a substituted or unsubstituted, straight chain or branched $C_1$-$C_{12}$ alkoxy group; a substituted or unsubstituted, straight chain or branched $C_1$-$C_{12}$ heteroalkyl group; a trifluoromethyl group; a hydroxyl group; a sulfate group; a cyano group; a halogen; a phosphate group; a saccharide; a carboxylic acid group; a nitro group; —C(O)NR$^x$R$^y$; —S—R$^x$; —$SO_2$; —$SO_2$Cl; —$SO_3$H; —$SO_4$H; —$SO_2$NR$^x$R$^y$; —N(H)—NR$^x$R$^y$; —NR$^x$R$^y$; and wherein R$^x$ and R$^y$ are independently H or a $C_1$-$C_4$ alkyl group;

R$^1$ is a $C_1$-$C_{10}$ substituted or unsubstituted, branched or unbranched alkyl group, —O—, —O—$CH_2$—, —N(R$^x$)—; or —S—.

R$^5$ is a $C_1$-$C_{10}$ substituted or unsubstituted, branched or unbranched alkyl group, —C(O)—O—; —C(O)—N(H)—; and each X is independently a bond or a substituted or unsubstituted, straight chain or branched $C_1$-$C_{16}$ alkyl group; —[$(CH_2)_j$—O]—$CH_2$—, where j is an integer ranging from 1 to 4 and k is an integer ranging from 1 to 16; —N—R$^x$—; —C(O)—N—R$^x$—; or —N—R$^x$—C(O)—, where R$^x$ is H or a $C_1$-$C_4$ alkyl group.

Additional Embodiment 15. The compound of any of additional embodiments 1 to 11, wherein W has the structure of either Formula (VC) or (VD):

(VC)

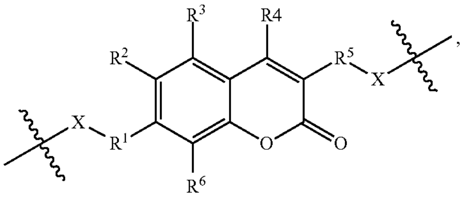

-continued (VD)

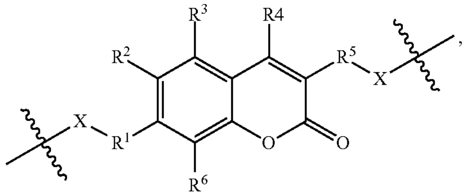

wherein

R$^2$, R$^3$, R$^4$, R$^6$, and R$^7$ are independently selected from a substituted or unsubstituted, straight chain or branched $C_1$-$C_6$ alkyl group; a substituted or unsubstituted, straight chain or branched $C_1$-$C_6$ alkoxy group; a substituted or unsubstituted, straight chain or branched $C_1$-$C_6$ heteroalkyl group; a trifluoromethyl group; a hydroxyl group; a sulfate group; a cyano group; a halogen; a phosphate group; a saccharide; a carboxylic acid group; a nitro group; —C(O)NR$^x$R$^y$; —S—R$^x$; —$SO_2$; —$SO_2$Cl; —$SO_3$H; —$SO_4$H; —$SO_2$NR$^x$R$^y$; —N(H)—NR$^x$R$^y$; —NR$^x$R$^y$;

R$^5$ is a $C_1$-$C_{10}$ substituted or unsubstituted, branched or unbranched alkyl group, —C(O)—O—; —C(O)—N(H)—;

R$^1$ is a $C_1$-$C_{10}$ substituted or unsubstituted, branched or unbranched alkyl group, —O—, —O—$CH_2$—, —N(R$^x$)—; or —S—; and each X is independently a bond or a substituted or unsubstituted, straight chain or branched $C_1$-$C_{16}$ alkyl group; —[$(CH_2)_j$—O]$_k$—$CH_2$—, where j is an integer ranging from 1 to 4 and k is an integer ranging from 1 to 16; —N—R$^x$—; —C(O)—N—R$^x$—; or —N—R$^x$—C(O)—; and wherein each R$^x$ and R$^y$ are independently H or a $C_1$-$C_4$ alkyl group.

Additional Embodiment 16. The compound of any of additional embodiments 1 to 15, wherein each L$^1$ and/or L$^2$ group independently has the Formula (VIA):

(VIA)

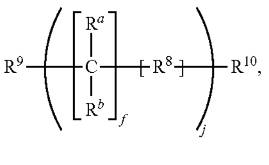

wherein f is 0 or an integer ranging from 1 to 24;

j is an integer ranging from 1 to 24;

R$^8$ is a bond or O, S, —N(R$^c$)(R$^d$), or —N$^+$(R$^c$)(R$^d$)(R$^e$);

R$^a$ and R$^b$ are independently H, a $C_1$-$C_4$ alkyl group, F, Cl, or —N(R$^c$)(R$^d$);

R$^c$, R$^d$, and R$^e$ are independently selected from H or a $C_1$-$C_4$ alkyl group; and R$^9$ and R$^{10}$ are independently a bond or a group having up to 6 carbon atoms and including a carbonyl, an amide, an imide, an ester, an ether, an amine, an thione, or a thiol.

Additional Embodiment 17. A compound defined by the structure of any of Formulas (IXA or IXB):

(IXA)

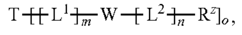

(IXB)

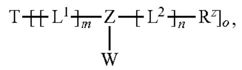

wherein

T is a substituent selected from a specific binding entity, an amino acid, a peptide, a protein, a saccharide, a nucleoside, a nucleotide, an oligonucleotide, a drug, a lipid, or a nanoparticle;

$R^z$ is a detectable label;

o is an integer ranging from 1 to 10;

$L^1$ and $L^2$ are linkers;

W includes a substituted or unsubstituted coumarin moiety or a moiety which is a substituted or an unsubstituted derivative or analog of coumarin;

Z is a bond, a —CH— group, a —CH—$CH_2$— group or a —$CH_2$—CH— group; and m and n are independently an integer ranging from 1 to 4.

Additional Embodiment 18. The compound of additional embodiment 17, wherein T is an antibody.

Additional Embodiment 19. The compound of additional embodiment 18, wherein the antibody is a primary antibody.

Additional Embodiment 20. The compound of additional embodiment 18, wherein the antibody is a secondary antibody.

Additional Embodiment 21. The compound of additional embodiment 17, wherein T is a nucleic acid.

Additional Embodiment 22. The compound of any of additional embodiments 17 to 21, wherein $R^z$ is a hapten.

Additional Embodiment 23. The compound of any of additional embodiments 17 to 21, wherein $R^z$ is an enzyme.

Additional Embodiment 24. The compound of additional embodiment 23, wherein the enzyme is selected from the group consisting of a peroxidase and a phosphatase.

Additional Embodiment 25. The compound of any of additional embodiments 17 to 23, wherein W has the structure of either Formula (VC) or (VD):

(VC)

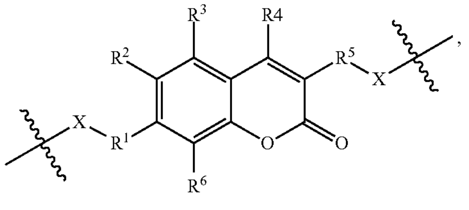

(VD)

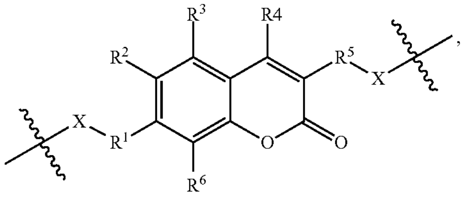

wherein $R^2$, $R^3$, $R^4$, $R^6$, and $R^7$ are independently selected from a substituted or unsubstituted, straight chain or branched $C_1$-$C_6$ alkyl group; a substituted or unsubstituted, straight chain or branched $C_1$-$C_6$ alkoxy group; a substituted or unsubstituted, straight chain or branched $C_1$-$C_6$ heteroalkyl group; a trifluoromethyl group; a hydroxyl group; a sulfate group; a cyano group; a halogen; a phosphate group; a saccharide; a carboxylic acid group; a nitro group; —C(O)$NR^xR^y$; —S—$R^x$; —$SO_2$; —$SO_2Cl$; —$SO_3H$; —$SO_4H$; —$SO_2NR^xR^y$; —N(H)—$NR^xR^y$; —$NR^xR^y$;

$R^5$ is a $C_1$-$C_{10}$ substituted or unsubstituted, branched or unbranched alkyl group, —C(O)—O—; —C(O)—N(H)—;

$R^1$ is a $C_1$-$C_{10}$ substituted or unsubstituted, branched or unbranched alkyl group, —O—, —O—$CH_2$—, —N($R^x$)—; or —S—; and each X is independently a bond or a substituted or unsubstituted, straight chain or branched $C_1$-$C_{16}$ alkyl group; —$[(CH_2)_j—O]_k$—$CH_2$—, where j is an integer ranging from 1 to 4 and k is an integer ranging from 1 to 16; —N—$R^x$—; —C(O)—N—$R^x$—; or —N—$R^x$—C(O)—; and wherein each $R^x$ and $R^y$ are independently H or a $C_1$-$C_4$ alkyl group.

Additional Embodiment 26. The compound of any of additional embodiments 17 to 25, wherein each $L^1$ and/or $L^2$ group independently has the Formula (VIA):

(VIA)

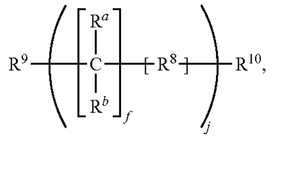

wherein f is 0 or an integer ranging from 1 to 24;

j is an integer ranging from 1 to 24;

$R^8$ is a bond or O, S, —N($R^c$)($R^d$), or —$N^+$($R^c$)($R^d$)($R^e$);

$R^a$ and $R^b$ are independently H, a $C_1$-$C_4$ alkyl group, F, Cl, or —N($R^c$)($R^d$);

$R^c$, $R^d$, and $R^e$ are independently selected from H or a $C_1$-$C_4$ alkyl group; and $R^9$ and $R^{10}$ are independently a bond or a group having up to 6 carbon atoms and including a carbonyl, an amide, an imide, an ester, an ether, an amine, an thione, or a thiol.

Additional Embodiment 27. A method of detecting one or more targets within a biological sample comprising:

(a) labeling a first target of the one of the targets within the biological sample with a primary antibody specific for the first target;

(b) contacting the sample with a compound of any of Formulas (IXC) or (IXD):

(IXC)

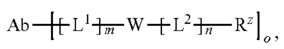

(IXD)

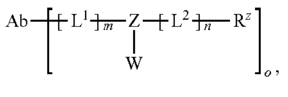

wherein

Ab is a secondary antibody;

$R^z$ is a detectable label;

o is an integer ranging from 1 to 10;

$L^1$ and $L^2$ are linkers;

W includes a substituted or unsubstituted coumarin moiety or a moiety which is a substituted or an unsubstituted derivative or analog of coumarin;

Z is a bond, a —CH— group, a —CH—$CH_2$— group or a —$CH_2$—CH— group; and m and n are independently an integer ranging from 1 to 4; and (c) contacting the sample with one or more reagents to detect the detectable label $R^z$.

Additional Embodiment 28. The method of additional embodiment 27, wherein Ab is an anti-primary antibody antibody.

Additional Embodiment 29. The method of additional embodiment 28, wherein the primary antibody is conjugated to a hapten; and wherein Ab is an anti-hapten antibody.

Additional Embodiment 30. The method of additional embodiment 27, wherein the compound is the compound of any of additional embodiments 20, and 22 to 26.

Additional Embodiment 31. A method of detecting one or more targets within a biological sample comprising:

(a) labeling a first target of the one of the targets within the biological sample with an enzyme by contacting the sample with a conjugate comprising an enzyme and a primary antibody specific for the first target;

(b) contacting the sample with a compound of any of Formulas (IA) or (IB):

(IA)

$$A-\!\!\left[L^1\right]_m\!-W-\!\left[L^2\right]_n\!-B,$$

(IB)

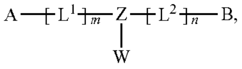

wherein

A is an enzyme reactive moiety;

B is a detectable label;

$L^1$ and $L^2$ are linkers;

W includes a substituted or unsubstituted coumarin moiety or a moiety which is a substituted or an unsubstituted derivative or analog of coumarin;

Z is a bond, a —CH— group, a —CH—$CH_2$— group or a —$CH_2$—CH— group; and m and n are independently an integer ranging from 1 to 4; and (c) contacting the sample with one or more reagents to detect the detectable label B.

Additional Embodiment 32. The method of additional embodiment 31, wherein W has the structure of either Formula (VC) or (VD):

(VC)

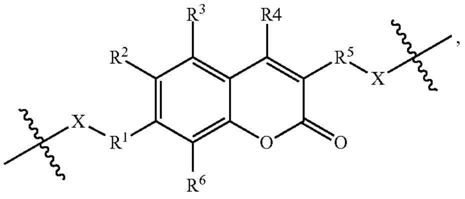

-continued (VD)

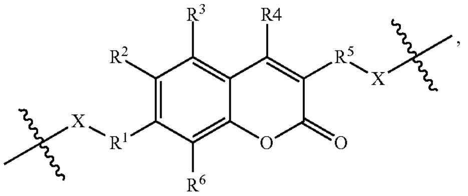

wherein $R^2$, $R^3$, $R^4$, $R^6$, and $R^7$ are independently selected from a substituted or unsubstituted, straight chain or branched $C_1$-$C_6$ alkyl group; a substituted or unsubstituted, straight chain or branched $C_1$-$C_6$ alkoxy group; a substituted or unsubstituted, straight chain or branched $C_1$-$C_6$ heteroalkyl group; a trifluoromethyl group; a hydroxyl group; a sulfate group; a cyano group; a halogen; a phosphate group; a saccharide; a carboxylic acid group; a nitro group; —C(O)$NR^xR^y$; —S—$R^x$; —$SO_2$; —$SO_2$Cl; —$SO_3$H; —$SO_4$H; —$SO_2NR^xR^y$; —N(H)—$NR^xR^y$; —$NR^xR^y$;

$R^5$ is a $C_1$-$C_{10}$ substituted or unsubstituted, branched or unbranched alkyl group, —C(O)—O—; —C(O)—N(H)—;

$R^1$ is a $C_1$-$C_{10}$ substituted or unsubstituted, branched or unbranched alkyl group, —O—, —O—$CH_2$—, —N($R^x$)—; or —S—; and each X is independently a bond or a substituted or unsubstituted, straight chain or branched $C_1$-$C_{16}$ alkyl group; —$[(CH_2)_j—O]_k$—$CH_2$—, where j is an integer ranging from 1 to 4 and k is an integer ranging from 1 to 16; —N—$R^x$—; —C(O)—N—$R^x$—; or —N—$R^x$—C(O)—; and wherein each $R^x$ and $R^y$ are independently H or a $C_1$-$C_4$ alkyl group.

Additional Embodiment 33. The method of additional embodiments 31 or 32, wherein the compounds of any of Formulas (IA) or (IB) have an extinction coefficient of at least 15,000 M−1 cm−1.

Additional Embodiment 34. The method of additional embodiment 31, wherein the compound is the compound of any of additional embodiments 6 to 11.

Additional Embodiment 35. The method of additional embodiment 34, wherein W has the structure of either Formula (IVA) or (IVB):

(IVA)

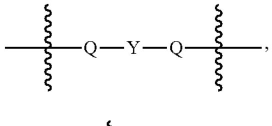

(IVB)

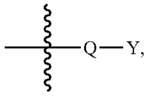

wherein Q is a bond or a substituted or unsubstituted, straight chain or branched $C_1$-$C_{16}$ alkyl group, —$[(CH_2CH_2)_j—O]$—$CH_2$—, —$[(CH_2)_j—O]$—$CH_2$—, where j is an integer ranging from 1 to 4 and k is an integer ranging from 1 to 16; —N—$R^x$—; —C(O)—N—$R^x$—; or —N—$R^x$—C(O)—, $R^x$ is H or a $C_1$-$C_4$ alkyl group; and Y is a substituted or unsubstituted coumarin moiety or a moiety which is a substituted or an unsubstituted derivative or analog of coumarin.

Additional Embodiment 36. The method of additional embodiment 34, wherein the substituted or unsubstituted coumarin moiety, or the moiety which is a substituted or an unsubstituted derivative or analog of coumarin, includes one or more moieties selected from the group consisting of a substituted or unsubstituted, straight chain or branched $C_1$-$C_6$ alkyl group; a substituted or unsubstituted, straight chain or branched $C_1$-$C_6$ alkoxy group; a substituted or unsubstituted, straight chain or branched $C_1$-$C_6$ heteroalkyl group; a trifluoromethyl group; a hydroxyl group; a sulfate group; a cyano group; a halogen; a phosphate group; a saccharide; a carboxylic acid group; a nitro group; —C(O)NR$^x$R$^y$; —S—R$^x$; —$SO_2$; —$SO_2$Cl; —$SO_3$H; —$SO_4$H; —$SO_2$NR$^x$R$^y$; —N(H)—NR$^x$R$^y$; and —NR$^x$R$^y$; and wherein R$^x$ and R$^y$ are independently H or a $C_1$-$C_4$ alkyl group.

Additional Embodiment 37. The method of additional embodiment 34, wherein W has the structure of either of Formula (VA) or (VB):

(VA)

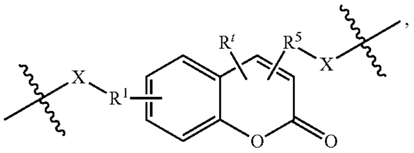

(VB)

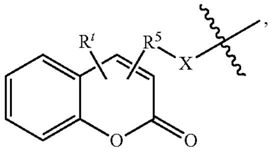

wherein the moiety of Formula (VA) may be substituted with 0, 1, 2, 3, or 4 R$^t$ groups; and wherein the compound of Formula (VB) may be substituted with 0, 1, 2, 3, 4, or 5 R$^t$ groups; and wherein each R$^t$ is independently selected from a substituted or unsubstituted, straight chain or branched $C_1$-$C_{12}$ alkyl group; a substituted or unsubstituted, straight chain or branched $C_1$-$C_{12}$ alkoxy group; a substituted or unsubstituted, straight chain or branched $C_1$-$C_{12}$ heteroalkyl group; a trifluoromethyl group; a hydroxyl group; a sulfate group; a cyano group; a halogen; a phosphate group; a saccharide; a carboxylic acid group; a nitro group; —C(O)NR$^x$R$^y$; —S—R$^x$; —$SO_2$; —$SO_2$Cl; —$SO_3$H; —$SO_4$H; —$SO_2$NR$^x$R$^y$; —N(H)—NR$^x$R$^y$; —NR$^x$R$^y$; and wherein R$^x$ and R$^y$ are independently H or a $C_1$-$C_4$ alkyl group;

R$^1$ is a $C_1$-$C_{10}$ substituted or unsubstituted, branched or unbranched alkyl group, —O—, —O—$CH_2$—, —N(R$^x$)—; or —S—.

R$^5$ is a $C_1$-$C_{10}$ substituted or unsubstituted, branched or unbranched alkyl group, —C(O)—O—; —C(O)—N(H)—; and each X is independently a bond or a substituted or unsubstituted, straight chain or branched $C_1$-$C_{16}$ alkyl group; —[$(CH_2)_j$—O]—$CH_2$—, where j is an integer ranging from 1 to 4 and k is an integer ranging from 1 to 16; —N—R$^x$—; —C(O)—N—R$^x$—; or —N—R$^x$—C(O)—, where R$^x$ is H or a $C_1$-$C_4$ alkyl group.

Additional Embodiment 38. The method of additional embodiment 34, wherein W has the structure of either Formula (VC) or (VD):

(VC)

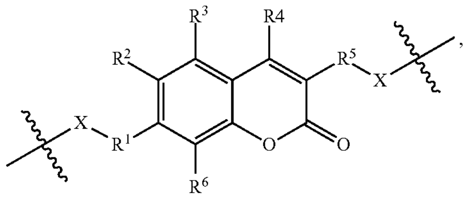

(VD)

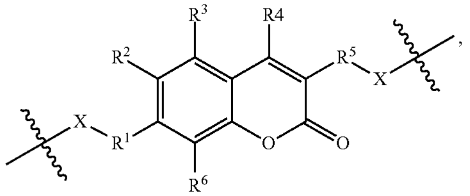

wherein

R$^2$, R$^3$, R$^4$, R$^6$, and R$^7$ are independently selected from a substituted or unsubstituted, straight chain or branched $C_1$-$C_6$ alkyl group; a substituted or unsubstituted, straight chain or branched $C_1$-$C_6$ alkoxy group; a substituted or unsubstituted, straight chain or branched $C_1$-$C_6$ heteroalkyl group; a trifluoromethyl group; a hydroxyl group; a sulfate group; a cyano group; a halogen; a phosphate group; a saccharide; a carboxylic acid group; a nitro group; —C(O)NR$^x$R$^y$; —S—R$^x$; —$SO_2$; —$SO_2$Cl; —$SO_3$H; —$SO_4$H; —$SO_2$NR$^x$R$^y$; —N(H)—NR$^x$R$^y$; —NR$^x$R$^y$;

R$^5$ is a $C_1$-$C_{10}$ substituted or unsubstituted, branched or unbranched alkyl group, —C(O)—O—; —C(O)—N(H)—;

R$^1$ is a $C_1$-$C_{10}$ substituted or unsubstituted, branched or unbranched alkyl group, —O—, —O—$CH_2$—, —N(R$^x$)—; or —S—; and each X is independently a bond or a substituted or unsubstituted, straight chain or branched $C_1$-$C_{16}$ alkyl group; —[$(CH_2)_j$—O]$_k$—$CH_2$—, where j is an integer ranging from 1 to 4 and k is an integer ranging from 1 to 16; —N—R$^x$—; —C(O)—N—R$^x$—; or —N—R$^x$—C(O)—; and wherein each R$^x$ and R$^y$ are independently H or a $C_1$-$C_4$ alkyl group.

Additional Embodiment 39. The method of any of additional embodiments 34 to 38, wherein each L$^1$ and/or L$^2$ group independently has the Formula (VIA):

(VIA)

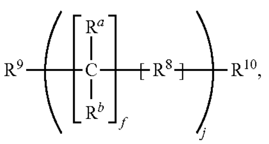

wherein f is 0 or an integer ranging from 1 to 24;

j is an integer ranging from 1 to 24;

$R^8$ is a bond or O, S, —$N(R^c)(R^d)$, or —$N^+(R^c)(R^d)(R^e)$;

$R^a$ and $R^b$ are independently H, a $C_1$-$C_4$ alkyl group, F, Cl, or —$N(R^c)(R^d)$;

$R^c$, $R^d$, and $R^e$ are independently selected from H or a $C_1$-$C_4$ alkyl group; and $R^9$ and $R^{10}$ are independently a bond or a group having up to 6 carbon atoms and including a carbonyl, an amide, an imide, an ester, an ether, an amine, an thione, or a thiol.

All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

Although the present disclosure has been described with reference to a number of illustrative embodiments, it should be understood that numerous other modifications and embodiments can be devised by those skilled in the art that will fall within the spirit and scope of the principles of this disclosure. More particularly, reasonable variations and modifications are possible in the component parts and/or arrangements of the subject combination arrangement within the scope of the foregoing disclosure, the drawings, and the appended claims without departing from the spirit of the disclosure. In addition to variations and modifications in the component parts and/or arrangements, alternative uses will also be apparent to those skilled in the art.

The invention claimed is:

1. A compound selected from the group consisting of

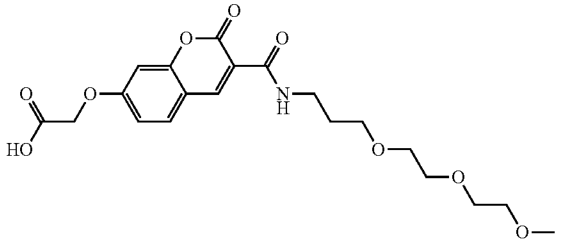

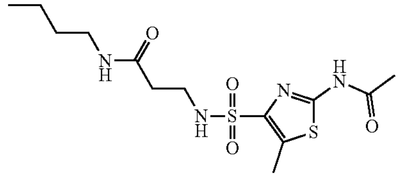
,

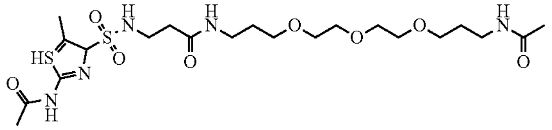

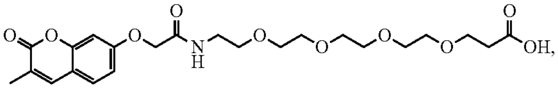
,

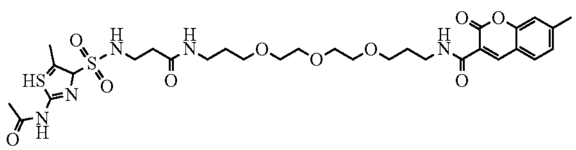

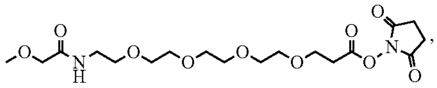
,

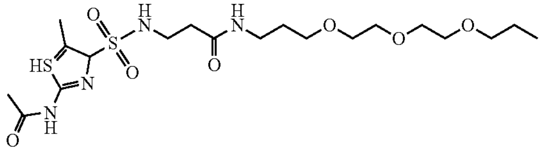

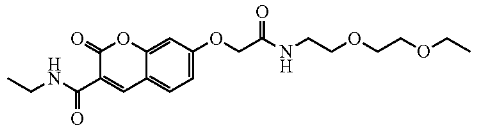

-continued
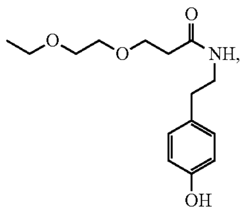
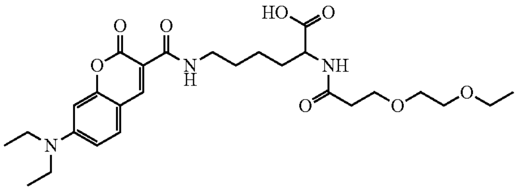
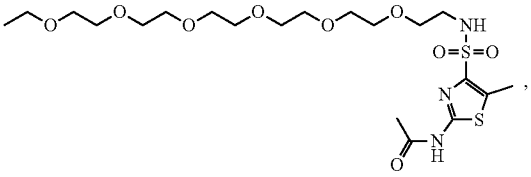
,
,
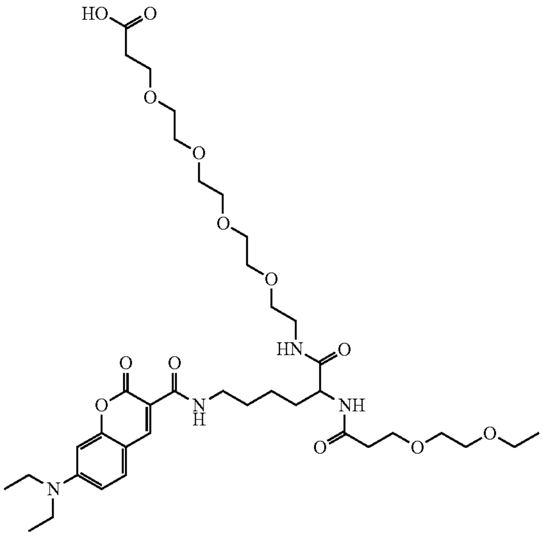
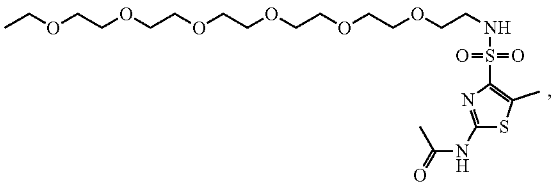
,
and -continued
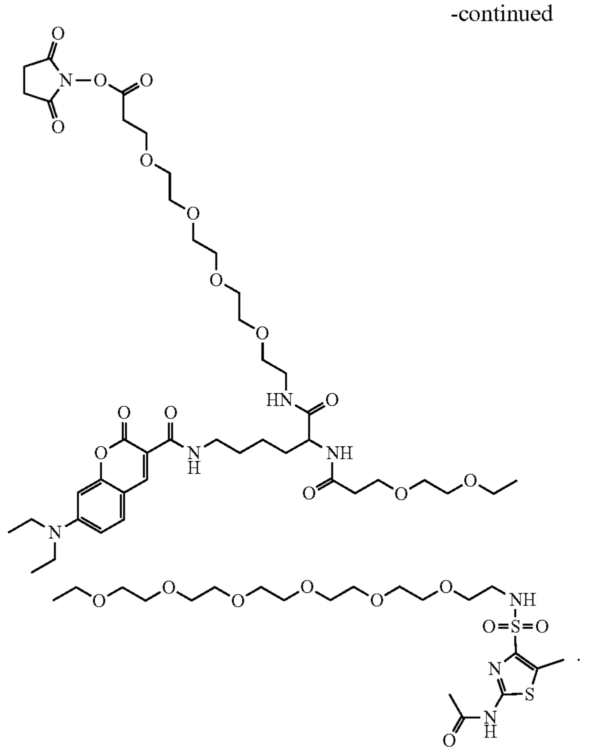
2. A compound selected from the group consisting of
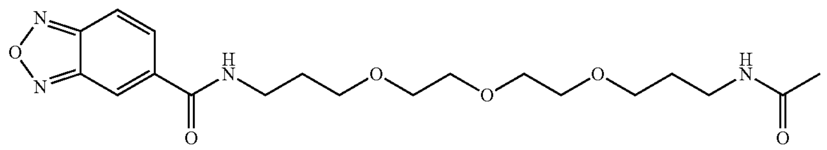
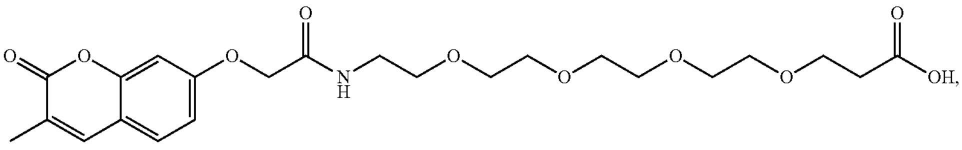
,
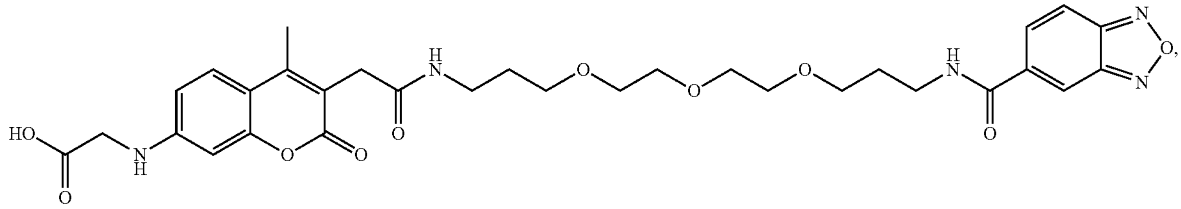
,
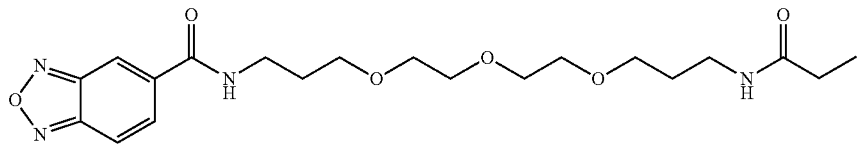
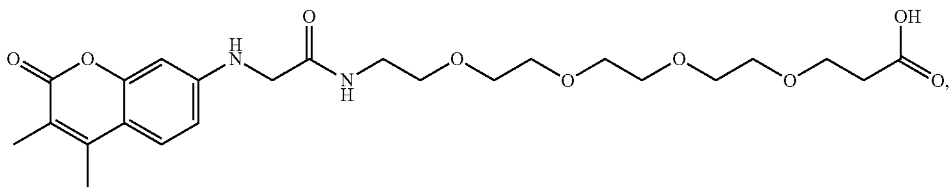
, -continued
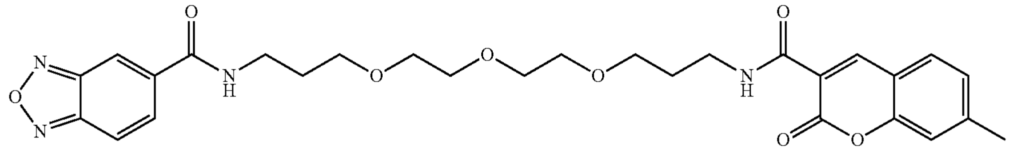
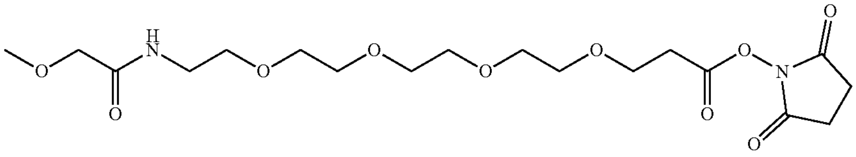
,
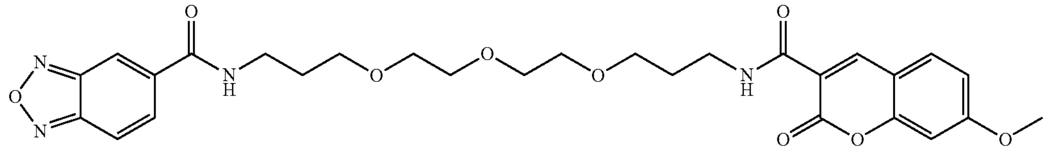
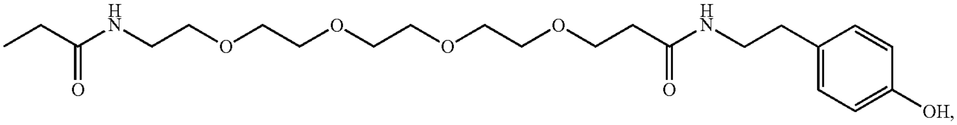
,
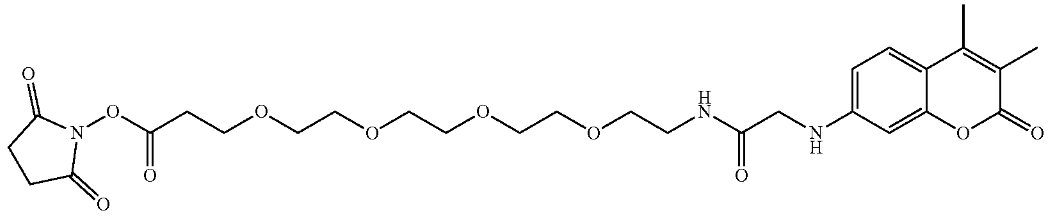
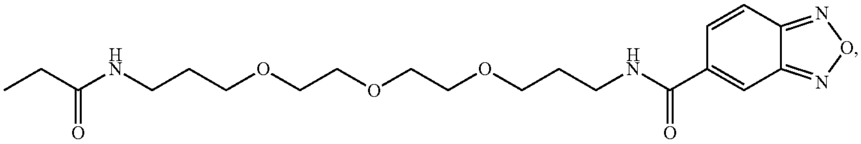
and
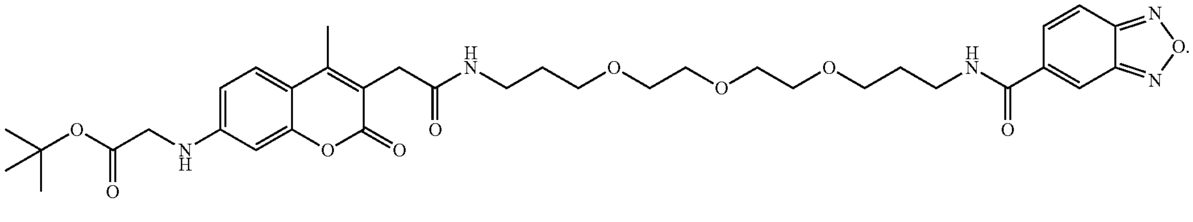

3. A compound selected from the group consisting of
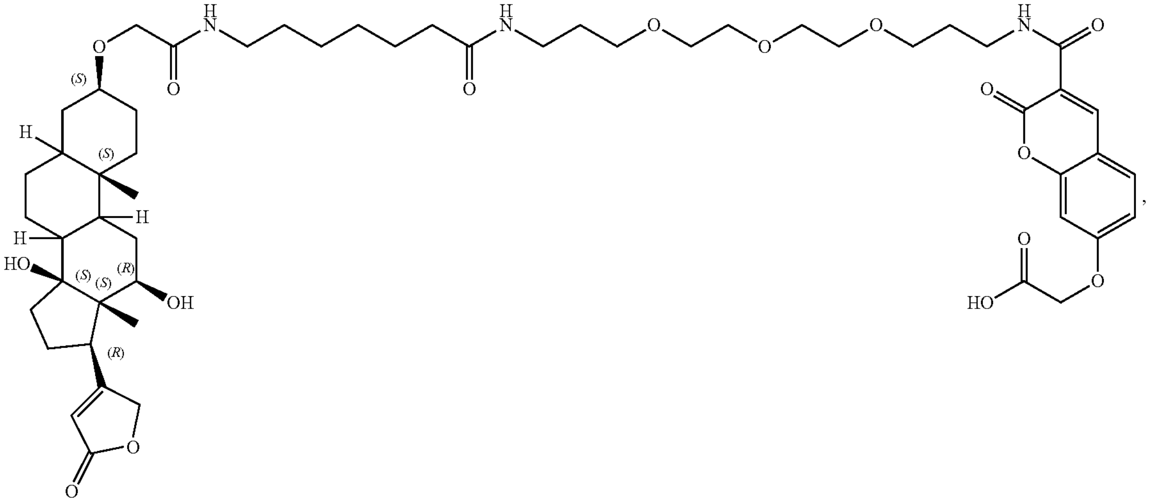
,
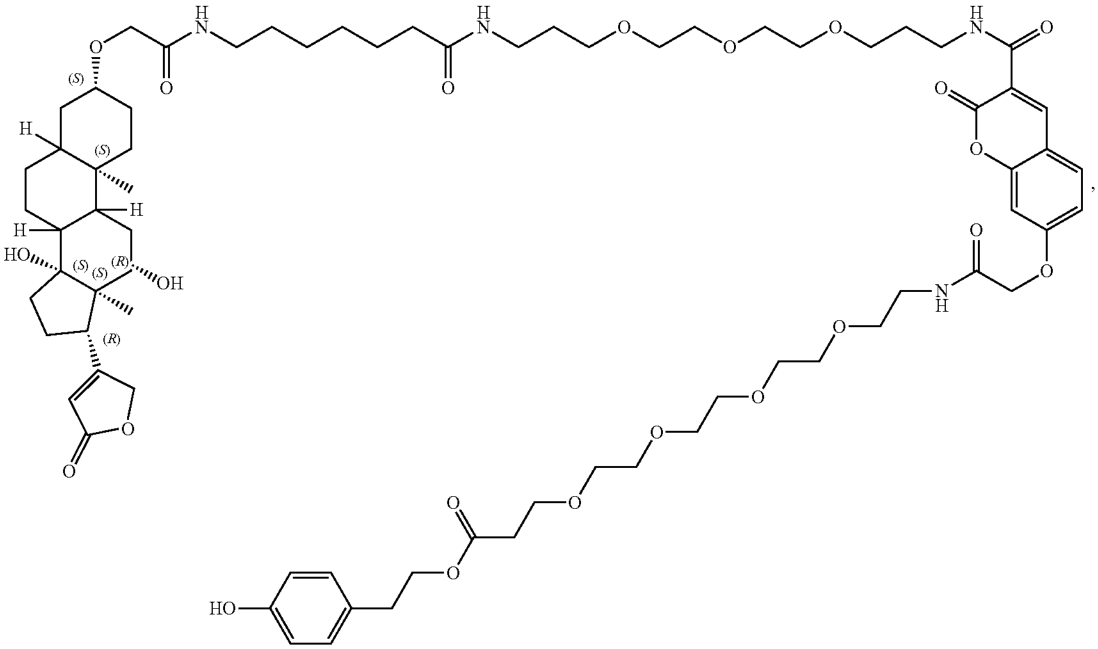
,

-continued
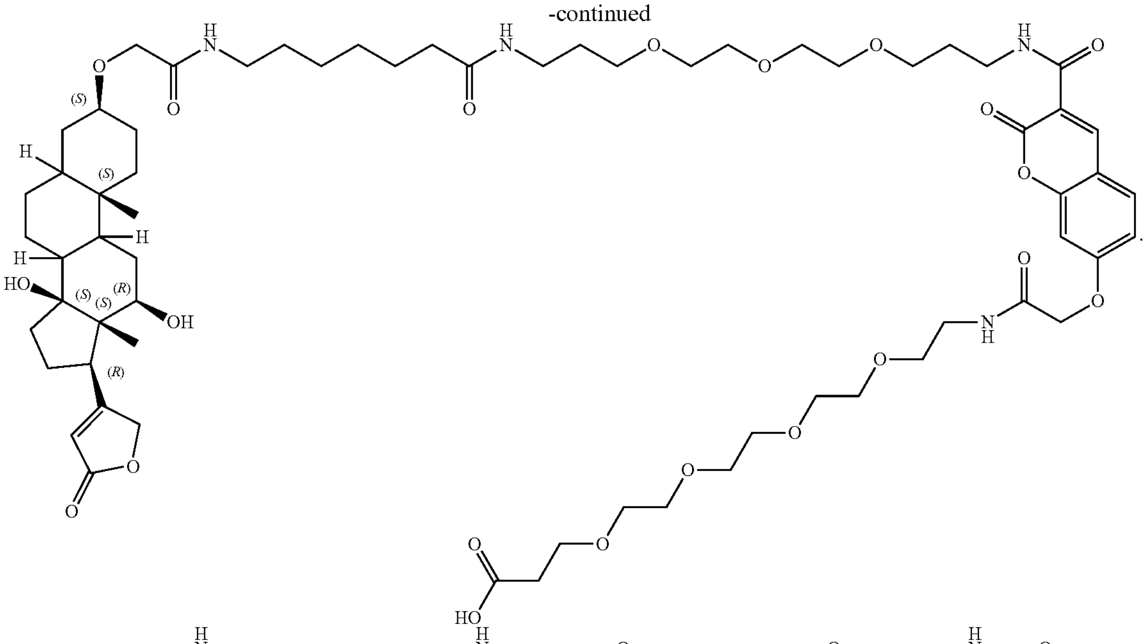
. and
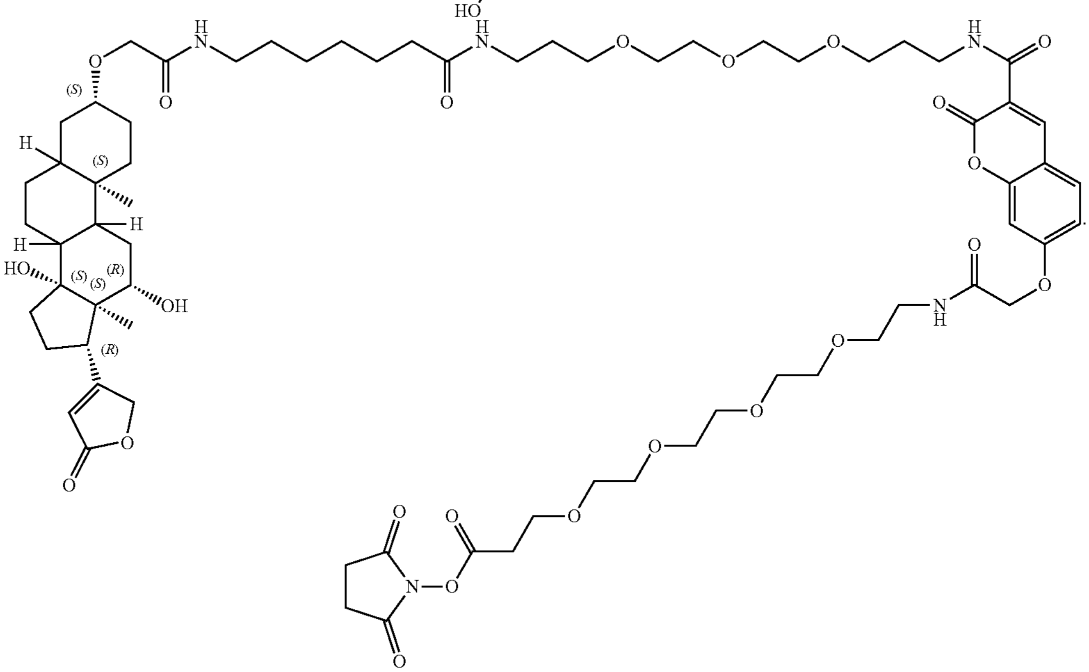
.
* * * * *